United States Patent
Selly

(10) Patent No.: US 11,561,951 B2
(45) Date of Patent: *Jan. 24, 2023

(54) MULTIDIMENSIONAL ASSOCIATIVE MEMORY AND DATA SEARCHING

(71) Applicant: Panvia Future Technologies, Inc., Palo Alto, CA (US)

(72) Inventor: Roger Selly, Palo Alto, CA (US)

(73) Assignee: PANVIA FUTURE TECHNOLOGIES, INC., Palo Alto, CA (US)

( * ) Notice: Subject to any disclaimer, the term of this patent is extended or adjusted under 35 U.S.C. 154(b) by 627 days.

This patent is subject to a terminal disclaimer.

(21) Appl. No.: 16/594,685

(22) Filed: Oct. 7, 2019

(65) Prior Publication Data

US 2020/0034347 A1 Jan. 30, 2020

Related U.S. Application Data

(63) Continuation-in-part of application No. 14/480,355, filed on Sep. 8, 2014, now Pat. No. 10,438,690, which
(Continued)

(51) Int. Cl.
*G06F 16/00* (2019.01)
*G06F 16/22* (2019.01)
(Continued)

(52) U.S. Cl.
CPC ........ *G06F 16/2264* (2019.01); *G06F 16/212* (2019.01); *G06F 16/24532* (2019.01);
(Continued)

(58) Field of Classification Search
CPC ............... G06F 16/2264; G06F 16/212; G06F 16/24532; G06F 16/258
See application file for complete search history.

(56) References Cited

U.S. PATENT DOCUMENTS

| | | |
|---|---|---|
| 5,144,428 A | 9/1992 | Okuda |
| 5,161,204 A | 11/1992 | Hutcheson et al. |
| (Continued) | | |

FOREIGN PATENT DOCUMENTS

| | | |
|---|---|---|
| JP | 2003141538 A | 5/2003 |
| JP | 2005078407 A | 3/2005 |

OTHER PUBLICATIONS

Ezhov, A.A., et al., "Quantum Associative Memory with Distributed Queries", Information Science, vol. 128, p. 271-293, 2000.
(Continued)

*Primary Examiner* — Alexander Khong

(57) ABSTRACT

A method for searching data includes storing a probe data and a target data expressed in a first orthogonal domain. The target data includes potential probe match data each characterized by the length of the target data. The probe data representation and the target data are transformed into an orthogonal domain. In the orthogonal domain, the target data is encoded with modulation functions to produce a plurality of encoded target data, each of the modulation functions having a position index corresponding to one of the potential probe match data. The plurality of encoded target data is interfered with the probe data in the orthogonal domain and an inverse transform result is obtained. If the inverse transform result exceeds a threshold, information is output indicating a match between the probe data and a corresponding one of the potential probe match data.

10 Claims, 26 Drawing Sheets

Related U.S. Application Data is a continuation-in-part of application No. 11/914,554, filed as application No. PCT/US2006/018699 on May 15, 2006, now Pat. No. 8,832,139.

(60) Provisional application No. 60/681,374, filed on May 16, 2005.

(51) Int. Cl.
*G06F 16/2453* (2019.01)
*G06F 17/14* (2006.01)
*G06F 16/21* (2019.01)
*G06F 17/16* (2006.01)
*G06F 16/25* (2019.01)

(52) U.S. Cl.
CPC .......... *G06F 16/258* (2019.01); *G06F 17/141* (2013.01); *G06F 17/16* (2013.01)

(56) References Cited

U.S. PATENT DOCUMENTS

| | | | |
|---|---|---|---|
| 5,706,498 A * | 1/1998 | Fujimiya | G16B 50/00 435/6.12 |
| 6,054,268 A | 4/2000 | Perlin | |
| 6,317,766 B1 | 11/2001 | Grover | |
| 6,321,182 B1 | 11/2001 | Suzuki | |
| 6,466,923 B1 | 10/2002 | Young | |
| 6,551,784 B2 * | 4/2003 | Fodor | C07H 19/10 435/6.12 |
| 6,578,018 B1 | 6/2003 | Ulyanov | |
| 6,718,309 B1 | 4/2004 | Selly | |
| 6,920,451 B2 * | 7/2005 | Shaw | G06F 16/358 707/999.102 |
| 2002/0152191 A1 | 10/2002 | Hollenberg et al. | |
| 2003/0228591 A1* | 12/2003 | Scafe | G16B 30/00 435/6.1 |
| 2004/0193789 A1 | 9/2004 | Rudolf | |

OTHER PUBLICATIONS

Grover, Lov K., "A Fast Quantum Mechanical Algorithm for Database Search", [On-Line]; Nov. 19, 1996; XP002543984; Retrieved from the Internet: URL:htp://arxiv.org/PS_cache/quant-ph/pdf/9605/9605043v3.pdf>: Retrieved on Sep. 2, 2009.

Trugenberger, C.A., "Quantum Pattern Recognition", Quantum Information Processing; vol. 1, No. 6, p. 471-493, Dec. 2002.

Ventura, Dan, et al. "Quantum Associative Memory", Information Sciences, vol. 124, p. 273-296, 2002.

Ventura et al., "Quantum Associative Memory with Exponential Capacity", Neural Networks Proceedings, 1988; IEEE World Congress on Computututional Intelligene; The 1998 IEEE International Joint Conference on Anchorage, AK, USA 4-9; May 1998; New York; USA; IEEE; US vol. 1 May 4, 1998; p. 509-513; XP010286557; isbn: 978-0-7803-4859-2.

Von Ahsen, Nicholas, et al., "Application of a Thermodynamic Nearest-Neighbor Model to Estimate Nucleic Acid Staility and Optimize Probe Design: Prediction of Melting Points of Multiple Mutations of Apolipoprotein B-3500 and Factor V with a Hybridization Probe Genotyping Assay on the LIghtCycler", Clinical Chemistry, vol. 45, No. 12, p. 2094-2101, 1999.

* cited by examiner

| Layer Encoding Index | 0 (64 deep) | 1 (32 deep) | 2 (16 deep) | 5 (2 deep) | 6 (1 deep) |
|---|---|---|---|---|---|
| 0 | $S_0S_1$ | $S_0S_1S_2S_3$ | $S_0 \bullet \bullet \bullet \bullet S_7$ | $S_0 \bullet \bullet \bullet \bullet S_{63}$ | $S_0 \bullet \bullet \bullet \bullet S_{127}$ |
| 1 | $S_2S_3$ | $S_4S_5S_6S_7$ | $S_8 \bullet \bullet \bullet \bullet S_{15}$ | $S_{64} \bullet \bullet \bullet S_{127}$ | |
| 2 | $S_4S_5$ | $S_8S_9S_{10}S_{11}$ | | | |
| ⋮ | ⋮ | ⋮ | | | |
| 31 | | $S_{124}S_{125}S_{126}S_{127}$ | | | |
| ⋮ | ⋮ $S_{124}S_{125}$ | | | | |
| 62 | | | | | |
| 63 | $S_{126}S_{127}$ | | | | |

900

Track 902

MULTIDIMENSIONAL ASSOCIATIVE MEMORY AND DATA SEARCHING

RELATED APPLICATION

This application is a continuation-in-part of U.S. application Ser. No. 14/480,355 (now U.S. Pat. No. 10,438,690), filed Sep. 8, 2014 and entitled "Associative Memory and Data Searching System and Method," which is a continuation-in-part of U.S. application Ser. No. 11/914,554 (now U.S. Pat. No. 8,832,139), filed Nov. 15, 2007 and entitled "Associative Memory and Data Searching System and Method" which is a national stage filing of PCT/US06/018669, entitled "Associative Memory and Data Searching System and Method" and filed May 15, 2006, which claims the benefit of U.S. Provisional Application Ser. No. 60/681,374, entitled "Associative Memory and Data Searching System and Method" and filed May 16, 2005, each of which is hereby incorporated by reference herein in its entirety.

FIELD

The present disclosure generally relates to a method and system for storing and searching large data sets, and more particularly to a method and system for searching data to locate a match to a query and/or to assess a degree of similarity of a query to information stored in the database.

BACKGROUND

The function of an associative memory is commonly used to detect cache "hits" in a computer system by comparing an address word with a memory of address words previously accessed. A "hit" occurs when there are a match between the input address word and an entry in this database. The output of this hit is the cache line where the address was previously read into. An associative memory is therefore in essence a parallel recognition process where a new input is compared with the entire database of prior experiences to detect any match, and in the case of a hit, to output the reference or location.

Parallel recognition processes are conceptually simple, but in actual existing practice grow exponentially in complexity and are unfeasible except for the most limited and small database applications. One potential application of parallel recognition processes is in the searching of DNA/RNA sequences. Such an application of computers to solve information processing problems in the life sciences area is within the general field known as "bioinformatics." However, searches of DNA/RNA sequences typically involve very large databases potentially containing millions to hundreds of millions of bases. These size ranges are inconsistent with the small database sizes suitable for existing parallel recognition processes.

The bioinformatics field, which, in a broad sense, includes any use of computers in solving information problems in the life sciences, and more particularly, the creation and use of extensive electronic databases on genomes, proteomes, etc., is currently in a stage of rapid growth. In order to better appreciate some of the concepts in the bioinformatics field, it is helpful to discuss some of the basic principles of cells.

A cell relies on proteins for a variety of its functions. Producing energy, biosynthesizing all component macromolecules, maintaining cellular architecture, and acting upon intra- and extra-cellular stimuli are all protein-dependent activities. Almost every cell within an organism contains the information necessary to produce the entire repertoire of proteins that the organism can specify. This information is stored as genes within the organism's DNA genome. Different organisms have different numbers of genes to define them. The number of human genes, for example, is estimated to be approximately 25,000.

Genetic information of all life forms is encoded by four basic nucleotides (adenine, thymine, cytosine, and guanine, which are designated by the letters "A", "T", "C", and "G", respectively). The genes are grouped in the base pairs A-T and G-C, and a DNA sequence refers to the ordering or pattern of the nucleotide bases in the gene. The length of a DNA sequence can be very large, and for instance, a DNA sequence may have between 2,000 and two million base pairs. The make-up of all life forms is determined by the sequence of these nucleotides. DNA is the molecule that encodes this sequence of nucleotides.

Each gene typically provides biochemical instructions on how to construct a particular protein. In some cases multiple genes are required to create a single protein, and multiple proteins can be produced through alternative splicing and post-transcriptional modification of a single gene.

Only a portion of the genome is composed of genes, and the set of genes expressed as proteins varies between cell types. Some of the proteins present in a single cell are likely to be present in all cells because they serve functions required in every type of cell. These proteins can be thought of as "housekeeping" proteins. Other proteins serve specialized functions that are only required in particular cell types. Such proteins are generally produced only in limited types of cells. Given that a large part of a cell's specific functionality is determined by the genes that it is expressing, it is logical that transcription, the first step in the process of converting the genetic information stored in an organism's genome into protein, would be highly regulated by the control network that coordinates and directs cellular activity.

There are approximately three billion different DNA base pairs that may be found in humans, and the particular DNA sequences that each person has are located in 23 pairs of chromosomes that contain about 100,000 individual genes. It is significant that faulty genes can be linked to a large variety of human afflictions. An ability to relate an individual gene directly with a particular medical health problem can lead to predictive tests, treatments, and potential cures for a wide variety of medical problems and hereditary ailments.

Currently, about 2,000 human DNA sequences are known and identified, and these DNA sequences are stored in available databases. The number of known and identified human DNA sequences is only a small fraction of the enormous total number of human DNA sequence combinations, and the number of such known and identified DNA sequences is growing rapidly. In addition, the number of DNA sequences of other organisms that have been identified and that are available in databases is also large and likewise growing with time.

The DNA sequence information contained in these growing databases will be a major instrument for basic medical and biological research activities for many years. This information will also be a basis for developing curative techniques for medical and hereditary afflictions. In order to use effectively the information in these enormous and growing databases, it is necessary to provide an efficient means to access that information. In particular, it is necessary to provide an efficient and reliable means to compare a given DNA sequence to the library of known DNA sequences in the databases. Such a comparison is useful to identify, analyze, and interpret that given DNA sequence.

Current procedures for making such comparisons are comparatively slow and impractical. As the amount of stored information increases, current search methods will become unable to function with practical, short processing times, and these methods will have very slow operating speeds. Existing technology is not practical for searching large-scale DNA databases, which may have three billion or more base pair data items.

In addition to the above limitations in searching DNA sequence databases, another of the current limitations on drug discovery research involving the analysis of genome structure and function is the need to perform wet DNA hybridization assays because accurate "in silico" simulations are not available. Further, existing sequence matching tools, such as BLAST, often miss important sequence motifs since they lack the resolution to detect short sequences (e.g., less than 14 bases in length).

In addition to the above limitations in searching DNA sequence databases and drug discovery research, a further limitation is the ability to analyze the biomolecular activity of macromolecules encoded by DNA, whether those are composed of RNA or protein. The analysis of biomolecular activity of macromolecules has been long recognized in the field of biochemistry as being composed of primary structure, secondary structure, tertiary structure and quaternary structure. Primary structure is the one-dimensional sequence of the DNA, RNA or protein. Secondary structure is composed of two-dimensional features comprising two or more primary structure sequences. Examples of secondary structure in RNA are base pairings that form hairpins and stem and loop structures and examples in protein macromolecules are the alpha helix and the beta pleated sheet. In the transformational process of DNA, RNA or protein folding, secondary structure forms first in a process of self-assembly where complementary sequences become proximal and so transition to a lower energy state for the macromolecule. Next, regions of the macromolecule that are differentially hydrophobic and hydrophilic organize to also move to a lower energy state. This involves the hydrophobic regions forming an inner part where water is excluded and the hydrophilic regions assuming an outer part. Complementary three dimensional shapes and charge distributions then fit together to create the tertiary structure that is the resulting three-dimensional shape of the macromolecule. Biological activity often depends on how two or more macromolecules come together to form the quaternary structure, a higher dimensional form that corresponds to a four-dimensional structure. An example is the hemoglobin molecule that self assembles in a pair of pairs structure comprising four separate oxygen binding sites, one in each protein subunit. In this case, the quaternary structure allows the oxygen binding at one heme site to change the oxygen binding affinity of a separate heme site with the result that cooperative binding occurs. The explanation of how this can happen is given by the Monod-Wyman-Changeux model that proposes two conformational states of the four hemoglobin protein subunits that form a hemoglobin molecule.

From the foregoing it is apparent that the biological activity of proteins and RNA, as interpreted from DNA sequence structure, cannot be fully revealed by a search in one dimension corresponding to the primary structure of the DNA. Instead, methods are required to search for secondary structures, tertiary structures and quaternary structures and combine the search results from each separate type of search.

In order to define and formalize a multidimensional search process such as DNA, RNA and protein folding into multiple conformational states it is desirable to define multidimensional data comprising values in a multidimensional grid. For example, black and white images comprise a second (vertical) dimension comprising successive rows in a y coordinate of a first (horizontal) one-dimensional sequence of pixels in an x coordinate. This is the direct extension into two dimensions of previously defining one-dimensional data as a position ordered vector containing searchable components. Three-dimensional data is accordingly a sequence of voxels or volume elements in a three dimensional grid addressable in, for example, an x,y,z Cartesian coordinate system. Multidimensional data is likewise a sequence of values in a multidimensional grid, each value addressable as a multidimensional coordinate position with the number of coordinate axes equal to n, the number of dimensions, by definition. Specifically, for an integer n number of dimensions as a general case, the multidimensional data is a sequence of values in a grid of n dimensions, each value addressable as a n-dimensional coordinate position with the number of coordinates equal to n, the number of dimensions. Regardless of how the multidimensional data is physically stored, it is therefore represented as the value of a real or complex function $h(k1, \ldots, kn)$ defined over the n-dimensional grid $0 \leq k1 \leq N1-1, \ldots, 0 \leq kn \leq Nn-1$, where N1 is the number of grid points in dimension 1 and Nn is the number of grid points in dimension n. In other words, $h(k1, \ldots, kn)$ is a real or complex data value at the n-dimensional coordinates of $(k1, \ldots, kn)$, where the elision marks between k1 and kn denote coordinates in all the dimension between the first and last dimension. Within this document the words multidimensional and n-dimensional will be used interchangeably to mean any case where the number of dimensions is greater than one and where n-dimensional is a specific case of multidimensional where n is the integer number of dimensions.

Accordingly, it would be desirable to search for two-dimensional sequence data patterns in two-dimensional sequence data. Furthermore, it would be desirable to search for three-dimensional sequence data patterns in three-dimensional sequence data, and to search for four-dimensional data patterns in four-dimensional sequence data. As a general case, it would be desirable to search for multidimensional sequence patterns in multidimensional sequence data.

It has long been appreciated that the search space grows exponentially when increasing the number of dimensions, which results in a combinatorial explosion that conventional methods cannot adequately scale to meet and therefore perform slowly or unreliably. Around 1960, Richard E. Bellman called this challenge the "curse of dimensionality" because of the exponential impact on the Dynamic Programming algorithm. To the present time the same combinatorial explosion remains an unsolved challenge in many diverse fields.

Real-time three dimensional object detection, object tracking and object recognition are examples of computational challenges for autonomous vehicles where fast and accurate performance is very important for safety, potentially life-saving for the passenger, pedestrian, cyclist or scooter rider. In an object detection task a database containing unknown objects is searched for instances of a known query object. In an object recognition task a query of unknown object type is compared against a database of known objects. An object tracking task is similar to object recognition except that location and movement vectors are output instead of a binary decision on the presence or absence of an object and its location.

Accordingly, it would be desirable to have an improved solution that overcomes the exponentially growing complexities and combinatorial explosion associated with existing parallel recognition processes in bioinformatics, image processing object detection and recognition, real-time three-dimensional object detection, recognition and tracking, Computed Tomography (CT) 3D scanners, Light Detection and Ranging (LIDAR) sensors signal processing, Magnetic Resonance Imaging (MIll) tissue scan data processing, medical image processing, weather and satellite data, terrain and oceanographic maps, and in other technical fields, and that dramatically reduces associative memory search and retrieval effort. It would be further desirable to have systems and methods to perform multidimensional data with convenient database access, high-speed processing, improved resolution, accuracy, and cost efficiency.

SUMMARY

To address the aforementioned problems with conventional multidimensional data sequence searching, the present disclosure provides methods, computer systems, and non-transitory computer-readable storage media for improved multidimensional data sequence searching. In particular, in some embodiments, a method is performed by a computer system having one or more processors and memory storing instructions for execution on the one or more processors. The method includes storing a first multidimensional probe sequence representation expressed in a first multidimensional orthogonal domain comprising an integer n number of dimensions. The first multidimensional probe sequence representation is characterized by a regional metadata comprising a power metric of all elements in a bounding region comprising a coordinate grid range in each of the n dimensions. The method further includes storing a first multidimensional target sequence representation expressed in the first multidimensional orthogonal domain comprising the integer n number of dimensions. The first multidimensional target sequence includes a plurality of potential multidimensional probe match sequences each characterized by the regional metadata comprising the power metric of all elements in the bounding region comprising the coordinate grid range in each of the n dimensions. The method further includes transforming the multidimensional probe sequence representation and the multidimensional target sequence representation into a second multidimensional orthogonal domain to produce a second multidimensional probe sequence representation and a second multidimensional target sequence representation, respectively. The second multidimensional orthogonal domain is expressible using a basis set that is orthogonal to a basis set of the first multidimensional orthogonal domain. The method further includes encoding the second multidimensional target sequence representation with a first plurality of multidimensional modulation functions in the second multidimensional orthogonal domain, each of the first plurality of multidimensional modulation functions having an integer index to a multidimensional coordinate position corresponding to one of the potential probe match sequences, thereby producing a first plurality of encoded second multidimensional target sequence representations. The method further includes interfering the first plurality of encoded second multidimensional target sequence representations with the second multidimensional probe sequence representation to produce a first set of multidimensional interfered sequence representations. The method further includes encoding the second multidimensional target sequence representation with a second plurality of multidimensional modulation functions in the second multidimensional orthogonal domain, each of the second plurality of multidimensional modulation functions having a multidimensional coordinate position that is a negative counterpart of the multidimensional coordinate position of the first plurality of multidimensional modulation functions for the integer layer index corresponding to one of the potential probe match sequences, and thereby producing a second plurality of encoded second multidimensional target sequences. The method further includes interfering the second plurality of encoded second multidimensional target sequences with the second multidimensional probe sequence representation to produce a second set of multidimensional interfered sequence representations. The method further includes combining each of the first set of multidimensional interfered sequence representations with the complex conjugate of the corresponding counterpart in the second set of multidimensional interfered sequence representations to create a combined multidimensional interfered sequence representation and obtaining an inverse multidimensional transform result characterizing a respective integer index of the multidimensional coordinate position from the combined multidimensional interfered sequence representation. The method further includes determining whether the inverse transform result exceeds a predefined threshold. In accordance with a determination that the inverse transform result exceeds the predefined threshold, information is output indicating that the respective integer index of the multidimensional coordinate position represents a match between the multidimensional probe sequence representation and the corresponding one of the potential multidimensional probe match sequences. On the other hand, in accordance with a determination that the inverse multidimensional transform result does not exceed the predefined threshold, output of information corresponding to the respective integer index of the multidimensional coordinate position index is forgone.

In some embodiments, interfering the first plurality of encoded second multidimensional target sequence representations with the second multidimensional probe sequence representation comprises superimposing the first plurality of encoded second multidimensional target sequence representations and interfering the superimposed encoded second multidimensional target sequence representations with the second multidimensional probe sequence representation.

In some embodiments, interfering the first plurality of encoded second multidimensional target sequence representations with the second multidimensional probe sequence representation comprises performing a multidimensional matrix multiply operation between the plurality of encoded second multidimensional target sequence representation and a complex conjugate of the second multidimensional probe sequence representation.

In some embodiments, transforming the multidimensional probe sequence representation and the multidimensional target sequence representation into the second multidimensional orthogonal domain comprises applying a first unitary multidimensional orthogonal domain transform to the multidimensional probe sequence representation and the multidimensional target sequence representation, respectively. In some embodiments, the first unitary multidimensional orthogonal domain transform is a multidimensional Fourier transform.

In some embodiments, obtaining the inverse transform result characterizing a respective integer index of a multidimensional coordinate position includes applying a second unitary multidimensional orthogonal domain transform to the one or more multidimensional interfered sequence representation. The second unitary multidimensional orthogonal domain transform is an inverse of the first unitary multidimensional orthogonal domain transform. In such embodiments, obtaining the inverse transform result also includes selecting, as the inverse transform result, a result of the second unitary multidimensional orthogonal domain transform applied to the one or more multidimensional interfered sequence representation at a multidimensional coordinate position corresponding to the respective integer index.

In some embodiments, the first multidimensional probe sequence representation is a multidimensional matrix of real or complex numbers. In some embodiments, the first multidimensional probe sequence representation comprises a plurality separately searchable component symbols encoded as multidimensional sequential matrices of real or complex numbers.

In some embodiments the first plurality of multidimensional modulation functions having an integer index to a multidimensional coordinate position corresponding to one of the potential probe match sequences are each obtained from a layer delta function comprising a single non-zero data value at the multidimensional coordinate position corresponding to one of the potential probe match sequences.

In another aspect of the present disclosure, some implementations provide a non-volatile computer readable storage medium. The non-volatile computer readable storage medium includes one or more programs storing instructions that when executed by a computer system with one or more processors and memory the computer system to perform any of the methods provided herein.

In another aspect of the present disclosure, some implementations provide a computer system. The computer system includes one or more processors and memory. The memory stores one or more programs that include instructions that, when executed by the one or more processors, cause the computer system to perform any of the methods provided herein.

BRIEF DESCRIPTION OF THE DRAWINGS

For a more complete understanding of the present disclosure, reference is now made to the following figures, wherein like reference numbers refer to similar items throughout the figures:

FIG. 6 illustrates a multi-resolution database and the segmentation of a target sequence into multiple sections, and the layer encoding applied to each of these sections for each track of the database, in accordance with some embodiments;

The exemplification set out herein illustrates particular embodiments, and such exemplification is not intended to be construed as limiting in any manner.

DETAILED DESCRIPTION

Figure 1A:
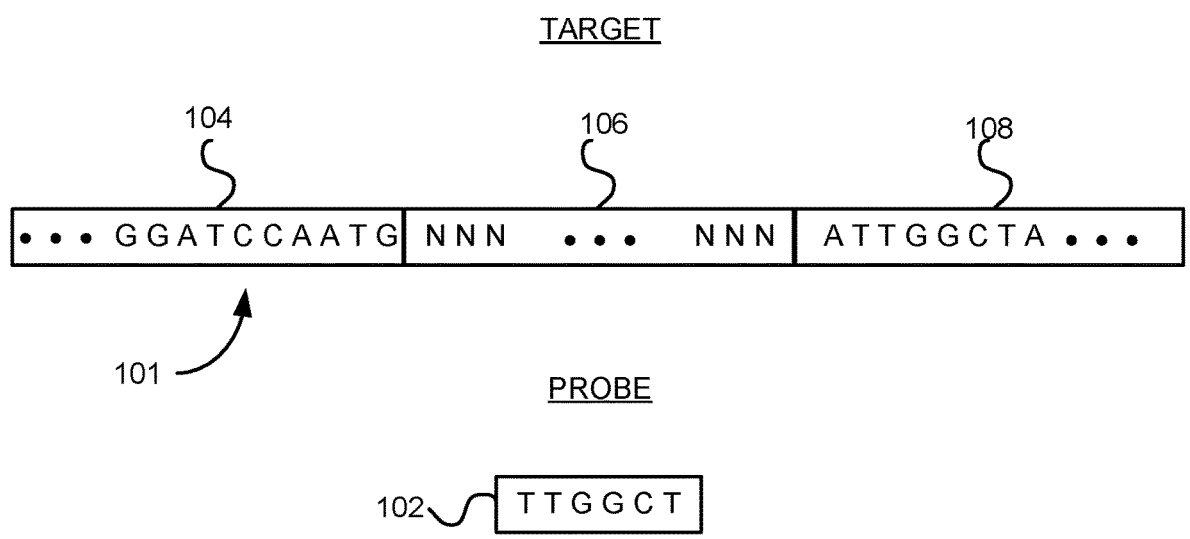
FIG. 1A illustrates an example of a genome target used as an input and a probe used as a query in a sequence searching method, in accordance with some embodiments.
Figure 1B:
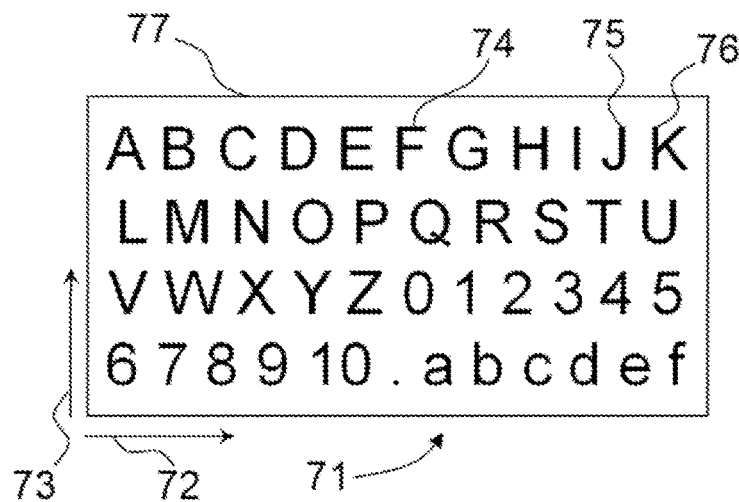
FIG. 1B illustrates an example of a two-dimensional pixel image target used as an input and a two-dimensional pixel image probe used as a query in a two-dimensional data sequence searching method using layer delta functions, in accordance with some embodiments.
Figure 1B:
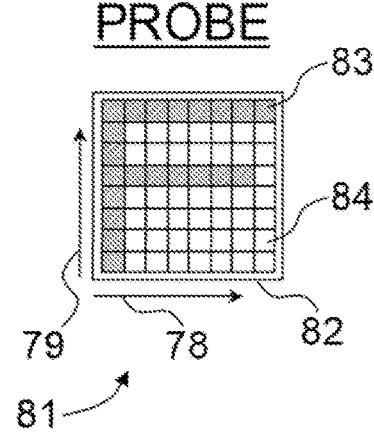
Figure 1B:
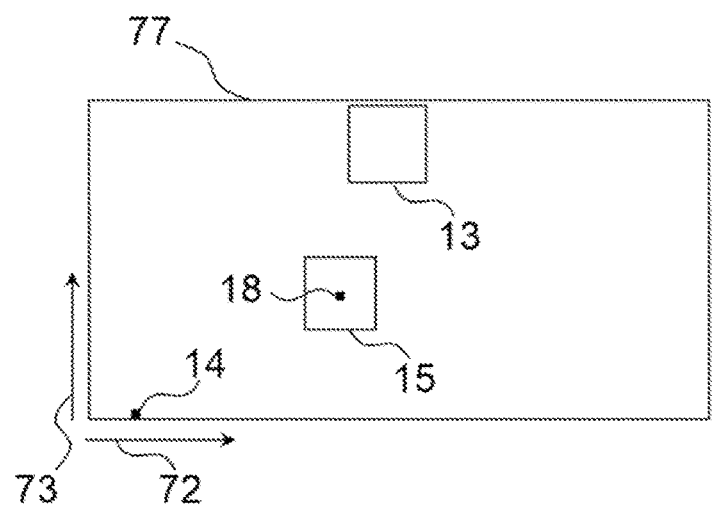

The present disclosure describes methods, computer systems and computer readable storage media for searching, e.g., a long target sequence of numbers for a match to a much shorter probe sequence of numbers. As one specific example, the methods described herein are used to search for a match of a two-dimensional image sequence of pixels (the multidimensional probe sequence) within a two-dimensional image (the multidimensional target sequence) as depicted in FIG. 1B.

The ability to perform such searches quickly may help to develop new medical tests through which a patient's chromosome is searched for a disease-indicating gene variant. Such methods were also described in U.S. application Ser. No. 11/914,554, filed May 15, 2006 and entitled "Associative Memory and Data Searching System and Method," to which the present disclosure claims priority.

Figure 1C:
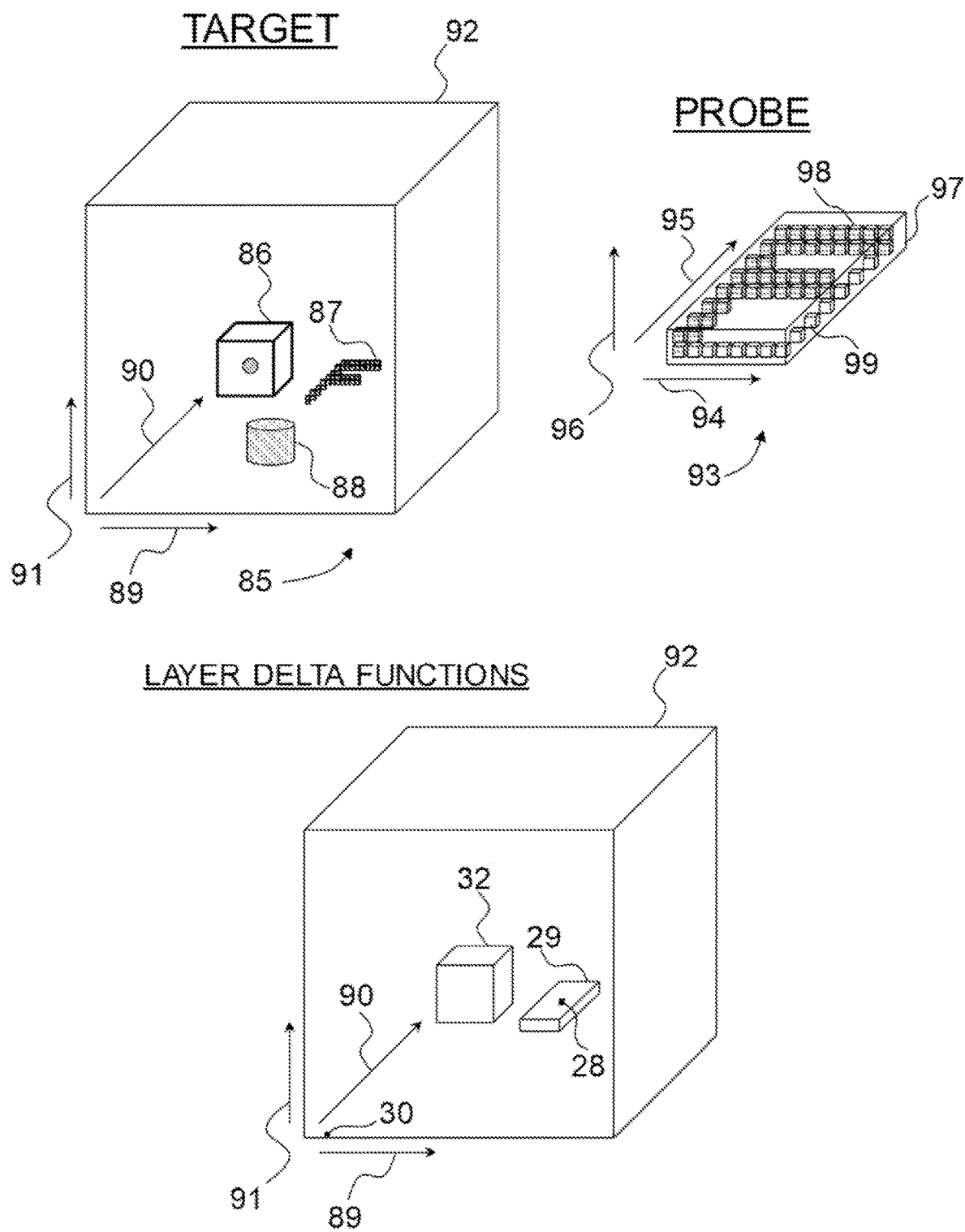
FIG. 1C illustrates an example of a three-dimensional volumetric voxel image target used as an input and a three-dimensional volumetric voxel image probe used as a query in a three-dimensional data sequence searching method using layer delta functions, in accordance with some embodiments.

As another specific example, the methods described herein are used to search for a match of a three-dimensional volumetric image sequence of voxels (the multidimensional probe sequence) within a three-dimensional volumetric image (the multidimensional target sequence) as depicted in FIG. 1C.

As a further specific example, the methods described herein are used to search for a match of an n-dimensional data sequence comprising n-dimensional data elements (the multidimensional probe sequence) within a multidimensional data image comprising multidimensional data elements (the multidimensional target sequence). The ability to perform such multidimensional searches quickly may help to develop new medical tests through which a patient's Magnetic Resonance Image and Computer Aided Tomography scans are analyzed for disease such as the presence of cell abnormalities and tumors. Real-time automated 3D object recognition using Computed Tomography scanner 3D voxel images is another example of the multidimensional data sequence searching method depicted in FIG. 1C.

Such methods were also described in U.S. application Ser. No. 14/480,355, filed Sep. 14, 2014 and entitled "Associative Memory and Data Searching System and Method," to which the present disclosure claims priority.

Within the broad range of applications described in U.S. application Ser. No. 11/914,554 entitled "Associative Memory and Data Searching System and Method," there are important use cases that are subsets of the general method and which allow specific optimizations of the current method to arrive at the same mathematical result via an alternate but equivalent computational path. The most important use case is for all search keys to be at an aligned cursor instead of the non-aligned position capability in the current method, e.g., the only search hits possible are those where the offset position of the probe is zero relative to the layer encoded target wavefunction.

For example, one difficulty with searching a patient's chromosome is that there is no natural modulus to genes within a chromosome. That is to say, rather than a gene starting every ten, 100, or 1,000 base pairs, genes vary in length and, moreover, are mixed up with non-genetic material. Thus, a gene sequence may start and finish at any point within a chromosomal sequence. But much simpler searching applications exist in which there is a natural modulus, and to which important applications still exist. Consider the example of searching for alphanumeric characters: it is known that each character is contained in a separate or discrete region of pixels. The present disclosure further provides optimized search methods for this special case where discrete regions are searched.

The following description and the drawings illustrate specific embodiments sufficiently to enable those skilled in the art to practice the systems and methods described herein. Other embodiments may incorporate structural, logical, process and other changes. Examples merely typify possible variations. Individual components and functions are optional unless explicitly required, and the sequence of operations may vary. Portions and features of some embodiments may be included in or substituted for those of others.

The elements that implement the various embodiments of the present system and method are described below, in some cases at an architectural level. Many elements may be configured using well-known structures. The functionality and processes herein are described in such a manner to enable one of ordinary skill in the art to implement the functionality and processes described herein.

The processing described below may be implemented in the form of special purpose hardware and/or in the form of software or firmware being run by a general-purpose or network or other specialized processor. Data handled in such processing or created as a result of such processing can be stored in any type of memory or other computer-readable medium as is conventional in the art. By way of example, such data may be stored in a temporary memory, such as in the random access memory of a given computer system or subsystem. In addition, or in the alternative, such data may be stored in longer-term storage devices, for example, magnetic disks, rewritable optical disks, and so on. For purposes of the disclosure herein, computer-readable media may comprise any form of data storage mechanism, including existing memory technologies as well as hardware or circuit representations of such structures and of such data.

It should also be understood that the techniques of the present system and method might be implemented using a variety of technologies. For example, the methods described herein may be implemented in software running on a programmable microprocessor, or implemented in hardware utilizing either a combination of microprocessors or other specially designed application specific integrated circuits, programmable logic devices, or various combinations thereof. In particular, the methods described herein may be implemented by a series of computer-executable instructions residing on a storage medium such as a carrier wave, disk drive, or other computer-readable medium. In addition to electronic and semiconductor hardware implementations, several important steps may be functionally implemented using non-electronic media and methodologies such as, for example, using optical components. Furthermore, analog media may provide a lower-cost alternative to digital media for storing or transmitting wavefunctions as described in the methods herein. As a result, it is feasible, in some embodiments, that the wavefunction may be processed starting from an analog storage medium, proceed via an analog processing chain, and then the pattern match results output as an analog signal without the need to pass through a step of conventional electronic digital representation, all according to the functional methods described herein.

One field of endeavor in which the present disclosure may be employed is in the field of two-dimensional (2D) image data sequence searching. Another field of endeavor in which the present disclosure may be employed is in the field of three-dimensional (3D) image data sequence searching. Whereas the two-dimensional image data comprises "picture elements" or pixels, the three-dimensional image data comprises "volume elements" or voxels. However, as will be described below, the disclosure is not limited to either two-dimensional image data sequence searching or three-dimensional data sequence searching and may be employed in other fields involving the analysis of multidimensional records.

A further field of endeavor in which the present disclosure may be employed is in the field of multidimensional data sequence searching, for example, where the analysis and interpretation of complex patterns are performed. In multidimensional data sequence searching, data comprises an image spanning an integer n number of dimensions and containing a multidimensional sequence of data elements. The ability to extend the data sequence searching method from one-dimensional sequence data such as DNA to corresponding methods for two-dimensional sequence searching in two-dimensional data such as pixel images, three-dimensional sequence searching in three-dimensional data such as voxel images and multidimensional sequence searching in multidimensional data will now be discussed. In particular, the differences of the multidimensional data sequence searching method will be described in relation to the previously disclosed one-dimensional data sequence searching methods.

In previous disclosures the quantum effect of superposition was created using a pair of quantum field wavefunctions $\psi R$ and $\psi S$, referred to as an RS pair, formed by summation of target wavefunctions each differentially modulated according to an integer layer index. The output of an interference process between a probe or search wavefunction and a target $\psi R$ and $\psi S$ RS pair is according to the method a correlation between the input probe data and the target data at each layer in the wavefunction superposition of the RS pair.

In previous disclosures the input probe and target data was described as a sequence of real or complex numbers or symbols encoded as sequential vectors of real or complex numbers, each in the form of a one-dimensional position ordered vector containing searchable components. In addition, the method described was with the encoding modulation functions of the wavefunctions for the R superposition having an integer position index and the encoding modulation functions of the wavefunctions for the S superposition having a negative integer position index. Furthermore, the method specified that the output of the interference process is an integer position index.

The present disclosure describes how the same process may be extended to process multidimensional data such as pictures, video, 3D LIDAR (light detection and ranging), MRI 3D tissue scans, satellite data such as weather and terrain, geological and terrestrial spatial tomography. The number of dimensions may be any integer and therefore applications involving multidimensional data of several different orders, for example 1D, 2D and 3D data, or a variable number of dimensions and applications using data with a very high number of dimensions can benefit from the extended multidimensional data method presented herein.

In the method of preparation and interference of multidimensional probe data and multidimensional target data the unitary orthogonal transform and the unitary orthogonal inverse transform are replaced by their multidimensional counterparts: a unitary multidimensional orthogonal transform and a unitary multidimensional orthogonal inverse transform. In addition, the encoding of layers using an integer position index and a negative integer position index is replaced with an integer layer index to a multidimensional coordinate position and a multidimensional negative coordinate position. Also, the modulation functions used to encode the target wavefunctions to the R and S wavefunction superpositions are replaced by multidimensional modulation functions used to encode the multidimensional target wavefunctions to the R and S multidimensional wavefunction superpositions. Furthermore, the output of the multidimensional interference process is an integer layer index of the multidimensional coordinate position corresponding to a potential probe sequence match.

The multidimensional space of coordinate positions used to encode layers in an RS pair using multidimensional modulation functions may be generated from an integer layer index and the integer layer index may be recovered from a multidimensional coordinate position index. In this way, the multidimensional space of coordinate position indexes used to encode layers may be addressed as a linear one-dimensional space.

The generation of a space of multidimensional coordinate position indexes used to encode layers in an RS pair from a one-dimensional integer layer index may use any arbitrary pattern of multidimensional translations. Furthermore, according to the present disclosure the n-dimensional data sequence searching methods include a discrete region method and a continuous region method according to different variants of a Regional Metadata 34. In a continuous region method a continuous dimension in the Regional Metadata defines in which of the n-dimensions the regions are continuous. In the two-dimensional target sequence depicted in FIG. 1B, for example, a horizontal continuous dimension applies for a horizontal line of alphanumeric characters where the horizontal line is partitioned to a series of consecutive horizontal regions. In this case the integer layer index may apply to a horizontal line partition so that the first line can be layer 1, the second line layer 2 and so forth. In some embodiments, the integer layer index is encoded as a coordinate in the continuous dimension in an n-dimensional coordinate position, for example, with the horizontal continuous dimension the two-dimensional coordinate position (1,0) encodes integer layer index 1, the two-dimensional coordinate position (2,0) encodes integer layer index 2, and so on. In such a case the integer layer index may be recovered in the n-dimensional hit detection process from half the horizontal separation of pairs of hits from differentially modulated wavefunction superpositions.

In some embodiments, the integer layer index may be scaled selectively in each of the coordinate dimensions to generate multidimensional coordinate positions. In a two-dimensional image data sequence search application each integer layer index may designate a 2D image frame in a series of video frames. The transformation of the integer layer index to the multidimensional coordinate position may use the integer layer index as the horizontal coordinate x in a two-dimensional (x,y) coordinate position (e.g. integer layer index 0 is transformed to the 2D coordinate position (0,0), layer index 1 is transformed to the 2D coordinate position (1,0), and so forth). Similarly, in a three-dimensional image data sequence search application each integer layer index may designate a 3D image frame in a series of 3D frames. The integer layer index may be transformed to the x coordinate of a three-dimensional Cartesian coordinate position, for example layer 0 is transformed to the three-dimensional coordinate position (0,0,0), layer 1 is transformed to coordinate position (1,0,0), and so on.

The following description will be limited to examples of a sequence search of two-dimensional image data comprising pixels in a two-dimensional Cartesian coordinate grid of x and y coordinate pairs and a sequence search of three-dimensional volumetric image comprising voxels in a three dimensional Cartesian coordinate grid of x, y and z coordinates for the sake of clarity and brevity. Nonetheless, with respect to multidimensional image data sequence searching, it should be noted that while the following description focuses primarily on two-dimensional image data and three-dimensional image data, the disclosure is not limited to use with either two-dimensional image data or three-dimensional image data but can be utilized with data related to any other integer number of orthogonal dimensions in a multi-dimensional coordinate space. The multidimensional sequence data searching method is therefore generally applicable to a wide variety of high dimensionality pattern recognition applications.

The disclosure of a specific embodiment of a quantum computing multidimensional associative memory system and method is now presented below. This disclosure illustrates several aspects that may be provided by this system and method, which may include one or more of the following features: encoding duality using an orthogonal basis; multidimensional orthogonal transforms and domains; unitary multidimensional operations; quantum field multidimensional wavefunctions; qubit phase selection of quantum field multidimensional wavefunctions; superpositions of multiple quantum field multidimensional wavefunctions and interference with superpositions of multiple quantum field multidimensional wavefunctions.

As used herein, a "match" between a multidimensional target and a multidimensional probe may include a 100% match or a match with a lesser degree of similarity. As used herein, a "hit" means a match located from a search of a multidimensional target using a multidimensional probe.

The multidimensional associative memory feature of the present disclosure is illustrated, for example, in the embodiment below in which location and retrieval from memory is determined by the content of the input instead of by some other proxy or label, such as an address, alphabetic index, hash table or any other external attribute, reference or pointer.

The first of several features to reduce hit detection and retrieval effort described herein is the use of superpositions of multidimensional wavefunctions to process multiple layers of encoded multidimensional data in parallel. A two-dimensional data record, such as an image pixel sequence, is mapped as a plurality of superpositions each comprising multiple layers. A location and retrieval task involves searching the entire database for matches between an input probe or query sequence and the target data sequence. If a match is present, then its location is output. In the present disclosure this location corresponds, for example, to two coordinates: the index of the layer where the matching sequence is located; and the offset within the layer where the match is present. The wavefunction superposition comprising a database therefore may contain a two-dimensional search space in which any sequences in the database that match the probe may be located in this search space by a layer dimension index and an offset dimension index.

Another feature to help reduce hit detection and retrieval effort is the use of layer encoding modulation to create superpositions of wavefunctions such that the layer where a hit is located may be read by means of a layer profile.

In other words, one of the of the features of the present disclosure is the providing of an efficient method for first encoding, then later extracting, the layer index of any matches between the probe sequence and the target database. This implements an associative short-cut that avoids an exhaustive search of each layer in turn. Once the layer index has been identified, the full search space has been narrowed down to a single layer or page. This feature is described as measurement of the layer profile.

The layer profile allows all layers in a superposition to be processed as one layer, compressed into a single record, with the resulting output being a profile of the match correlation between probe and target and the match distance metric for each layer. This provides a faster and more efficient way to evaluate if any match is present between the probe (e.g., query or new experience) and the target (e.g., database or sum of past experiences), and if there is, to output the specific index of the layer in the superposition where that match is located.

As is described in greater detail below, the location of the match within the layer selected by the layer profile described above may be extracted by forming an interference viewpoint selected by the layer index. The interference viewpoint may be constructed by using one or more superpositions to interfere with the probe wavefunction. In the case where more two or more superpositions are used, as discussed further below, the process of constructing this viewpoint involves performing an extraction operation to combine the outputs of the first interference process. In this way, the first interference process may be used to generate intermediates (which may be temporarily stored in storage buffers during computations). These are common to both the layer profile process to read the layer index as mentioned above, and also the process to extract the interference viewpoint of that selected layer, which allows reading of a search coordinate equal to the offset position in that layer.

The layer profile process therefore comprises an interference between one or more superpositions and the probe wavefunction. The specific architecture associated with this process has the encoding of the layer index in each of the separate wavefunctions that are combined into superpositions.

It should be noted that the layer profile may be used to process the entire multidimensional target database for any and all matches to the multidimensional input probe: it is a de novo calculation of the multidimensional correlation between the multidimensional probe and the multidimensional target database for all reading frames and sequence alignments within the entire database sequence, such as two-dimensional pixel images, three-dimensional volumetric voxel images, and any positive integer number of dimensions that is generalized as a multidimensional image comprising an integer n dimensional volume containing various data elements. The output of this distance calculation exists as the output of a multidimensional interference process, and may be stored as a multidimensional intermediate wavefunction. For example, as illustrated in FIG. 5E-5F (to be discussed in more detail below), the output of the multidimensional interference process is stored as multidimensional intermediate wavefunctions in storage buffers 125 and 143. Here, two multidimensional orthogonal superpositions (designated "R" and "S" and provided at steps 111 and 129 of FIGS. 5E-5F) are used to generate the multidimensional intermediate wavefunctions stored in multidimensional storage buffers 125 and 143, and each multidimensional intermediate wavefunction may be represented as a multidimensional matrix of real or complex numbers.

The specific properties of the layer encoding are such that layer encoding is designed to be orthogonal to position encoding. Because wavefunction superpositions are employed that actually comprise multiple wavefunction layers in a single wavefunction, each stage of the layer profile process is the size of a single dimension of the search space (i.e., a single wavefunction). It is the particular architecture of orthogonal encoding and decoding operations in the present disclosure that allows this processing gain to be realized. In practice this processing gain means that, using a pair of multidimensional data matrixes comprising superpositions of multidimensional wavefunctions of complex numbers equivalent in size to a single dimension of the search space, it is possible to process a match correlation for an entire two-dimensional, three-dimensional and multidimensional search space for any integer n number of dimensions.

Additional aspects of the system and method of this disclosure will now be described in even greater detail for the particular embodiment of two-dimensional image pixel sequence searching. An example of a target two-dimensional image used as an input in image pixel sequence searching is depicted in FIG. 1B, wherein one or more two-dimensional images are defined as regions 74, 75, and 76 of a pixel sequence on the two-dimensional image 71. The pixels are identified as black and white or opaque and transparent. The two dimensional image 71 has a horizontal x-axis 72 and a vertical y-axis 73 and each pixel in the two-dimensional image is specified by a unique pair of x and y coordinates, for example p(x,y) may designate a pixel value at the coordinate position (x,y) in a two-dimensional Cartesian coordinate space. Target 71 has a bounding region 77 comprising a grid range of pixels in each dimension. In the example shown in FIG. 1B the bounding region 77 may be defined as pairs of coordinates for opposite corners of the two-dimensional rectangular area contained within it. In general, a two-dimensional image pixel sequence to be searched is referred to as a "pixel target" below, and the pixel target is typically separated into a number of regions of defined length for purposes of processing.

An example of a probe two-dimensional image 81 is also depicted in FIG. 1B. Probe 81, in this example, is a two-dimensional image comprising sixty-four pixels arranged as eight vertically consecutive rows, each of eight horizontally consecutive pixels. Each pixel in probe 81 is specified by a unique pair of x and y coordinates according to their position relative to the horizontal x-axis 78 and the vertical y-axis 79. Each pixel in probe 81 has a value p(x,y), and some p(x,y) values may designate that the pixel appears darker or opaque as shown for pixel 83, while other p(x,y) values may designate that the pixel appears lighter or transparent as shown for pixel 84. The value p(x,y) may represent any property or attribute of the pixel, for example density, temperature or velocity represented as a real or complex number. Probe 81 is characterized by a power metric of all the elements in a bounding region 82 comprising a coordinate grid range in each of the two dimensions, which in the example shown is eight pixels in each of the horizontal and vertical image dimensions. In one example, a transparent pixel 84 will have a zero value and a shaded pixel 83 will have a non-zero value. The power metric characteristic of probe 81 is the total of the pixel values squared in the bounding region 82, which is eight pixel range in each dimension for a total of sixty-four pixels in the example shown.

According to the present disclosure the pixel target in FIG. 1B may be separated into continuous or discrete regions where, for example, continuous regions may comprise multiple alphanumeric characters in a horizontal line and discrete regions may comprise individual alphanumeric characters. The continuous regions may be used in data sequence searching methods for continuous regions and the discrete regions may be used in data sequence searching methods for discrete regions. Also, according to the present disclosure, multiple pixel targets may be processed, for example, target image 71 may represent a single frame in series of video frames.

Additional aspects of the system and method of this disclosure will now be described in even greater detail for the particular embodiment of two-dimensional image pixel sequence searching. The target two-dimensional image used as an input in image pixel sequence searching depicted in FIG. 1B is encoded as a plurality of layers in a two-dimensional wavefunction superposition pair that will be described in greater detail below with reference to FIG. 4B and a target wavefunction superposition preparation method 105. The target wavefunction superposition preparation method 105 encodes each layer in the two-dimensional wavefunction superposition pair using a separate delta function for each layer, which is identified by an integer layer index. For one particular integer layer index, a layer delta function 14 comprises a single non-zero value at a two-dimensional coordinate that may be used to encode a layer comprising a line of alphanumeric characters where the line is subdivided into multiple regions as depicted by a bounding region 13 inside the target bounding region 77. For another particular integer layer index, the layer delta function 18 comprises a single non-zero value at a two-dimensional coordinate within a bounding region 15 which is also inside the target bounding region 77.

Additional aspects of the system and method of this disclosure will now also be described in even greater detail for the particular embodiment of three-dimensional volumetric image voxel sequence searching. An example of a three-dimensional volumetric target image used as an input in image voxel sequence searching is depicted in FIG. 1C, wherein one or more three-dimensional volumetric images are defined as regions 86, 87 and 88 of a voxel sequence in the three-dimensional target image 85. The voxels are identified as black and white or opaque and transparent. The three-dimensional target image 85 has a horizontal x-axis 89, a horizontal y-axis 90 and a vertical z-axis 91. Each voxel in the three-dimensional image target 85 is specified by three spatial coordinates, for example v(x,y,z) may designate a voxel value at coordinate position (x,y,z) in a three-dimensional Cartesian coordinate space. Target 85 has a grid range of voxel elements in each dimension which is depicted as the volume inside a bounding region 92. In the example shown in FIG. 1C the bounding region 92 may be defined as pairs of coordinates for opposite corners of the three-dimensional cuboid volume contained within it. In general, a three-dimensional image voxel sequence to be searched is referred to as a "voxel target" below, and the voxel target is typically separated into a number of regions of defined length for purposes of processing.

According to the present disclosure the pixel target in FIG. 1C may be separated into continuous or discrete regions where, for example, continuous regions may comprise multiple three-dimensional objects in a horizontal section and discrete regions may comprise individual objects. The continuous regions may be used in data sequence searching methods for continuous regions and the discrete regions may be used in data sequence searching methods for discrete regions. Also, according to the present disclosure, multiple voxel targets may be processed, for example, target image 85 may represent a single 3D scan in series of 3D scans.

An example of a three-dimensional probe 93 is also depicted in FIG. 1C. Probe 93, in this example, has vertically consecutive horizontal planes of voxels with each horizontal plane comprising sixty-four voxels arranged as eight coplanar consecutive rows. Each voxel in probe 93 is specified by a unique combination of x,y and z coordinates according to their position relative to the x-axis 94, y-axis 95 and z-axis 96. Each voxel in probe 93 has a value v(x,y,z) and some v(x,y,z) values may designate that the voxel appears darker or opaque as shown for voxel 98, while other v(x,y,z) values may designate that the voxel appears lighter or more transparent as shown for voxel 99. For the purpose of clarity, some of the transparent voxels are not shown in FIG. 1C. The value v(x,y,z) may represent any property or attribute of the voxel, for example density, temperature or velocity represented as a real or complex number. Probe 93 is characterized by a power metric of all elements in a bounding region 97 comprising a coordinate grid range in each of the three dimensions, which in the example shown is eight voxels in each of the horizontal x and y dimensions and two voxels in the vertical z axis dimension. In one example, a transparent pixel 99 will have a zero value and a shaded pixel 98 will have a non-zero value. The power metric characteristic of probe 94 is the total of the voxel values squared over all the voxels in the bounding region 97. For the example shown, the voxel range comprises eight voxels in each horizontal dimension and two voxel range in the vertical dimension, for a total of one hundred and twenty-eight voxels as shown with some transparent voxels omitted for clarity.

Additional aspects of the system and method of this disclosure will now be described in even greater detail for the particular embodiment of three-dimensional image voxel sequence searching. The target three-dimensional image used as an input in image voxel sequence searching depicted in FIG. 1C is encoded as a plurality of layers in a three-dimensional wavefunction superposition pair that will be described in greater detail below with reference to FIG. 4B and target wavefunction superposition preparation method 105. The target wavefunction superposition preparation method 105 encodes each layer in the three-dimensional wavefunction superposition pair using a separate delta function for each layer, which is identified by an integer layer index. For one particular integer layer index, the layer delta function 28 comprises a single non-zero value at a three-dimensional coordinate within a bounding region 29 which is inside target bounding region 92. For another particular integer layer index, the layer delta function 30 comprises a single non-zero value at a three-dimensional coordinate that may be used to encode a layer comprising a section of the target bounding region 92 and the section may be subdivided into multiple regions as depicted by the bounding region 32.

Figure 2:
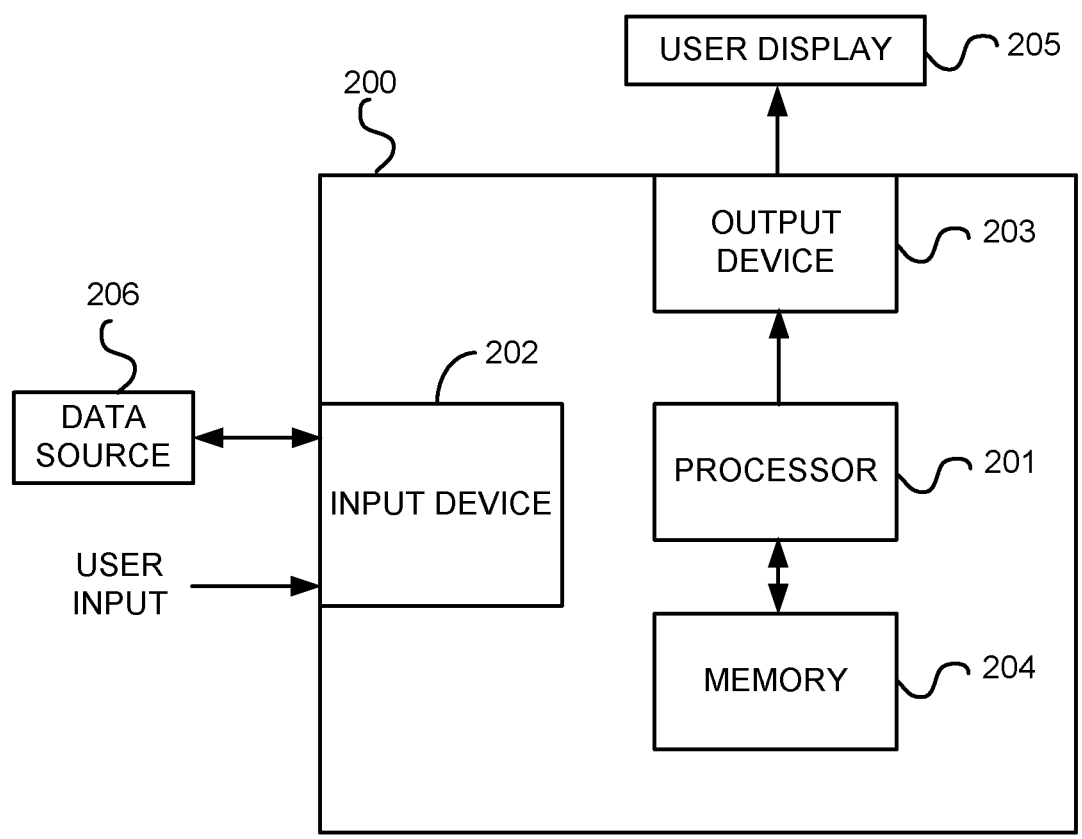
FIG. 2 illustrates a computer system that may be used to implement the search of the images target of FIGS. 1A-1C.

A block diagram depicting the components of a computer system that may be used with the methods of the present disclosure is provided in FIG. 2. Computer system 200 comprises an input device 202 for receiving data regarding a target to be searched and a probe (i.e., query) to use in conducting this search. The target may be, for example, two-dimensional sequence of pixels regarding target image 71, three-dimensional sequence of voxels regarding target image 85, or an n-dimensional sequence of data for any number of dimensions greater than one. The data may be received from data source 206, which may be, for example, another computing device coupled to computer system 200 using, for example, the Internet or a local area network. Input device 202 may include multiple ports for receiving data and user input. The user input may be dynamically interactive with computer system 200 and be responsive to information provided to the user on a user display 205 or other user output device. Typically, user input is received from conventional input/output devices such as, for example, a mouse, trackball, keyboard, light pen, etc., but may also be received from other means such as voice or gesture recognition.

An output device 203 is coupled with a processor 201 for providing output through various possible interfaces. Output to a user on user display 205 may be provided on a video display such as a computer screen, but may also be provided via printers or other means. Output may also be provided to other computer systems, devices or other programs for use therein. For example, computer system 200 may be a Web server used to provide data searching services as an application service provider. For example, search results may be presented on user display 205 as a map showing direct hits and close homologies for a given probe.

Input device 202 may be coupled with processor 201, which may be, for example, a general-purpose computer processor or a specialized processor designed specifically for use with the present disclosure. Processor 201 may also comprise, for example, multiple processors working in parallel. Processor 201 may be coupled with memory 204 to permit storage of data used in the methods described herein and to store computer programs to be executed by processor 201. Memory 204 may be implemented as several memories or may be partitioned for storage of different data types. Memory 204 may be used, for example, to provide numerous storage buffers for intermediates that are used in calculations for the searching methods described herein.

As previously mentioned, the terms multidimensional and n-dimensional are used interchangeably and n-dimensional is a specific case of multidimensional where n is the integer number of dimensions. The use of n-dimensional to describe method steps therefore references a specific case n of a general multidimensional method and all steps so described will have the same number n of dimensions as an input and output.

Figure 3A:
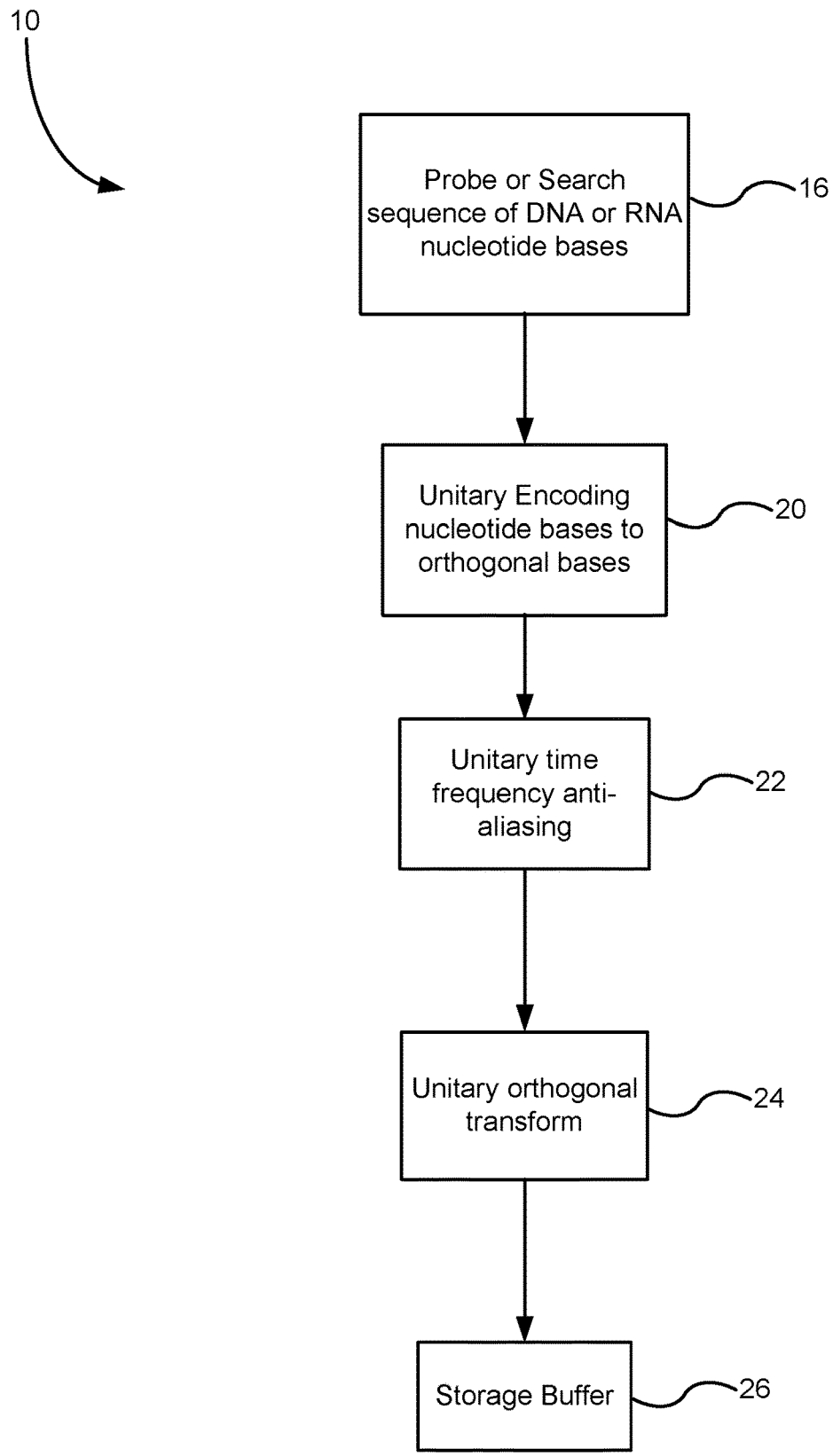
FIG. 3A illustrates the transformation of a probe sequence to a wavefunction for use in sequence searching, in accordance with some embodiments.

FIG. 3A illustrates a method 10 for the transformation of a probe sequence (e.g., a DNA sequence) to a wavefunction for use in DNA or RNA sequence searching. The preparation of the DNA or RNA probe sequence by transformation to a wavefunction starts with an input probe or search sequence of DNA or RNA nucleotide bases 16. This is typically in the format of a text file, known as a "Fasta" file, where each nucleotide base of DNA or RNA is encoded using its initial letter. For example, each line of a Fasta file may contain up to fifty ASCII text characters encoding the same number of DNA or RNA nucleotide bases. For the purpose of the present description the probe or search sequence will be the instance of what is being searched for in a much larger database, such as a chromosome or genome, or any part or combination of these.

The probe sequence may encode any sequence of interest from the very short through to the very long. This may be, for example, a short oligonucleotide fragment such as a small interfering "siRNA" of just 22 bases, or a palindrome sequence, a duplex forming structure or any other possibility. The present method is may be used with short probe lengths such as, for example, one to twelve bases in length. Alternatively, very long DNA and RNA sequences of several thousands of base pairs may be used as the probe sequence.

The input sequence 16 is processed by a unitary encoding of the nucleotide base sequence to a vector in an orthogonal basis 20. As applied to DNA and RNA sequence searching, the present method achieves an orthogonal and unitary mapping between each of the four nucleotide bases (Adenine, Thymine, Guanine and Cytosine in the case of DNA; or Adenine, Uracil, Guanine and Cytosine in the case of RNA) and the four phase quadrants in a complex number plane (e.g., points around a unit circle). For example, this mapping in a graph in which the x-axis represents a real component and the y-axis an imaginary component may be represented as follows for a DNA sequence: A (1, 0), C (0, j), T (1, 0), and G (0, −j). The output of step 20 is a data representation of a vector of complex numbers. In this specific embodiment, the length of this complex vector is equal to the length in number of bases of the input probe nucleotide sequence (e.g., seven bases in length).

The output of step 20 is then passed to the next step in the process, which is a unitary time frequency anti-aliasing 22. This step is done to remove aliasing of position of the input sequence due to transform periodicity equal to the complex frame size (2N or 4,096 in the exemplary case discussed herein). Such aliasing may cause ambiguity in the orthogonal transform that would violate the unitary (or 1:1 mapping) principle of the present disclosure, which is desired for symmetry of information flow either backwards or forwards via a complex field equivalent. To preserve the unitary principle, this aliasing must be removed. This may be accomplished by appending to the output of step 20 an equal length complex vector comprising real and imaginary components each having all values of zero. The output of step 22 would therefore be a complex vector at least twice the length of the input probe nucleotide sequence. For this specific embodiment, an additional number of real and imaginary component with zero value are appended to the probe so that the output complex vector from step 22 has a length equal to twice the length of the frame size that will be used for encoding portions of the target sequence, which frame size is discussed further below. In the embodiment described below, the frame size is selected to be 2,048 bases, and so the output of step 22 is a complex vector with a length of 4,096 complex elements (where each complex element has a real and an imaginary component).

The output of step 22 is next processed by a unitary orthogonal transform 24. This maps the input data representation of a complex vector to an output complex vector in an orthogonal dimension or domain. In addition to the input and output domains being mutually orthogonal, each element of the input complex vector is equivalently represented by a basis function that is orthogonal to each of the other basis functions in that input domain. Symmetrically, each element of the output complex vector is equivalently represented by a basis function that is orthogonal to each of the other basis functions in that output domain.

While many possibilities exist for the unitary orthogonal transform 24 that meet the criteria specified above, for the purposes of the present embodiment the specific instance of the unitary orthogonal transform will be implemented as a discrete Fourier transform. Transforms that may be used in other embodiments include, for example, transforms based on prime number theory, Hadamard transforms, Sine, Cosine, Hartley, as well as many potential wavelet transforms.

Following the unitary orthogonal transform 24, the probe is now represented by a wavefunction in the form of a complex vector. For the specific example discussed below for a frame size of 2,048 bases, this complex vector contains 4,096 complex elements (where each complex element has a real and complex component). The probe is stored in storage buffer 26, to retain the probe in memory prior to interference with other wavefunctions from the target (discussed below). For purposes of later reference, this stored wavefunction is designated as φ. Storage buffer 26 may be implemented in memory 204 of computer system 200, or in another storage device. The stored probe wavefunction may serve as a resource that can be reused if multiple interference processes need to use this wavefunction. Such storage of the probe often may be more efficient and economical compared to serially repeating the wavefunction preparation process. This intermediate may also be used immediately without storage.

Figure 3B:
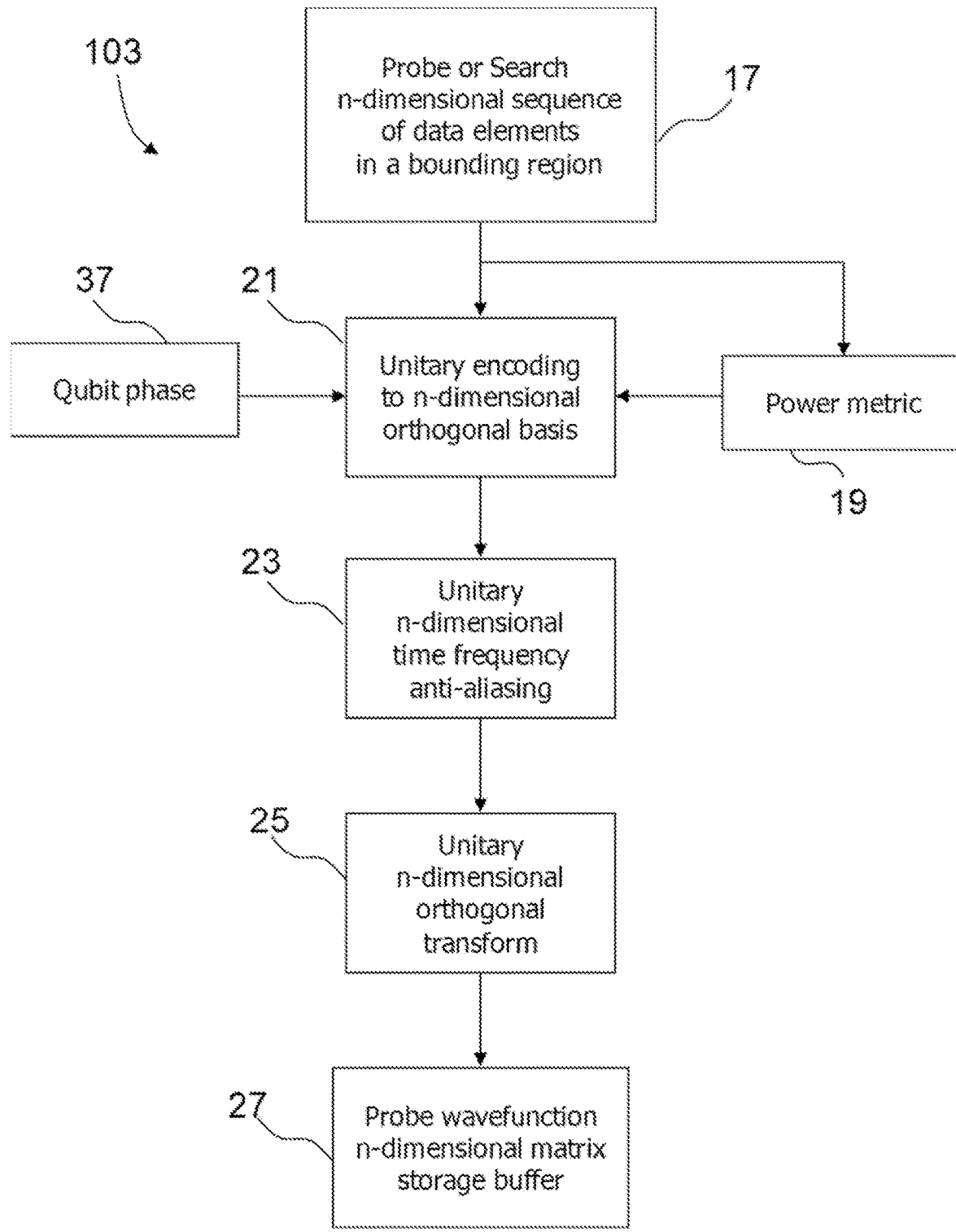
FIG. 3B illustrates the transformation of an n-dimensional probe sequence to an n-dimensional wavefunction for use in n-dimensional data sequence searching, in accordance with some embodiments

FIG. 3B illustrates a method 103 for multidimensional probe data sequence preparation to a multidimensional probe wavefunction for use in multidimensional data sequence searching where the number of dimensions n is greater than one. The transformation of an n-dimensional probe sequence for example, a two-dimensional pixel image 71, a three-dimensional voxel image 85, or multidimensional data in any integer n number of dimensions greater than one, as an n-dimensional sequence of data elements) to an n-dimensional wavefunction for use in n-dimensional data sequence searching. The preparation of the n-dimensional probe sequence by transformation to a n-dimensional wavefunction starts with an input n-dimensional probe or search sequence of data elements 17. For example in the case where n is two, the input 17 is a two-dimensional image of two-dimensional picture elements or pixels. This is typically in the format of a binary file, such as the type known as a "bmp" file, where each pixel is encoded using its binary value. For example, each pixel of a bmp file may contain eight bits encoding different u-norm values from 0 representing black to 255 representing white. For the purpose of the present description the probe or search sequence will be the instance of what is being searched for in a much larger database, such as a collection of n-dimensional images such as 3D scans, or any part or combination of these.

The n-dimensional probe sequence may encode any sequence of interest from the very short through to the very long. This may be, for example, a short pixel fragment such as a texture patch, or a three-dimensional volumetric concave or convex shape, or any n-dimensional manifold. The present method may be used with short probe lengths such as, for example, sixty-four pixels in length. Alternatively, very long pixel and voxel sequences of several thousands or millions of pixels or voxels may be used as the n-dimensional image probe sequence.

The n-dimensional input sequence 17 is characterized by a bounding region containing pixels. For the purposes of the present method the n-dimensional input sequence 17 is further characterized by a power metric inside the bounding region. To provide this characterization, the n-dimensional input sequence 17 is passed to step 19 which calculates the total power of the n-dimensional input sequence 17 for the purpose of downstream pixel sequence searching. The power metric value output from step 19 is combined with the n-dimensional input sequence 17 by step 21, a unitary encoding to n-dimensional orthogonal basis. Accordingly, step 21 receives the input pixel sequence within any bounding region 17, which is also characterized by the power metric 19. The power metric calculation step 19 is, for example, a sum of the squared pixel values in the bounding region across all n dimensions.

The unitary encoding to n-dimensional orthogonal basis 21 may receive an additional input of a qubit phase 37 which may be a search parameter that is obtained for the input probe or search sequence 17. The qubit phase 37 may be represented as a complex number that determines the selections in a circular space comprising the complex phase of individual layers in the wavefunction superposition RS pair. The circular phase represented by qubit phase 37 may be used as an extra dimension in computations that is either a discrete or continuous variable. In the discrete variable case the circular space may be divided for example into four orthogonal spaces each comprised of a quadrant in the range plus or minus 45° with respect to each positive and negative real and imaginary axis of the unit circle in the complex plane. In the continuous variable case the circular space may for example represent direction in space or distance between two locations inside a loop.

The n-dimensional input sequence 17 is processed by the unitary encoding of the n-dimensional sequence of data elements to an n-dimensional matrix in an n-dimensional orthogonal basis 21. As applied to two-dimensional image pixel sequence searching, three-dimensional voxel image sequence searching or multidimensional data sequence searching, the present method achieves an orthogonal and unitary mapping between the real or complex data values at each pixel, voxel or multidimensional data element, which may be for example a color, density, reflectiveness attribute, and a matrix of complex numbers, where the matrix has the same number of dimensions n equal to the number of dimensions in the n-dimensional input sequence 17. The qubit phase 37, represented as a complex value, may be applied to the real or complex data values at each pixel, voxel or multidimensional data element using complex multiplication to generate the output of step 21.

A specific example of unitary encoding to n-dimensional orthogonal basis 21 will now be given where the input probe or search n-dimensional sequence of data elements are real numbers such as a color, density or reflectiveness attribute. The specific example is for a length of $N1, \ldots, Nn$ elements in each of then dimensions. The unitary encoding output of step 21 is a matrix of complex numbers with the same number of dimensions n as the input 17 n-dimensional sequence of real valued data elements. For an input comprising an n-dimensional sequence of real elements in n dimensions having lengths $(N1, N2, \ldots, Nn)$ the output of step 21 is a matrix comprising complex data elements in n dimensions having lengths $(N1, N2, \ldots, Nn)$.

The output of step 21 is then passed to the next step in the process, which is an n-dimensional unitary time frequency anti-aliasing 23. This step is done to remove aliasing of position of the input sequence due to multidimensional transform periodicity equal to the complex matrix size $((N1, N2, \ldots, Nn)$ in the n-dimensional data searching exemplary case discussed herein). Such aliasing may cause ambiguity in the multidimensional orthogonal transform that would violate the unitary (or 1:1 mapping) principle of the present disclosure, which is desired for symmetry of information flow either backwards or forwards via a complex field equivalent. To preserve the unitary principle, this aliasing must be removed. This may be accomplished by appending to the output of step 21 in each dimension of the matrix, an equal sized n-dimensional complex matrix comprising real and imaginary components each having all values of zero. The output of step 23 would therefore be a n-dimensional complex matrix at least twice the size of the input n-dimensional probe data sequence in each dimension. For the n-dimensional data searching exemplary case discussed herein the input complex matrix size $(N1, N2, \ldots, Nn)$ will generate an output complex matrix size $(2N1, 2N2, \ldots, 2Nn)$. For this specific embodiment, an additional number of real and imaginary components with zero value are appended to the probe so that the output complex matrix from step 23 has a length in each dimension equal to twice the length of the matrix size that will be used for encoding portions of the multidimensional target sequence, which matrix size is discussed further below. In the embodiment described below, the matrix size at step 17 is selected to be $(N1, N2, \ldots, Nn)$ real data values, which are converted by step 21 to the n-dimensional complex matrix size $(N1, N2, \ldots, Nn)$ and so the output of step 23 is an n-dimensional complex matrix with lengths of $(2N1, 2N2, \ldots, 2Nn)$ complex elements (where each complex element has a real and an imaginary component). As a specific example where the number of dimensions n is two, in the case of an input to step 17 of a two-dimensional image with 512 horizontal by 256 vertical real pixels, step 21 generates an output two-dimensional complex matrix of 512 rows by 256 columns. The result of the n-dimensional unitary time frequency anti-aliasing 23 in this case would then be a matrix of 1024×512 complex values.

The output of step 23 is next processed by a unitary n-dimensional orthogonal transform 25. This maps the input n-dimensional data representation of an n-dimensional complex matrix to an output n-dimensional complex matrix in an n-dimensional orthogonal domain. In addition to the n-dimensional input and output domains being mutually orthogonal, each element of the input n-dimensional complex matrix is equivalently represented by n-dimensional basis functions that are orthogonal to each of the other n-dimensional basis functions in that input domain. Symmetrically, each element of the output n-dimensional complex matrix is equivalently represented by n-dimensional basis functions that are orthogonal to each of the other n-dimensional basis functions in that output domain.

While many possibilities exist for the unitary n-dimensional orthogonal transform 25 that meet the criteria specified above, for the purposes of the present embodiment the specific instance of the unitary n-dimensional orthogonal transform will be implemented as a discrete multidimensional Fourier transform for n dimensions. Transforms that may be used in other embodiments include, for example, multidimensional transforms based on prime number theory, Hadamard transforms, Sine, Cosine, Hartley, as well as many potential wavelet transforms.

In the some embodiments for multidimensional real data input the n-dimensional orthogonal transform is a real transformation commonly used for computing a real discrete Fourier transform (real DFT) using a complex discrete Fourier transform (DFT) of length equal to half the real input dimension.

Following the unitary n-dimensional orthogonal transform 25, the n-dimensional probe is now represented by an n-dimensional wavefunction in the form of an n-dimensional complex matrix. For the specific example discussed below for a step 17 input matrix size with lengths in each dimension of (N1, N2, ..., Nn) real data values, this n-dimensional complex matrix contains lengths in each dimension of (2N1, 2N2, ..., 2Nn) complex elements (where each complex element has a real and imaginary component). The n-dimensional probe wavefunction is stored in an n-dimensional matrix storage buffer 27, to retain the probe in memory prior to interference with other wavefunctions from the target (discussed below). For purposes of later reference, this stored wavefunction is designated as φM. The n-dimensional storage buffer 27 may be implemented in memory 204 of computer system 200, or in another storage device. The stored probe wavefunction may serve as a resource that can be reused if multiple n-dimensional interference processes need to use this n-dimensional wavefunction. Such storage of the probe wavefunction often may be more efficient and economical compared to serially repeating the n-dimensional wavefunction preparation process. This intermediate may also be used immediately without storage.

Figure 4A:
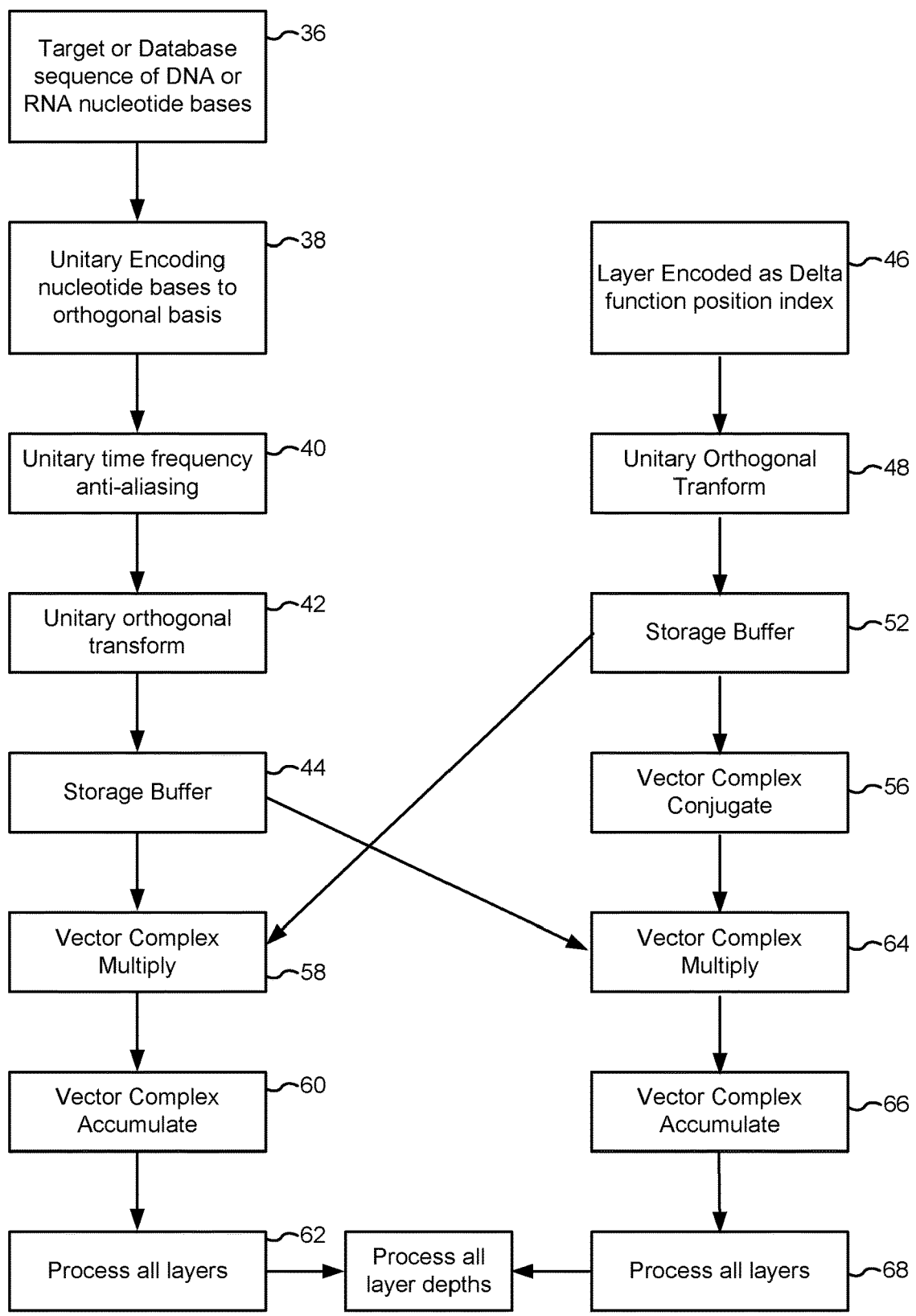
FIG. 4A illustrates the transformation of target sequence to superpositions of wavefunctions and layer encoding for use in sequence searching, in accordance with some embodiments.

FIG. 4A illustrates the transformation of a target sequence (e.g., DNA genome 101) to superpositions of wavefunctions and layer encoding for use in searching the target sequence with a probe. More specifically, FIG. 4A schematically illustrates DNA/RNA target sequence preparation to a wavefunction form and the creation of orthogonal layer encoding superpositions.

Target sequence (sometimes referred to simply as a "target" herein) preparation begins with the input of a target sequence of DNA or RNA nucleotide bases 36. This is typically in the format of a text file, for example a "Fasta" file, where each nucleotide base of DNA or RNA is encoded using the initial letter of the base name.

The next four steps (namely, unitary encoding nucleotide bases to orthogonal basis 38; unitary time frequency anti-aliasing 40; unitary orthogonal transform 42; and storage buffer 44) are similar in functionality to the correspondingly-named steps in method 10 of the probe preparation process described above.

The input sequence 36 is processed by a unitary encoding of nucleotide base sequence to a vector in an orthogonal basis 38. As mentioned above, the input target sequence, which may be millions of bases in length, is typically broken down into smaller frames for processing using the present method. A frame size that is a power of two is typically selected for ease of use with the Fourier transform, but this is not a requirement of the method described herein. In the example discussed below, the target frame size (N) is selected to be 2,048 bases (N=2,048). Other sizes could also be used such as, for example, 4,096 or 8,192 bases. Hundreds and thousands or more of frames may be each processed as described below in order to encode the full length of a given target as superpositions of wavefunctions, for use in searching as described below.

Similarly as described above for probe preparation, this embodiment as applied to a DNA/RNA sequence search achieves an orthogonal and unitary mapping between each of the four nucleotide bases (Adenine, Thymine, Guanine and Cytosine in DNA; and Adenine, Uracil, Guanine and Cytosine in RNA) and the four phase quadrants in a complex number plane.

The output of step 38 is a data representation of a vector of complex numbers. In the embodiment described here, the length of this complex vector is equal to the length in bases of the given input frame from the target nucleotide sequence (e.g., N=2,048 bases). The output of step 38 is then passed to the next step in the process, which is a unitary time frequency anti-aliasing 40. Similarly as for the probe above, this step removes aliasing of position in one orthogonal domain with respect to the other orthogonal domain. Such aliasing may causes ambiguity in the orthogonal transform that violates the unitary (or 1:1 mapping) principle described above. In order to preserve the unitary principle this aliasing must therefore be removed. This may be accomplished by appending to the vector output of step 38 an equal length complex vector comprising zero real and imaginary components. The output of step 40 would therefore be a complex vector at least twice the length of the input target nucleotide sequence. In the example of N=2,048 bases, the output of step 40 is a complex vector having 2N or 4,096 complex elements (where each element has a real and an imaginary component).

The output of step 40 is next processed by unitary orthogonal transform 42. This maps the input data representation of a complex vector to an output complex vector in an orthogonal dimension or domain. In addition to the input and output domains being mutually orthogonal, each element of the input complex vector is equivalently represented by a basis function that is orthogonal to each of the other basis functions in that input domain. Symmetrically, each element of the output complex vector is equivalently represented by a basis function that is orthogonal to each of the other basis functions in that output domain.

While many possibilities exist for the unitary orthogonal transform 42 that meet the criteria specified above, for the purposes of the present embodiment the specific instance of the unitary orthogonal transform will be formalized as a discrete Fourier transform. As previously discussed, other transforms may also be used in other embodiments.

Following the unitary orthogonal transform 42, the target is represented by a wavefunction represented in the form of a complex vector (e.g., with 2N or 4,096 complex elements in this specific example), which may be stored in storage buffer 44. Storage buffer 44 stores this target wavefunction in memory for interference with other wavefunctions as part of encoding and preparing the target for later searching by the probe. Storage buffer may be implemented in memory 204 or in another storage device. The storage serves as a resource if multiple interference processes need to use this target wavefunction, and such storage may be more efficient compared to serially repeating the wavefunction generation process. For purposes of later reference, this intermediate wavefunction stored in storage buffer 44 is designated x. This intermediate wavefunction may also be used immediately, for example in computations executed by processor 201, without storage.

As mentioned more generally above, the target is encoded as one or more superpositions of wavefunctions, and these wavefunctions are encoded with a layer index. The number of layers deep of wavefunctions used in a given superposition may vary, as will be discussed further below. As an example, the superpositions may be formed from 64 wavefunctions each corresponding to a frame from the target, and each of these wavefunctions may be encoded with a layer index, for example, ranging from 0 to 63 (corresponding to a superposition depth of 64 layers). The relationship between layer index and target frames is later discussed in greater detail.

According to the present disclosure, the specific properties of the layer encoding are such that layer encoding is designed to be orthogonal to position encoding. This property is illustrated in the disclosure beginning with steps 46 and 48. The layer index in this specific embodiment is encoded as a delta function position index 46. According to this approach, the position of the delta function along a linear position axis will map unitarily to the layer number that is to be encoded in each one of many potential layer instances. For example, for layer zero, the delta function will be at a position zero.

The delta function position index 46 is provided as an input to step 48, which is a unitary orthogonal transform 48. The delta function for each position corresponding to a layer is converted to a wavefunction using the unitary orthogonal transform. A discrete Fourier transform is used in the DNA sequence example here described, but other transforms may be used in other embodiments, as was mentioned above. The wavefunction in this example is a complex vector having 2N complex elements (e.g., 4,096 complex elements when using a frame size of 2,048 bases). This wavefunction may be stored in storage buffer 52, and for purposes of later reference is designated as $\theta$. The vector complex conjugate of the wavefunction $\theta$ is calculated in step 56, and is designated as $\theta^*$.

Layer encoding may be accomplished by the combining of the two modulation wavefunctions $\theta$ and $\theta^*$ with the target wavefunction $\chi$. The encoding of the target with a wavefunction of a position index and a complex conjugate of that wavefunction assist with the later decoding of the position index when one or more matches are located in a search.

In the case, as here, where the unitary orthogonal transform 48 is the discrete Fourier transform, the two modulation wavefunctions may be represented as vectors equated to roots of unity: $\theta_k = e^{-j2\pi k\Delta/N}$ in the case of the vector in storage buffer 52, and $\theta^* k = e^{j2\pi k\Delta/N}$ in the case of the output of the vector complex conjugate step 56.

Layer encoding of the target wavefunction $\chi$ may be accomplished by the following two operations: (i) a vector complex multiply step 58, which uses the complex vectors stored in storage buffer 44 and storage buffer 52 and performs a vector complex multiply between the two vectors; and (ii) vector complex multiply step 64, which uses the complex vectors stored in storage buffer 44 and the output vector of vector complex conjugate step 56 and performs a vector complex multiply between the two vectors.

The output from steps 58 and 64 will each be a complex vector of 2N complex elements in this embodiment (e.g., 4,096 elements for a frame length N of 2,048 bases). Each complex vector from steps 58 and 64 will correspond to a frame in the original target data, which has been layer encoded as two wavefunctions (from the use of an index and a conjugate of that index).

Each of the many vector outputs of vector complex multiply step 58 then pass to vector complex accumulate step 60. Step 60 calculates a superposition by accumulating several wavefunctions output from step 58. The number of wavefunctions accumulated will depend on the number (i.e., the layer depth) of wavefunctions that will be represented by each superposition output from step 60. In other words, the output of step 60 is a superposition calculated by additively combining multiple wavefunctions output from step 58, where each wavefunction has a different layer encoding, to create a superposition wavefunction ψR in step 62 after all layers have been accumulated. In equation form, $\psi R = \Sigma \chi \cdot \theta$ for all layers that are used to form the superposition (each layer corresponds to a different wavefunction $\chi$ that is output from storage buffer 44 and to an index wavefunction that is output from storage buffer 52).

In a corresponding manner, several output vectors from vector complex multiply step 64 pass to vector complex accumulate step 66, which additively combines multiple wavefunctions output from step 64, each with different layer encoding, to create a superposition wavefunction ψS in step 68 after all layers have been accumulated. In equation form, $\psi S = \Sigma \chi \cdot \theta^*$ for all layers that are used to form the superposition (each layer corresponds to a different wavefunction $\chi$ that is output from storage buffer 44 and to the conjugate of an index wavefunction that is output from step 56).

The encoding method described above is repeated as necessary to process all additional frames of input data from a target or database sequence. As additional frames are processed, additional superposition wavefunctions ψR 62 and ψS 68 will be output. It should be noted that as the target is encoded, that superposition wavefunctions are generally provided as superposition R, S pairs (ψR, ψS). Each superposition ψR, ψS in the example described here has 2N (e.g., 4,096) complex elements.

Steps 60 and 66 are performed to provide potentially very many superposition R, S pairs for a given superposition depth (e.g., a depth of 64 wavefunctions). In step 80, a database may be formed by repeating steps 60 and 66 for other superposition depths (e.g., for layer depths of 32, 16, 8, 4, 2, and 1 wavefunctions).

Also, as an option to the above approach, additional input data frames from the target or database sequence may be processed to extend the length of the output superpositions wavefunctions ψR 62 and ψS 68 instead of only varying the number of layers they contain. As a result, it is possible to create a wide range of output superposition wavefunctions ψR 62 and ψS 68 of various lengths and depths of encoded layers. This flexibility may be used to create multi-resolution wavefunction databases containing a plurality of tracks of varying lengths and depths of encoded layers. The advantage of such a multi-resolution format is that the search process has a range of different superposition depth options in the wavefunction database and may select the most efficient option as appropriate for any given search instance.

The many different possible ways of formatting and combining the output superpositions wavefunctions ψR 62 and ψS 68 so that they may be combined into an encoded target wavefunction database 80 for access during the actual searching process. One specific embodiment of database 80 is the multi-resolution database described below with respect to FIG. 6. The multi-resolution database may comprise numerous superposition R, S pairs (ψR, ψS) grouped into various tracks with each track having a different layer depth. In this embodiment, typically, the maximum useful layer depth has been found to be 128 layers, with 64 layers being more typical. However, other embodiments of the method disclosed herein may possibly use greater layer depths.

Figure 4B:
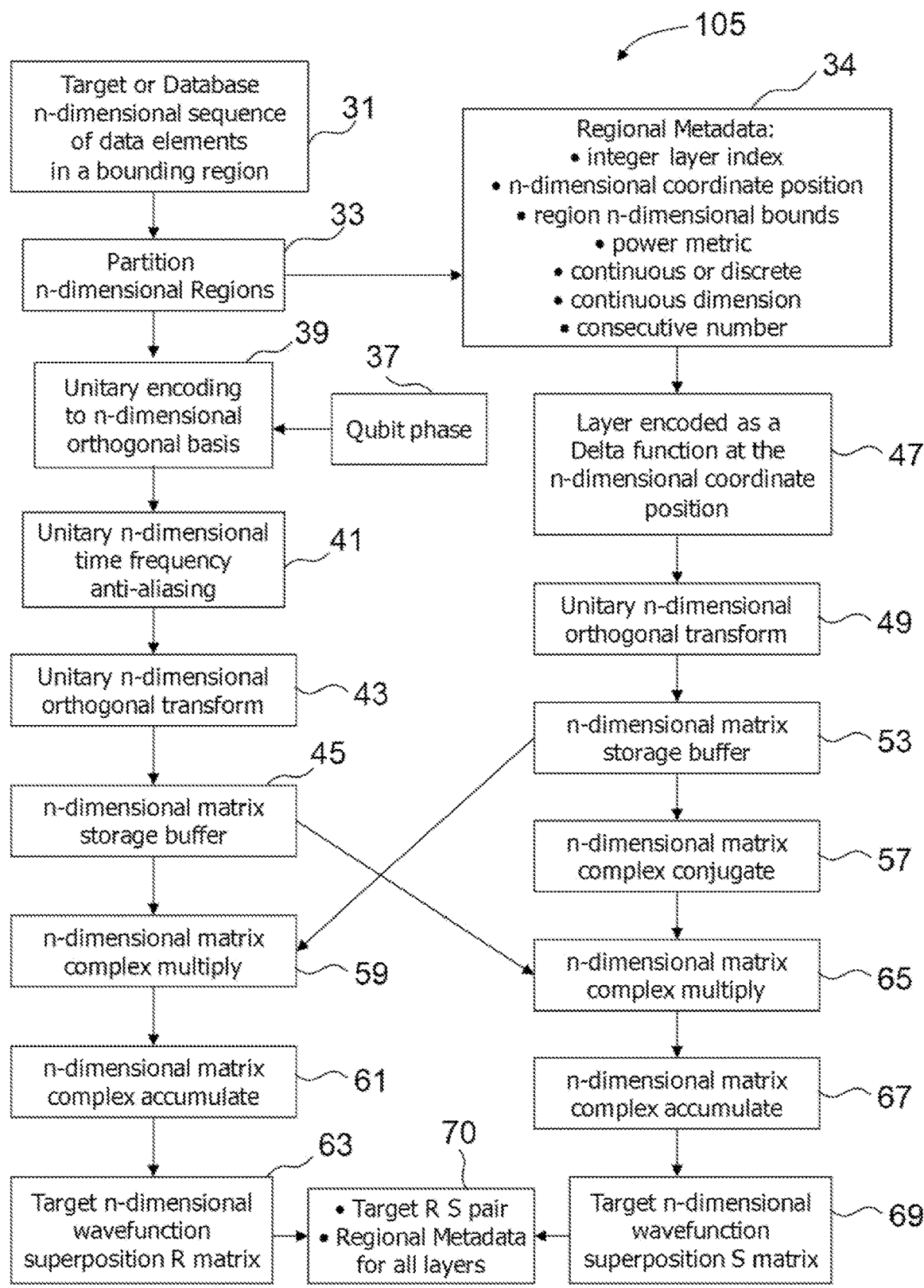
FIG. 4B illustrates the transformation of an n-dimensional target sequence to superpositions of n-dimensional wavefunctions and n-dimensional layer encoding using layer delta functions for use in n-dimensional data sequence searching, in accordance with some embodiments for n-dimensional data sequence searching with either continuous or discrete regions.

FIG. 4B illustrates a method 105 for the transformation of a multidimensional target data sequence to a pair of superpositions of multidimensional wavefunctions for use in multidimensional data sequence searching, where the number of dimensions n is greater than one. The transformation of an n-dimensional target data sequence (e.g., two-dimensional image pixel sequence 71, three-dimensional voxel image sequence 85, or as a general case for any integer number of dimensions, a multidimensional image containing data elements in a multidimensional coordinate grid) to superpositions of n-dimensional wavefunctions and n-dimensional layer encoding for use in searching the n-dimensional target sequence with an n-dimensional probe. More specifically, FIG. 4B schematically illustrates multidimensional target sequence preparation to a multidimensional wavefunction form and the creation of multidimensional orthogonal layer encoding superpositions.

Multidimensional target sequence (sometimes referred to simply as a "target" herein) preparation where the number of dimensions is n begins with the input of an n-dimensional target sequence of data elements 31, for example, two-dimensional pixels, three dimensional voxels or n-dimensional data elements. This is typically in the format of a binary file, for example, in the case of two-dimensional pixels, a "bmp" file, where each pixel is encoded using a single byte representing a value between 0 and 1.0 for the range of values 0 to 255 for each byte.

The n-dimensional target sequence input 31 is next broken into smaller regions by Partition Regions 33. The output of step 33 comprises sections for processing subdivisions of the entire n-dimensional space. Each region output by step 33 is associated with a Regional Metadata 34 which comprises an integer layer index and a corresponding n-dimensional coordinate position that will be used to generate a Layer encoded as a Delta function at the n-dimensional coordinate position 47. A region output by Partition Regions 33 also comprises the region's n-dimensional bounds and a power metric for the data within the region's n-dimensional bounds which are passed to both the Regional Metadata 34 and a unitary encoding to n-dimensional orthogonal basis 39. Partition Regions 33 may sub-divide the input target n-dimensional sequence of data elements 31 according to either a continuous or discrete method and the Regional Metadata will specify which method has been used so that an appropriate sequence searching method may be applied subsequently.

According to the continuous variant of method 105 that prepares target wavefunction superpositions for continuous sequence searching a continuous dimension is defined in Regional Metadata 34. For example, the two-dimensional target image sequence 71 in FIG. 1B, may be sub-divided by Partition Regions 33 to four horizontal rectangular bounding regions where each rectangular bounding region contains a line of alphanumeric characters. Partition Regions 33 may use a continuous method of layer encoding where each integer layer index corresponds to a rectangular bounding region containing a line of alphanumeric characters, for example the region containing the first line of characters may be encoded using integer layer index 1, the region containing the second line of characters may be encoded using integer layer index 2, and so forth. The Regional Metadata 34 created by Partition Regions 33 will specify continuous method encoding with the horizontal dimension as the continuous dimension. Partition Regions 33 will sub-divide each rectangular bounding region containing a line of alphanumeric characters to a series of horizontally adjacent non-overlapping regions that are output to step 39. Each consecutive adjacent non-overlapping region in the continuous dimension is also specified by a consecutive number which may be used to schedule consecutive RS pairs in a continuous n-dimensional sequence searching method. For example, each line may be divided into four horizontally adjacent non-overlapping regions. In this case, each region output to step 39 will have the following components in Regional Metadata 34: an integer layer index; a two-dimensional coordinate position corresponding to the integer layer index; two-dimensional region bounds; a power metric; a continuous method designation; a specified continuous dimension; and a consecutive number.

Continuing the example of FIG. 1B for continuous of layer encoding where each integer layer index corresponds to a rectangular bounding region containing a line of alphanumeric characters, and each line is be divided into four horizontally adjacent non-overlapping regions, Partition Regions 33 executes a pattern that combines the first adjacent non-overlapping regions in each of the four lines as separately encoded layers to an output 70 comprising an R,S pair of wavefunction superpositions with associated Regional Metadata for each of the four separate layers encoded. The method 105 of target preparation will continue in this example with Partition Regions 33 generating the second adjacent non-overlapping regions in each of the four lines that are encoded as separate layers to an second instance of output 70 comprising an R,S pair of wavefunction superpositions with associated Regional Metadata for each of the four separate layers encoded. Similarly, the method 105 of target preparation will continue in this example with Partition Regions 33 generating the third adjacent non-overlapping regions in each of the four lines that are encoded as separate layers to a third instance of output 70, and fourth adjacent non-overlapping regions in each of the four lines that are encoded as separate layers to a fourth instance of output 70, comprising an R, S pair of wavefunction superpositions with associated Regional Metadata for each of the four separate layers encoded.

The output of method 105 comprises a Target R,S pair 70 and the Regional Metadata 34 generated by Partition Regions 33 for all layers encoded in the R and S wavefunction superpositions. Subsequently, an n-dimensional data sequence searching method will be selected according to the Regional Metadata associated with R,S pair. A continuous n-dimensional data sequence searching method will use the Regional Metadata associated with the Target R,S pair 70 to specify the continuous dimension and the consecutive number so that n-dimensional interference outputs may be combined from consecutive R,S pairs. The combination of consecutive n-dimensional interference outputs for the same probe wavefunction allows the probe to be detected equally well when a potential probe match is present in two consecutive regions output form partition Regions 33, for example half in one region and half in the next region, as when it is contained entirely in a single region. In the example described above that divides each horizontal line to four adjacent non-overlapping regions, the continuous method allows each region to be arbitrarily generated, for example the line may be sub-divided into four regions of equal size.

According to the discrete variant of method 105 in FIG. 4B that prepares target wavefunction superpositions for discrete sequence searching Regional Metadata 34 will specify that regions generated by Partition Regions 33 are discrete instead of continuous and in such cases the continuous dimension component of Regional Metadata 34 is not applicable. For example, the two-dimensional target image sequence 71 in FIG. 1B, may be sub-divided by Partition Regions 33 to separate regions each containing a single character. In the case of the alphanumeric text in target image sequence 71 Partition Regions 33 may use a variety of different techniques for sub-dividing the bounding region 77 to smaller bounding regions each comprising a single alphanumeric character, for example the presence of vertical whitespace between horizontal lines of characters combined with horizontal whitespace between consecutive characters in a line may be used to delimit the regions so that each contains a discrete character. In this case, each region output to step 39 will have the following components in Regional Metadata 34: an integer layer index; a two-dimensional coordinate position corresponding to the integer layer index; two-dimensional region bounds; a power metric; a discrete method designation. The two-dimensional coordinate position is unique for each integer layer index since it generates a unique layer delta function and n-dimensional layer modulation wavefunction for the data encoded at that layer. In the methods for searching discrete n-dimensional sequence data a hit is detected at an n-dimensional coordinate position and the layer encoded by that n-dimensional coordinate position has an integer layer index in the Regional Metadata that is associated with the RS wavefunction superpositions where the hit was detected.

According to the discrete variant of method 105 in FIG. 4B that prepares target wavefunction superpositions for discrete sequence searching Regional Metadata 34 will specify that regions generated by Partition Regions 33 have an integer layer index and an n-dimensional coordinate position used to generate the n-dimensional layer modulation wavefunction. In some embodiments the n-dimensional coordinate position may be contained in the bounding region of the output of Partition Regions 33, such as depicted in FIG. 1B for two-dimensional coordinate position 18 and bounding region 15. In such cases the n-dimensional coordinate position represents a physical location in the target data sequence that is functionally analogous to a physical memory address in a conventional computer system. In other embodiments the n-dimensional coordinate position represents a translated location in the target data sequence that is functionally analogous to a virtual memory address in a conventional computer system.

In embodiments where Partition Regions 33 generates n-dimensional coordinate positions that are translated locations of the integer layer index, any arbitrary pattern of translations may be used, for example, selected scaling of the integer to different coordinate dimensions may be used to translate the integer layer index to an n-dimensional coordinate position.

In the some embodiments where Partition Regions 33 generates n-dimensional coordinate positions that are translated locations, the translation of integer layer index to n-dimensional coordinate positions in Regional Metadata 34 generates a series of unique n-dimensional coordinate positions from the one-dimensional integer layer index by using a combination of a zigzag scan pattern that works by filling an n-dimensional coordinate grid diagonally across the n-dimensional space outwards from the origin, combined with a scaled bit-reversed coordinate transformation comprising bit-reversal of each coordinate of the n-dimensional zigzag generated position coordinates, followed by a scaling of the bit-reversed coordinates. The resulting spatial transformation maps the locally grouped n-dimensional zigzag scan coordinates to a set of n-dimensional coordinate positions at the centers of n-dimensional regions. The n-dimensional coordinate positions are maximally spatially separated and each region has a length in each dimension determined by the scale factor applied to that dimension's coordinate. Spatial separation of the n-dimensional coordinates used to encode distinct layers in the RS pair in this way provides an optimally distributed pattern to maintain layer signal separation in the RS pair wavefunction superposition layer space while also providing a virtual address space in one-dimension addressable with the integer layer index.

The multidimensional target sequence input 31 is decomposed to sections by Partition Regions 33 by subdividing the target bounding region (e.g., bounding region 77 in FIG. 1B, bounding region 92 in FIG. 1C) to smaller separate bounding regions each comprising one section of output from step 33. In some embodiments the Partition Regions 33 also calculates the power metric in the output section equal to the sum of the squared data values inside the n-dimensional bounding region of the section. The complete n-dimensional section comprising the partitioned section of the n-dimensional target sequence 31 defined by the section bounding region, the n-dimensional grid data values and their total power metric, is passed to step 39 for unitary encoding to n-dimensional orthogonal basis.

The next four steps (namely, unitary encoding to n-dimensional orthogonal basis 39; unitary n-dimensional time frequency anti-aliasing 41; unitary n-dimensional orthogonal transform 43; and n-dimensional matrix storage buffer 45) are similar in functionality to the correspondingly-named steps in method 103 of the multidimensional probe data preparation process described above.

The n-dimensional input sequence section from step 33 is processed by a unitary encoding of n-dimensional data sequence to an n-dimensional matrix in an n-dimensional orthogonal basis 39. As mentioned above, the input multidimensional target sequence 31, which may be millions of pixels or voxels in length, is broken down into smaller sections for processing using Partition Regions step 33 in the present method. A section size that is a power of two is typically selected for ease of use with the Fourier transform, but this is not a requirement of the method described herein. In the example discussed below, the target section size is selected to be 512×256 pixels. Other sizes could also be used such as, for example, 4096×2048 pixels. Hundreds and thousands or more of sections may be each processed as described below in order to encode the full length of a given target as superpositions of wavefunctions, for use in searching as described below.

The unitary encoding to n-dimensional orthogonal basis 39 may receive an additional input of a qubit phase search parameter 37 that is obtained for the input target sequence 31. The qubit phase 37 may be represented as a complex value that determines the selections in a circular space comprising the complex phase of individual layers in the wavefunction superposition RS pair. The circular phase may be used as an extra dimension in computations that is either a discrete or continuous variable. In the discrete variable case the circular space may be divided for example into four orthogonal spaces each comprised of a quadrant in the range plus or minus 45° with respect to each positive and negative real and imaginary axis of the unit circle in the complex plane. In the continuous variable case the circular space may for example represent direction in space or distance between two locations inside a loop.

Similarly as described above for multidimensional image probe preparation, this embodiment as applied to a two-dimensional image pixel sequence searching, three-dimensional voxel image searching and any multidimensional data searching, achieves an orthogonal and unitary mapping between the real or complex data values at each pixel, voxel or multidimensional data element, which may be for example a color, density, reflectiveness attribute, and a matrix of complex numbers, where the matrix has number of dimensions equal to the number of dimensions n in the multidimensional input sequence 31. The qubit phase 37, represented as a complex value, may be applied to the real or complex data values at each pixel, voxel or multidimensional volumetric element using complex multiplication to generate the output of step 39.

The output of step 39 is a data representation of an n-dimensional matrix of complex numbers. In the embodiment described here, the size of this complex matrix is equal to the dimensions of data value elements of the given input section from the target n-dimensional data sequence (e.g., lengths in each dimensions of (N1, . . . , Nn) for the general preferred embodiment in n dimensions and 512×256 pixels for the specific two-dimensional example described herein). The output of step 39 is then passed to the next step in the process, which is an n-dimensional unitary time frequency anti-aliasing 41. Similarly as for the probe above, this step removes aliasing of position in one multidimensional orthogonal domain with respect to the other multidimensional orthogonal domain. Such aliasing may causes ambiguity in the multidimensional orthogonal transform that violates the unitary (or 1:1 mapping) principle described above. In order to preserve the unitary principle this aliasing must therefore be removed. This may be accomplished by appending to the matrix output of step 39 in each dimension of the matrix an equal sized n-dimensional complex matrix comprising zero real and imaginary components. The output of step 41 would therefore be an n-dimensional complex matrix at least twice the size of the input n-dimensional target data sequence in each dimension. For the n-dimensional data searching exemplary case discussed herein the input complex matrix size (N1, N2, . . . , Nn) will generate an output complex matrix with lengths in each dimension of (2N1, 2N2, . . . , 2Nn). In the example of 512×256 pixels, the output of step 41 is a complex matrix having 1024×512 complex elements (where each element has a real and an imaginary component). As a specific example where the number of dimensions n is two, in the case of an input to step 31 of a two-dimensional image with 512 horizontal by 256 vertical real pixels, step 39 generates an output two-dimensional complex matrix of 256 rows by 512 columns. The result of the n-dimensional unitary time frequency anti-aliasing 41 in this case would then be a matrix of 512×1024 complex values.

The output of step 41 is next processed by unitary n-dimensional orthogonal transform 43. This maps the input n-dimensional data representation of a complex matrix to an output n-dimensional complex matrix in an n-dimensional orthogonal domain. In addition to the n-dimensional input and output domains being mutually orthogonal, each element of the input n-dimensional complex matrix is equivalently represented by n-dimensional basis functions that are orthogonal to each of the other n-dimensional basis functions in that input domain. Symmetrically, each element of the output n-dimensional complex matrix is equivalently represented by n-dimensional basis functions that are orthogonal to each of the other n-dimensional basis functions in that output domain.

While many possibilities exist for the unitary n-dimensional orthogonal transform 43 that meet the criteria specified above, for the purposes of the present embodiment the specific instance of the unitary n-dimensional orthogonal transform will be formalized as a discrete multidimensional Fourier transform for n dimensions. As previously discussed, other multidimensional transforms may also be used in other embodiments.

In the some embodiments for multidimensional real data input the n-dimensional orthogonal transform is a real transformation commonly used for computing a real discrete Fourier transform (real DFT) using a complex discrete Fourier transform (DFT) of length equal to half the real input dimension.

Following the unitary n-dimensional orthogonal transform 43, the target is represented by an n-dimensional wavefunction represented in the form of a n-dimensional complex matrix (e.g., with lengths in each dimension of (2N1, 2N2, . . . 2Nn) complex elements in this specific example), which may be stored in n-dimensional matrix storage buffer 45. The n-dimensional storage buffer 45 stores this n-dimensional target wavefunction in memory for n-dimensional interference with other n-dimensional wavefunctions as part of encoding and preparing the target for later n-dimensional searching by the n-dimensional probe. The n-dimensional storage buffer 45 may be implemented in memory 204 or in another storage device. The storage serves as a resource if multiple n-dimensional interference processes need to use this n-dimensional target wavefunction, and such storage may be more efficient compared to serially repeating the n-dimensional wavefunction generation process. For purposes of later reference, this n-dimensional intermediate wavefunction stored in n-dimensional storage buffer 45 is designated $\chi M$. This n-dimensional intermediate wavefunction may also be used immediately, for example in computations executed by processor 201, without storage.

As mentioned more generally above, the multidimensional target is encoded as one or more superpositions of multidimensional wavefunctions, and these multidimensional wavefunctions are encoded with an integer layer index. The number of layers deep of wavefunctions used in a given superposition may vary, as will be discussed further below. As an example, the multidimensional superpositions may be formed from 64 multidimensional wavefunctions each corresponding to a section from the multidimensional target, and each of these multidimensional wavefunctions may be encoded with an integer layer index, for example, ranging from 0 to 63 (corresponding to a superposition depth of 64 layers). The relationship between layer index and target sections is later discussed in greater detail.

According to the present disclosure, the specific properties of the layer encoding are such that layer encoding is designed to be orthogonal to position encoding. This property is illustrated in the disclosure beginning with steps 34 and 47. The integer layer index in this specific embodiment and an n-dimensional coordinate position are output by Partition Regions 33 to Regional Metadata 34 for a corresponding region output from Partition Regions step 33 to step 39. As described above, any arbitrary pattern of translations such as selected scaling of the integer to different coordinate dimensions may be used to translate the integer layer index to an n-dimensional coordinate position. The output of step 33 is an n-dimensional coordinate position that is encoded as a layer delta function in step 47. The layer delta function is defined as a null valued n-dimensional range with a single coordinate grid position having a non-zero value. According to this approach, the n-dimensional coordinate position of the delta function will map unitarily to the integer layer index number that is to be encoded in each one of many potential layer instances. For example, for layer zero, the delta function may be at n n-dimensional coordinate position with zero coordinates (0, . . . , 0) known as the origin in any multidimensional coordinate space. In Regional Metadata 34 each integer layer index corresponds to a different n-dimensional coordinate position which will generate a unique layer delta function for the integer layer index in step 47.

Step 47 uses the n-dimensional coordinate position from Regional Metadata 34 to generate a layer delta function comprising a null valued range with a single non-zero real value at the n-dimensional grid position specified by the n-dimensional coordinates.

The output of step 47 is an n-dimensional complex matrix with a single n-dimensional coordinate position having a non-zero value. In some embodiments of n-dimensional data sequence searching method the complex number value at the single n-dimensional coordinate position having a non-zero value will have a real component of unity and an imaginary component value of zero.

The real valued delta function at the n-dimensional coordinate position 47 is provided as an n-dimension complex matrix comprising a single non-zero value as input to step 49, which is a unitary n-dimensional orthogonal transform 49. The delta function for each n-dimensional coordinate position corresponding to an integer layer index is converted to an n-dimensional wavefunction using the unitary n-dimensional orthogonal transform 49. A discrete multidimensional Fourier transform of n dimensions is used as the unitary n-dimensional orthogonal transform in the multidimensional data sequence searching example here described, but other transforms may be used in other embodiments, as was mentioned above. The n-dimensional wavefunction in this example is a complex matrix having lengths in each dimension of (2N1, 2N2, . . . , 2Nn) complex elements (e.g., 1024×512 complex elements when using a two-dimensional image size of 512×256 pixels). This n-dimensional wavefunction may be stored in n-dimensional matrix storage buffer 53, and for purposes of later reference is designated as θM. The n-dimensional matrix complex conjugate of the n-dimensional wavefunction θM is calculated in step 57, and is designated as θM*.

Layer encoding may be accomplished by the combining of the two n-dimensional modulation wavefunctions θM and θM* with the n-dimensional target wavefunction χM. The encoding of the target with a n-dimensional wavefunction of a n-dimensional coordinate position and a complex conjugate of that n-dimensional wavefunction assist with the later decoding of the n-dimensional coordinate position and the corresponding integer layer index when one or more matches are located in a search.

In the case, as here, where the n-dimensional unitary orthogonal transform 49 is the discrete n-dimensional Fourier transform, the two n-dimensional modulation wavefunctions may be represented as matrices equated to complex roots of unity: such as $\theta M_{(p,q)} = e^{-j2\pi p \Delta x/Nx} \cdot e^{-j2\pi q \Delta y/Ny} = e^{-j2\pi(p\Delta x/Nx + q\Delta y/Ny)}$ in the case of n the number of dimension is two and the two-dimensional coordinates of the delta function are $(\Delta x, \Delta y)$, represented as a matrix in n-dimensional matrix storage buffer 53, and $\theta M^*_{(p,q)} = e^{j2\pi p \Delta x/Nx} \cdot e^{j2\pi q \Delta y/Ny} = e^{j2\pi(p\Delta x/Nx + q\Delta y/Ny)}$ in the case of the corresponding output of the n-dimensional matrix complex conjugate step 57, where each is defined over the two-dimensional grid $0 \le p \le N1-1, \ldots, 0 \le q \le Nn-1$.

The n-dimensional wavefunction in storage buffer 53 and the n-dimensional wavefunction in storage buffer 65 can be represented for the general n-dimensional case where the n-dimensional coordinates of the delta function are $g((\Delta 1, \ldots, \Delta n)$ defined over the n-dimensional grid $0 \le \Delta 1 \le N1-1, \ldots, 0 \le \Delta n \le Nn-1$, where N1 is the number of grid points in dimension 1 and Nn is the number of grid points in dimension n. In other words, $g(\Delta 1, \ldots, \Delta n)$ is a real data value of unity at the n-dimensional coordinates of $(\Delta 1, \ldots, \Delta n)$, where the elision marks between $\Delta 1$ and $\Delta n$ denote coordinates in all the dimension between the first and last dimension. Accordingly, the n-dimensional wavefunction in storage buffer 53 is represented as $\theta M_{(k1,k2,\ldots,kn)} = e^{-j2\pi k1\Delta 1/N1} \cdot e^{-j2\pi k2\Delta 2/N2}, \ldots, e^{-j2\pi kn\Delta n/Nn} = e^{-j2\pi(k1\Delta 1/N1 + k2\Delta 2/N2+, \ldots, kn\Delta n/N)}$, and the n-dimensional wavefunction output by n-dimensional matrix complex conjugate step 57 is represented as $\theta M^*_{(k1,k2,\ldots,kn)} = e^{j2\pi k1\Delta 1/N1} \cdot e^{j2\pi k2\Delta 2/N2}, \ldots, e^{j2\pi kn\Delta n/Nn} = e^{j2\pi(k1\Delta 1/N1+k2\Delta 2/N2+,\ldots, kn\Delta n/N)}$, where each is defined over the n-dimensional grid $0 \le k1 \le N1-1, \ldots, 0 \le kn \le Nn-1$.

Layer encoding of the target wavefunction χM may be accomplished by the following two operations: (i) an n-dimensional matrix complex multiply step 59, which uses the n-dimension complex matrices stored in storage buffer 45 and storage buffer 53 and performs an n-dimensional matrix complex multiply between the two n-dimensional matrices; and (ii) n-dimensional matrix complex multiply step 65, which uses the n-dimensional complex matrices stored in storage buffer 45 and the output n-dimensional matrix of n-dimensional matrix complex conjugate step 57 and performs an n-dimensional matrix complex multiply between the two n-dimensional matrices. The n-dimensional matrix complex multiply operation is defined herein as a complex multiplication between values at corresponding coordinates.

The output from steps 59 and 65 will each be an n-dimensional complex matrix with lengths in each dimension of (2N1, 2N2, . . . , 2Nn) complex elements in the preferred n-dimensional data searching embodiment, or for the specific example where the number of dimensions is equal to two (e.g., 2N1×2N2=1024×512 complex elements, for a two-dimensional image dimensions of 512×256 pixel data elements where N1=512 and N2=256). Each n-dimensional complex matrix from steps 59 and 65 will correspond to a region output by Partition Regions 33 comprising a subdivided section of input n-dimensional sequence 31 in the original target data, which has been layer encoded as two n-dimensional wavefunctions (from the use of an integer layer index corresponding to a positive n-dimensional coordinate position and a conjugate position of that integer layer index corresponding to an n-dimensional coordinate position with indices that are negated values of each of the coordinates of the positive position). The n-dimensional coordinate position designated as positive is arbitrary an may include negate or wrap-around coordinate indices in each of the n dimensions. In other words, for the same integer layer index, the n-dimensional coordinate position designated as positive has a conjugate position that is a reflection in the n-dimensional origin of the n-dimensional coordinate position designated as positive.

Each of the many n-dimensional matrix outputs of n-dimensional matrix complex multiply step 59 then pass to n-dimensional matrix complex accumulate step 61. Step 61 calculates an n-dimensional superposition by accumulating several n-dimensional wavefunctions output from step 59. The number of n-dimensional wavefunctions accumulated will depend on the number (i.e., the layer depth) of n-dimensional wavefunctions that will be represented by each n-dimensional wavefunction superposition output from step 61. In other words, the output of step 61 is a target n-dimensional wavefunction superposition R 63, calculated by additively combining multiple n-dimensional wavefunctions output from step 59, where each wavefunction has a different layer encoding, to create a target n-dimensional wavefunction superposition ψRM in step 63 after all layers have been accumulated. In equation form, $\psi RM = \Sigma \chi M \cdot \theta M$ for all layers that are used to form the n-dimensional superposition (each layer corresponds to a different n-dimensional wavefunction χM that is output from n-dimensional storage buffer 45 and to the R differential n-dimensional layer modulation wavefunction θM (generated from an n-dimensional layer delta function coordinate position) that is output from multidimensional storage buffer 53).

In a corresponding manner, several output n-dimensional matrices from n-dimensional matrix complex multiply step 65 pass to n-dimensional matrix complex accumulate step 67, which additively combines multiple n-dimensional wavefunctions output from step 65, each with different layer encoding, to create an n-dimensional wavefunction superposition ψSM in step 69 after all layers have been accumulated. In equation form, ψSM=ΣχM·θM* for all layers that are used to form the n-dimensional superposition (each layer corresponds to a different n-dimensional wavefunction χM that is output from n-dimensional storage buffer 45 and to the S differential n-dimensional layer modulation wavefunction 57 designated θM* that is the complex conjugate of the n-dimensional coordinate position layer modulation wavefunction θM that is output from step 53).

The encoding method described above is repeated as necessary to process all additional subdivisions of multidimensional input data from a target or database sequence. As additional groups of multiple input sections comprising n-dimensional bounded regions inside an input target n-dimensional sequence 31 are processed, additional superposition wavefunctions ψRM 63 and ψSM 69 will be output. It should be noted that as the target is encoded, that superposition wavefunctions are generally provided as n-dimensional superposition R, S pairs (ψRM, ψSM) and their associated Regional Metadata 34 for all layers. Each superposition ψRM, ψSM in the example described here may be represented as an n-dimensional matrix with lengths in each dimension of (2N1, 2N2, . . . , 2Nn) complex elements. The Regional Metadata for each R,S pair 70 includes the Regional Metadata 34 for each layer that has been encoded in the R,S pair. According to the present disclosure each integer layer index is unique for each layer contained in R,S pair 70 and is uniquely associated with an n-dimensional coordinate position, n-dimensional bounds of the region and a power metric of the data elements contained inside the bounded n-dimensional region. The Regional Metadata 34 associated with each R,S pair 70 includes applicable parameters that were employed by Partition Regions 33 to generate the layer encoded sub-divided section of the input target or database n-dimensional sequence of data elements. In the case that Partition Regions 33 generated consecutive regions by stepping in a selected continuous dimension the Regional Metadata 34 comprises the specification of continuous encoding, the continuous dimension for the step and a consecutive number for scheduling consecutive R,S pairs in the continuous method. For example, the two-dimensional target image 71 of FIG. 1B may be sub-divided by Partition Regions 33 to four horizontal rectangular bounding regions where each rectangular bounding region contains a line of alphanumeric characters. The Regional Metadata 34 created by Partition Regions 33 will specify continuous method encoding with the horizontal dimension as the continuous dimension. Partition Regions 33 will sub-divide the rectangular bounding region containing a line of alphanumeric characters to horizontally adjacent non-overlapping regions that are output to step 39 each with a consecutive number in the Regional Metadata 34. A subsequent n-dimensional data sequence searching method will be selected according to the Regional Metadata associated with the R,S pair. A continuous n-dimensional data sequence searching method will use the Regional Metadata associated with the R,S pair to specify the continuous dimension so that n-dimensional interference outputs may be combined from consecutive R,S pairs having consecutive numbers in the associated Regional Metadata. The combination of consecutive n-dimensional interference outputs for the same probe wavefunction allows the probe to be detected equally well when a potential probe match is present in two consecutive regions output form partition Regions 33, for example half in one region and half in the next region, compared to when it is contained entirely in a single region.

Steps 61 and 67 are performed to provide potentially very many n-dimensional superposition R, S pairs 70 for a given superposition depth (e.g., a depth of 64 wavefunctions). Also, as an option to the above approach, additional input data sections as regions from the target or database sequence may be processed to extend the length of the output n-dimensional superpositions wavefunctions ψRM 63 and ψSM 69 instead of only varying the number of layers they contain. As a result, it is possible to create a wide range of output n-dimensional superposition wavefunctions ψRM 63 and ψSM 69 of various lengths and depths of encoded layers.

Figure 5A:
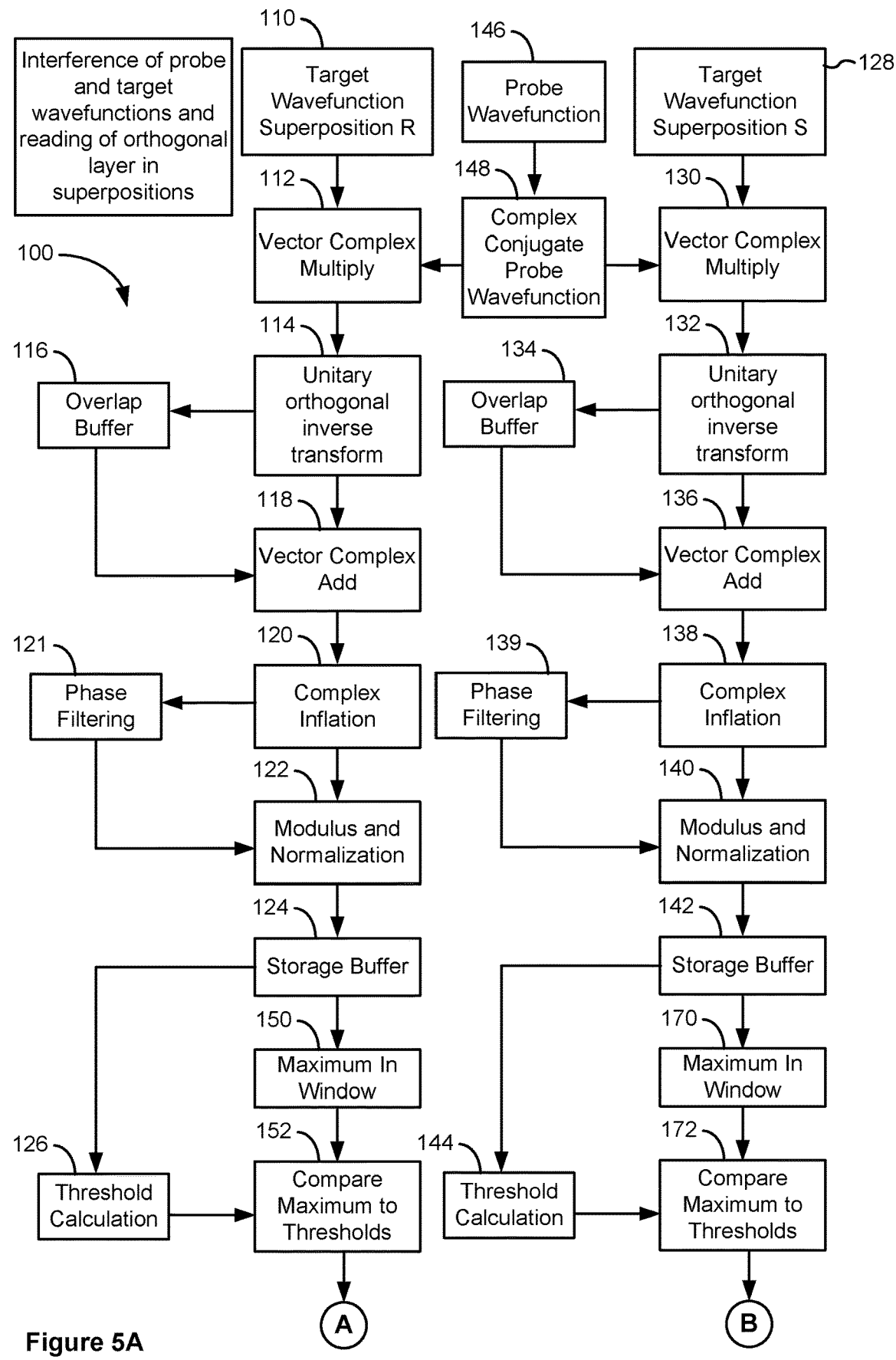
FIGS. 5A-5B illustrate a flowchart for a method of sequence searching, using interference between the probe and target wavefunctions prepared by the methods of FIGS. 3A and 4A and the assessment of hits that are located, in accordance with some embodiments.
Figure 5B:
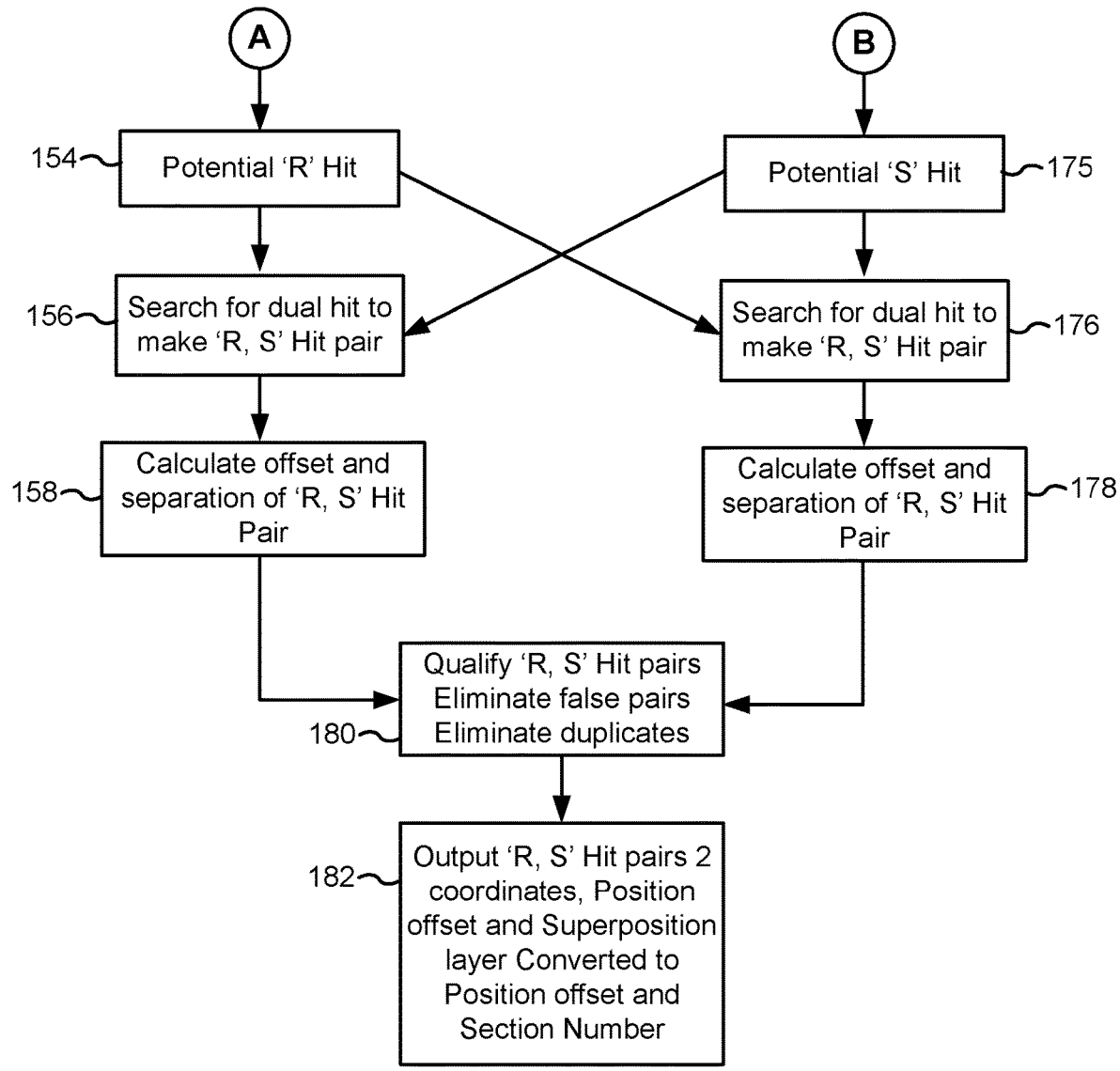

FIGS. 5A-5B illustrate a sequence searching method 100, using interference between the probe and target wavefunctions prepared by the methods of FIGS. 3A and 4A and including the assessment of hits that are located. More specifically, method 100 involves the search for and detection of any pattern matches in the target wavefunction superpositions and the reading of the position offset plus the layer index of any detected matches.

According to the present disclosure, the pattern matching search process performs an interference between the probe wavefunction and one or more superpositions of target wavefunctions that have been modulated according to their particular layer index, as was discussed above. In the diagram of method 100, two separate superposition wavefunctions are input: target wavefunction superposition R 110 and target wavefunction superposition S 128. Superpositions 110 and 128 may be a superposition R, S pair (ψR, ψS) to be processed next from among the many such R, S pairs that correspond to a given track (the preparation of which was discussed above).

Method 100 illustrates the parallel searching of many such corresponding superposition R, S pairs. The given track has been selected, for example, from the multi-resolution database for performing a search. Criteria that may be used for selecting the track to use are discussed later below.

The input probe wavefunction φ 146 is prepared by method 10 of FIG. 3A. The complex conjugate of φ is calculated in step 148 and is designated φ*. The complex conjugate φ* is then interfered separately with each of ψR and ψS by performing a vector complex multiply operation in each of steps 112 and 130, respectively. The output from each step 112 and 120 is a complex vector having 2N or 4,096 complex elements in the specific example of an input frame length of N or 2,048 bases.

The outputs of vector complex multiply steps 112 and 130 are next each processed with a unitary orthogonal inverse transform in steps 114 and 132, respectively. These inverse transforms are the inverse of the transform that was previously used to prepare the probe and target wavefunctions above. While many possibilities exist for the unitary orthogonal inverse transforms 114 and 132 as mentioned earlier, for the purposes of the present embodiment the unitary orthogonal transform will be an inverse discrete Fourier transform.

As will be next discussed, overlapping portions selected from the incoming inverse transform vector outputs from steps 114 and 132 will be separately added to overlap buffer 116 and overlap buffer 134 respectively, to provide vector complex addition results at each of steps 118 and 136. These results are designated for later reference as $VCA_R$ and $VCA_S$, respectively. After the processing described below, each of the vector results $VCA_R$ and $VCA_S$ will be a complex vector of length N or 2,048 complex elements for the exemplary input target frame size of N or 2,048 bases. It should be noted that a benefit of the overlapping of successive frames is to create $VCA_R$ and $VCA_S$ data that is independent of the probe sequence occurrences in the target sequence, even when the probe sequence is contained in two separate but consecutive wavefunction frames input to steps 110 and 128.

More specifically, each of the complex vectors output from step 114 (each such complex vector is designated as "frame h" for purposes of discussion) is processed to overlap a portion of a given frame h with a portion of its predecessor frame using an overlap buffer 116 and a vector complex add operation at step 118. For discussion purposes, each predecessor and successor complex vector output from step 114 is designated as "frame h−1" and "frame h+1", respectively. For the example of an initial input target frame length of N or 2,048 bases, each frame h contains 2N or 4,096 elements. For purposes of discussion, the elements for frame h may be considered as divided into a first half of elements 0 to N−1, and a second half of elements N to 2N−1 (each half contains N elements). For each frame output from step 114, the vector elements 0 to N−1 from the first half of the frame are stored in an overlap buffer at step 116. Overlap buffers 116 and 134 may be any suitable form of memory or other storage.

Next, in step 118 each of vector elements N to 2N−1 in the second half of a new frame h output from step 114 is added using vector complex add step 118 to the corresponding elements 0 to N−1 in the first half of the preceding output frame h−1, which was previously stored in overlap buffer 116. In other words, element 0 is added to element N, element 1 is added to element N+1, and so forth, and element N−1 is added to element 2N−1. The output from step 118 ($VCA_R$) is a set of N complex correlations 0 to N−1 for each incoming frame h. The total number of vectors $VCA_R$ output from step 118 is one for each frame input in steps 110 and 128. During loop processing, the total number of vectors $VCA_R$ output from step 118 is equal to the number of wavefunction superposition frames input in steps 110 and 128.

The first half (elements 0 to N−1) of the same new output frame h from the inverse transform 114 is stored in overlap buffer 116 until it is brought together with the second half (elements N to 2N−1) of the next output frame h+1 from inverse transform 114. As a result of this repeated overlap and vector addition processing, vector complex add 118 outputs a vector $VCA_R$ with a length that is half that of the output vectors from inverse transform 114.

In a similar manner to that described immediately above, each of many complex vector outputs from inverse transform step 132 is processed to overlap each frame with its predecessor and successor frames using overlap buffer 134 and vector complex add 136. As a result of this repeated overlap and vector addition process, vector complex add 136 outputs a vector $VCA_S$ with a length that is half that of the output vectors from inverse transform 132. The output from step 136 ($VCA_S$) is a set of N complex correlations 0 to N−1 for each incoming frame h.

The next steps involve processing the output vector $VCA_R$ of vector complex add step 118 via a complex inflation step 120, and processing the output vector $VCA_S$ of vector complex add step 136 via a complex inflation step 138. For each complex inflation step 120 and 138, each element of the vector $VCA_R$ and $VCA_S$, respectively, is raised to the third power using vector complex multiplication. In other embodiments, it should be noted that other powers or other manners of inflation may used. Complex inflation may assist in separating background noise in vectors $VCA_R$ and $VCA_S$ from peak signals therein that correspond to potential matches between the probe and the target database.

The outputs from complex inflation steps 120 and 138 may be processed using optional phase filtering steps 121 and 139. Typically, this is designed to select direct correlates and exclude phase rotated correlates since these are of greater interest in representing a pattern match. The outputs from this phase filtering are provided to modulus and normalization steps 122 and 140, respectively. Each of these steps 121 and 139 involves phase scaling by multiplying each complex element of each of the inflated vectors by a phase scale factor. The phase scale factor may be determined by the phase of the complex element. For example, the phase scale factor F may be cosine (arctangent (imaginary/real)) for the interval where real is positive. In the case where the real is less than or equal to zero, the phase scale factor F is zero. The phase filtered complex value output is (F*real, F*imag). The phase scaling may eliminate correlations that are out of phase. For example, there may be a match that is not a direct phase match to a probe, but instead is a rotation of that phase (e.g., the same sequence rotated by 90°).

The two parallel processing paths continue with the providing of the output of complex inflation step 120 to modulus and normalization step 122, and providing of the output of complex inflation step 138 to modulus and normalization step 140. Each of the modulus and normalization steps 122 and 140 involves calculation of the real modulus of each input complex element followed by a multiplication by a normalization scale factor that is constant for all elements in the input vector to step 122 or 140. The normalization scale factor may be determined using the theoretical maximum correlation value corresponding to the vector outputs from steps 114 and 132. The normalization scale factor may be calculated as the desired output peak height divided by a total input energy calculated according to the energy in the encoding of a single base, squared to reflect 100% correlation, times the number of bases raised to the third power to account for inflation, times the gain of the unitary orthogonal transform, times the gain of the unitary orthogonal inverse transform. In the case where each base is encoded by a complex value of magnitude 1,000, and using discrete Fourier transforms of 4,096 complex values, for a normalized peak of 687 the scale factor is $1e^{26}$. One aspect of the foregoing is that the normalization scale factor may be proportional to the reciprocal of the cube of the count of effective bases in the probe.

The output of each step 122 and 140 is a vector of scalar numbers (each vector is designated as $RV_R$ and $RV_S$, respectively) representing the scaled magnitude of the corresponding input complex vector elements. For example, for an exemplary input frame length of N or 2,048 bases, $RV_R$ and $RV_S$ contain N or 2,048 real numbers. Each of the vectors $RV_R$ and $RV_S$ is a correlation at a particular base position between the probe sequence and the target sequence. It should be noted that this correlation may be measured at every base position in the target sequence.

The outputs of steps 122 and 140 may be temporarily saved to storage buffers 124 and 142, respectively. These storage buffers may be used to hold these normalized results of the superposition R and S wavefunction interferences with the probe wavefunction so that the results may be further analyzed to determine if any hits or significant similarities are present. In this specific context, a "hit" refers to a peak value in the normalized data output from step 122 or 140.

In typical use, there is a stream of real vectors $RV_R$ and $RV_S$, with corresponding $RV_R$ and $RV_S$ vectors stored in storage buffer 124 or 142 for each superposition wavefunction R, S pair ($\psi R$, $\psi S$) that entered method 100 at steps 110 and 128. The number of $RV_R$, $RV_S$ vector pairs will depend, for example, on the resolution track from the multi-resolution database that was selected for searching. The real vectors typically abut one another directly (i.e., this process is like the assembly of one long real vector, with a length depending, for example, the number of layers being processed in parallel). The $RV_R$ and $RV_S$ vectors are examined for peaks that correspond to high correlations between the probe and the target.

Hit Detection Process

In an attempt to capture all potentially significant matches between the probe and target sequences, the hit detection process described below contains several steps. These steps are designed to identify all potential candidates, then to perform a more rigorous qualification of these candidates to attempt to eliminate false detection events. The hit detection process outputs qualified events comprising a pair of hits, one each from the parallel R and S wavefunction interference processing paths described above. However, as part of the hit detection process, the real vectors $RV_R$ and $RV_S$ are initially each screened for hits independently. This approach improves the likelihood that all significant matches between the probe and target sequences will be found since two detection opportunities are thus created for each potential match.

The hit detection process begins with a threshold calculation at step 126, which is applied to data from real vector $RV_R$ obtained from storage buffer 124 and a threshold calculation at step 144, which is applied to data from real vector $RV_S$ obtained from storage buffer 142. In each case, the normalized magnitude data are analyzed using statistical methods to calculate the mean and standard deviation of each set of data. In threshold calculation 126 two threshold values are calculated for the R wavefunction interference data, and in threshold calculation 144 two thresholds are calculated for the S wavefunction interference data.

Each pair of thresholds consists of a primary threshold and a secondary threshold, with the primary threshold being greater than the corresponding secondary threshold. These thresholds are calculated by adding the mean value to a multiple of the standard deviation value of the respective data set. For example, the multiples may be sixteen times in the case of the primary threshold and six times in the case of the secondary threshold. For the primary threshold a larger multiple is applied to the standard deviation value, and for the secondary threshold a smaller multiple is applied to the standard deviation value. In addition, a tertiary threshold is calculated for each data set using the combined means from steps 126 and 144 plus a multiple of the combined standard deviations from steps 126 and 144. This multiple is, for example, sixteen times the combined standard deviations. The tertiary threshold is used to test the combined maximum values in a pair of R, S hits. The use of the primary, secondary and tertiary thresholds is described below.

The next steps in the detection process are the determination of a maximum in a window in a step 150, which is applied to the data from the R wavefunction interference in storage buffer 124, and a maximum in a window in a step 170, which is applied to the data from the S wavefunction interference in storage buffer 142. The window length is in each case equal to the effective length of the probe sequence, where the effective length refers to the number of coding bases in the probe sequence, (but not counting gaps or bases with a zero input weighting—for example, a value $\gamma k$ of zero as discussed below). Using a window size determined in this manner attempts to account for a hypothetical worst case scenario in which the probe sequence repeats itself as two adjacent sequences in the overall target sequence.

The window is advanced across the full length of each real vector $RV_R$ and $RV_S$. The window is advanced, after each selection of a maximum value, by a number of index positions in vector $RV_R$ or $RV_S$ equal to the total window length so that no given sequence position of the real vector is examined in step 150 more than once. A maximum value is selected from within the window for each vector $RV_R$ or $RV_S$ at each position in its advance along the corresponding vector.

The output of maximum in window step 150 is the index position (selected from positions 0 to N−1 in this example) and magnitude of the maximum value within the real vector $RV_R$ from storage buffer 124. A value and index data pair is output for each advance of the window along $RV_R$. Similarly, the output of maximum in window step 170 is the index position and magnitude of the maximum value within the real vector $RV_S$ from storage buffer 142. A value and index data pair is output for each advance of the window along $RV_S$.

The compare maximum to thresholds step 152 first tests whether the maximum value output from maximum in window step 150 meets or exceeds the primary threshold value derived in threshold calculation step 126. If it does, the result is considered to be a "Potential R Hit" 154 that is processed further as described below. Each Potential R Hit corresponds to a position and magnitude in $RV_R$.

Similarly, compare maximum to thresholds step 172 first tests whether the maximum value output from maximum in window step 170 meets or exceeds the primary threshold value derived in threshold calculation 144. If it does, the result is a "Potential S Hit" 174 that is processed further as described below. Each Potential S Hit corresponds to a position and magnitude in $RV_S$.

Alternatively, if the maximum value output from maximum in window step 150 is below the primary threshold value derived in threshold calculation step 126, and the maximum value output from maximum in window step 170 is below the primary threshold value derived in threshold calculation step 144, processing will continue by returning to maximum in window step 150 and maximum in window step 170, advancing the windows along each vector $RV_R$ or $RV_S$ to generate new maxima for testing in the compare maximum to thresholds step 152 and compare maximum to thresholds step 172 as described above.

If a Potential R Hit 154 exists, a search is performed in step 176 for the existence of a corresponding or dual hit in an attempt to make an "R, S Hit Pair". It should be noted that if a real correlation between the probe and target exists, then two significant corresponding correlations that were calculated from the superposition R and S wavefunctions (as was discussed earlier above) should also exist. An R, S Hit Pair would correspond to these two correlations and consist of an R hit and an S hit. The method described below intelligently searches for a corresponding or dual R hit or S hit in a range in which such a hit is expected to be if it corresponds to a truly significant correlation between the probe and the target.

In general, the positional separation will be two times the layer number that the signal causing the correlation peaks to appear was earlier encoded into. For example, as will become more clear from the discussion below, if the hit is in a portion of the target sequence that was encoded into layer 3, the positions of the R hit and S hit will be separated by six positions in the position index used for the elements of real vectors $RV_R$ or $RV_S$.

Step 176 first tests, based upon the position of the Potential R Hit within the window used in step 150, if the entire range of possible dual S hit positions (i.e., corresponding to the Potential R Hit) was already included within the window used for the obtaining the S maximum from vector $RV_S$ in step 170. The entire range of possible dual S hit positions is defined relative to the Potential R Hit position by the largest separation delta generated by layer encoding. For any target track 902 (discussed further below) being processed, it is known how many layers have been combined (i.e., the depth of the superposition wavefunctions used). According to the exemplary multi-resolution database 900 (illustrated in FIG. 6), the largest separation delta generated by layer encoding is equal to twice the number of layers in that superposition.

If the entire range of possible dual S hit positions was included in the window of step 170, then the S maximum from step 170 may be used as the possible dual S hit corresponding to the Potential R Hit 154. Alternatively, if the entire range of possible dual S hit positions was not included in the window of step 170, then a search of the vector $RV_S$ is done to select the maximum value from within the entire range of potential dual S hit positions in $RV_S$ for use as the S maximum.

Next, the separation delta of the R and S maxima is calculated. The "separation delta" is equal to the position of the R maximum minus the position of the S maximum. The separation delta is then tested to see if it meets the following three conditions: (i) the separation delta is non-negative, (ii) the separation delta is even-numbered, and (iii) the separation delta is within the range of position separation generated by layer encoding, which as mentioned above, is equal to twice the number of layers in that superposition.

If the separation delta satisfies all of the above three conditions, the magnitude of the S maximum is compared against the secondary threshold previously calculated in threshold calculation step 144. If the magnitude of the S maximum meets or exceeds the secondary threshold, then the sum of the magnitudes of the R and S maxima is compared against the tertiary threshold previously calculated from steps 126 and 144. If the sum of the magnitudes of the R and S maxima is greater than or equal to the tertiary threshold, then the R and S maxima are passed as a potential dual R hit and S hit pair (or simply "R, S hit pair") to step 178.

Step 178 calculates the offset and separation of the potential dual R, S hit pair. Specifically, step 178 finds the position midpoint between the R and S maxima and records this as the offset of the R, S hit pair. In equation form: position midpoint=(position$_R$ maximum+position$_S$ maximum)/2. The separation delta of the two maxima is also determined. The separation delta is equal to the position of the R maximum minus the position of the S maximum.

Similarly as was described above for the existence of a Potential R Hit, if a Potential S Hit 174 exists, a search is performed in step 156 for the existence of a dual hit in an attempt to make an R, S Hit Pair. Step 156 first tests, based upon the position of the Potential S Hit within the window used in step 170, if the entire range of possible dual R hit positions (i.e., corresponding to the Potential S Hit) was already included within the window used for the obtaining the R maximum from vector $RV_R$ in step 150. The entire range of possible dual R hit positions is defined relative to the Potential S Hit position by the largest separation delta generated by layer encoding.

If the entire range of possible dual R hit positions was included in the window of step 150, then the R maximum from step 150 may be used as the possible dual R hit corresponding to the Potential S Hit 174. Alternatively, if the entire range of possible dual R hit positions was not included in the window of step 150, then a search of the vector $RV_R$ is done to select the maximum value from within the entire range of potential dual R hit positions in $RV_R$ for use as the R maximum.

Next, following step 156, is step 158, in which the separation delta of the R and S maxima is calculated. The "separation delta" is equal to the position of the R maximum minus the position of the S maximum. The separation delta is then tested to see if it meets the following three conditions: (i) the separation delta is non-negative, (ii) the separation delta is even-numbered, and (iii) the separation delta is within the range of position separation generated by layer encoding.

If the separation delta satisfies all of the above three conditions, the magnitude of the R maximum is compared against the secondary threshold previously calculated in threshold calculation step 126. If the magnitude of the R maximum meets or exceeds the secondary threshold, then the sum of the magnitudes of the R and S maxima is compared against the tertiary threshold previously calculated from steps 126 and 144. If the sum of the magnitudes of the R and S maxima is greater than or equal to the tertiary threshold, then the R and S maxima are passed as a potential dual R,S hit pair to step 178.

Step 158 calculates the offset and separation of the potential dual R,S hit pair. Specifically, step 158 finds the position midpoint between the R and S maxima and records this as the offset of the R,S hit pair. In equation form: position midpoint=(position$_R$ maximum+position$_S$ maximum)/2. The separation delta of the two maxima is also determined. The separation delta is equal to the position of the R maximum minus the position of the S maximum.

As mentioned above, the processing steps 150, 152, 154, 156 and 158 provide a substantially parallel path to the processing steps 170, 172, 174, 176 and 178, assisting in ensuring that the R and S normalized interference data are initially each screened for hits independently. This approach attempts to ensure that all significant matches between the probe and target sequences will be found since two detection opportunities are created for each match between the probe and the target. The results from these two parallel paths converge in step 180, which qualifies the R,S Hit Pairs. More specifically, step 180 eliminates R,S Hit Pair duplicates from these results (e.g., a duplicate R,S Hit Pair may have arisen as a result of using the parallel detection processes discussed earlier).

As will be discussed in more detail below, when originally preparing the target for searching, the target may be divided into a number of sections (e.g., 128 sections, designated as $S_0 \ldots S_{127}$) with each section encoded to one of the layer indices used for forming the layer-encoded superposition wavefunctions. In step 182, data for each of the R,S Hit Pairs detected in the preceding steps is used to generate the following data for each R,S Hit Pair: (i) a position offset, and (ii) a target section number. The target section number may be used with the position offset to identify the location in the target sequence that matches the probe sequence for the given R,S Hit Pair. The position offset is calculated from the offset of the R,S Hit Pair, which is equal to the position midpoint between the R and S maxima plus an offset of the frame size N for each frame of the target input in steps 110 and 128.

The superposition layer index is obtained by halving the layer separation delta from steps 158 and 178 (equal to the position of the R maximum minus the position of the S maximum). In the exemplary multi-resolution database 900 shown in FIG. 6, the number of sections in each layer varies from two for track 0 (64 deep) to sixty-four for track 5 (2 deep). Accordingly, the superposition layer index is multiplied by the number of sections per layer in the track 902 being processed to obtain the target section number. For example, in the case of a layer separation delta for a R,S dual hit of 16, the superposition layer index of this hit pair would be 8. If track 0 (64 deep) of database 900 in FIG. 6 were being processed, the target section number would be obtained by multiplying 8 by 2, where two is the number of sections in one layer.

The separation delta of the two maxima (as mentioned above, the separation delta is equal to the position of the R maximum minus the position of the S maximum), is divided by two to give the superposition layer number in which the hit was detected. The superposition layer number is then multiplied by the number of target sections originally included in each layer in order to yield the target section number (e.g., a number selected from the range 0 to 127 in the specific example discussed herein) in which the matching sequence is located.

FIGS. 5E-5F illustrate a multidimensional continuous sequence searching method 107, using interference between the n-dimensional probe wavefunctions prepared by the method 103 of FIG. 3B and RS pairs of n-dimensional target wavefunctions prepared by the continuous variant of method 105 for target preparation depicted in FIG. 4B and including the assessment of hits that are located. More specifically, method 107 involves the search for and detection of any pattern matches in the target wavefunction superpositions and the reading of the n-dimensional coordinate position offset plus the layer index of any detected matches. An essential feature of method 107 is that the potential probe sequence match contained in the target sequence may be represented by two separate RS pairs of target wavefunction superpositions. This situation occurs when the potential probe match sequence contained in the target sequence is represented in two separate regions output from Partition Regions 33. To handle this situation the method 107 uses overlap buffers 117 and 135 to combine the interference results from two separate RS pairs. As a result, the correlation result for the entire potential probe match sequence is obtained from the overlap and add of the correlation result of one portion of the potential probe match sequence generated from one RS pair with the correlation result of other portion of the potential probe match sequence generated from another RS pair.

The method 107 illustrated in FIGS. 5E-5F is especially suited to multidimensional object recognition applications it situations such as a conveyor belt of luggage moving past a Computerized Tomography (CT) scanner or a street view of a self-driving vehicle. In these cases a continuous time sequence of target data corresponding to successive CT images or street views. An object recognition task involves searching for a probe or query data sequence in the continuous time sequence of target data and outputting the identity and location of any match. The continuous time sequence of target data is processed in sections and as a result the potential probe match contained in the target data may be processed to separate RS wavefunction superposition pairs. In method 107 the overlap and add of the interference results from separate RS pairs generates a continuous correlation result for any probe sequence regardless of where the target sequence data was partitioned for processing by Partition Regions 33 in FIG. 4B operating according to the continuous dimension layer encoding method.

According to the present disclosure, the pattern matching search process performs an interference between the n-dimensional probe wavefunction 147 and one or more n-dimensional superpositions of n-dimensional target wavefunctions that have been n-dimensionally modulated according to their particular layer index, as was discussed above. In the diagram of method 107, two separate n-dimensional superposition wavefunctions are input: n-dimensional target wavefunction superposition R matrix 111 and target wavefunction superposition S matrix 129. Superpositions 111 and 129 may be a n-dimensional superposition R, S pair ($\psi RM$, $\psi SM$) to be processed next from among the many such n-dimensional R, S pairs that have been scheduled for having consecutive numbers in the Regional Metadata associated with each R,S pair.

Method 107 illustrates the parallel searching of many such corresponding n-dimensional superposition R, S pairs. In some embodiments a separate program instance processes a unique combination of probe n-dimensional wavefunction 147 and the R, S pair comprising target n-dimensional wavefunction superposition R 111 and target n-dimensional wavefunction superposition S 129. Many program instances running concurrently provide a way to efficiently search a very large database comprised of R,S pairs for a large number of search probe queries.

The input n-dimensional probe wavefunction $\varphi M$ 147 is prepared by method 103 of FIG. 3B. The complex conjugate of $\varphi M$ is calculated in step 149 and is designated $\varphi M^*$. The complex conjugate $\varphi M^*$ is then interfered separately with each of $\psi RM$ and $\psi SM$ by performing an n-dimensional matrix complex multiply operation in each of steps 113 and 131, respectively. The output from each step 113 and 131 is an n-dimensional complex matrix.

The outputs of n-dimensional matrix complex multiply steps 113 and 131 are next each processed with a unitary n-dimensional orthogonal inverse transform in steps 115 and 133, respectively. These n-dimensional inverse transforms are the inverse of the n-dimensional transform that was previously used to prepare the n-dimensional probe and target wavefunctions above. While many possibilities exist for the unitary n-dimensional orthogonal inverse transforms 115 and 133 as mentioned earlier, for the purposes of the present embodiment the unitary n-dimensional orthogonal transform will be an inverse discrete multidimensional Fourier transform of n dimensions.

As will be next discussed, overlapping portions selected from the incoming n-dimensional inverse transform matrix outputs from steps 115 and 133 will be separately added to overlap buffer 117 and overlap buffer 135 respectively, to provide n-dimensional matrix complex addition results at each of steps 119 and 137. These results are designated for later reference as $VCAM_R$ and $VCAM_S$, respectively. After the processing described below, each of the n-dimensional matrix results $VCAM_R$ and $VCAM_S$ will be an n-dimensional complex matrix of length (N1, N2, . . . , Nn) complex elements for the exemplary input n-dimensional target sequence size of (N1, N2, . . . , Nn) data elements. It should be noted that a benefit of the overlapping of successive n-dimensional transforms is to create $VCAM_R$ and $VCAM_S$ data that is independent of the n-dimensional probe sequence occurrences in the target n-dimensional sequence, even when the n-dimensional probe sequence is contained in two separate but consecutive n-dimensional wavefunction superposition R, S pairs comprising target wavefunction superposition R and S input to steps 111 and 129 respectively.

More specifically, each of the complex matrices output from step 115 (each such complex matrix is designated as "frame h" for purposes of discussion) is processed to overlap a portion of a given frame h with a portion of its predecessor frame using an overlap buffer 117 and a matrix complex add operation at step 119. For discussion purposes, each predecessor and successor complex matrix output from step 115 is designated as "frame h−1" and "frame h+1", respectively. For the example of an initial input target n-dimensional sequence with lengths in each dimension of (N1, N2, . . . , Nn), each frame h contains (2N1, 2N2, . . . , 2Nn) elements. For purposes of discussion, the elements for frame h may be considered as divided, according to the continuous dimension specified in the Regional Metadata associated with the input 70, into a first half of an n-dimensional range of elements with coordinates 0 to N−1 in the continuous dimension, and a second half of an n-dimensional range of elements with coordinates N to 2N−1 in the continuous dimension (each half contains a range of N coordinates in the continuous dimension). For each frame output from step 115, the matrix elements 0 to N−1 in the continuous dimension from the first half of the frame are stored in an n-dimensional overlap buffer at step 117. N-dimensional overlap buffers 117 and 135 may be any suitable form of memory or other storage.

Next, in step 119 each of n-dimensional matrix elements N to 2N−1 in the continuous dimension in the second half of a new frame h output from step 115 comprising negative lag correlations of frame h is added using n-dimensional matrix complex addition step 119 to the corresponding elements 0 to N−1 in the continuous dimension in the first half of the preceding output frame h−1 comprising positive lag correlations of frame h−1, which was previously stored in overlap buffer 117. In other words, element 0 in the continuous dimension is added to element N in the continuous dimension, element 1 is added to element N+1, and so forth, and element N−1 is added to element 2N−1. The output from step 119 ($VCAM_R$) is a set of n-dimensional complex correlations in the range 0 to N−1 in the continuous dimension for each incoming frame h. The total number of matrices $VCAM_R$ output from step 119 is one for each frame input 70 RS pair processed in steps 111 and 129. During loop processing, the total number of matrices $VCAM_R$ output from step 119 is equal to the number of target n-dimensional wavefunction superpositions input in 70 Target RS pair that are passed to steps 111 and 129.

The first half (elements with coordinates 0 to N−1 in the continuous dimension) comprising positive lag correlations of the same new output frame h from the unitary n-dimensional orthogonal inverse transform 115 is stored in overlap buffer 117 until it is brought together with the second half (elements with coordinates N to 2N−1 in the continuous dimension) comprising negative lag correlations of the next output frame h+1 from inverse transform 115. As a result of this repeated overlap and matrix complex addition processing, matrix complex addition 119 outputs a matrix $VCAM_R$ with a length that is half that of the output matrices from unitary n-dimensional orthogonal inverse transform 115.

In a similar manner to that described immediately above, each of many complex matrix outputs from unitary n-dimensional inverse transform step 133 is processed to overlap each frame with its predecessor and successor frames using overlap buffer 135 and n-dimensional matrix complex addition 137. As a result of this repeated overlap and matrix addition process, n-dimensional matrix complex addition 137 outputs a matrix $VCAM_S$ with a length that is half that of the output matrix from unitary n-dimensional inverse transform 133. The output from step 137 ($VCAM_S$) is a set of N n-dimensional complex correlations with coordinates 0 to N−1 in the continuous dimension for each incoming frame h.

The next steps involve processing the output matrix $VCAM_R$ of n-dimensional matrix complex addition step 119 via a complex inflation step 190, and processing the output matrix $VCAM_S$ of n-dimensional matrix complex addition step 137 via a complex inflation step 198. For each complex inflation step 190 and 198, each element of the matrix $VCAM_R$ and $VCAM_S$, respectively, is raised to the third power using complex multiplication. In other embodiments, it should be noted that other powers or other manners of inflation may be used. Complex inflation may assist in separating background noise in matrices $VCAM_R$ and $VCAM_S$ from peak signals therein that correspond to potential matches between the n-dimensional probe and the n-dimensional target database.

The outputs from complex inflation steps 190 and 198 may be processed using optional phase filtering steps 191 and 199. Typically, this is designed to select direct correlates and exclude phase rotated correlates since these are of greater interest in representing a pattern match. The outputs from this phase filtering are provided to modulus and normalization steps 123 and 141, respectively. Each of these steps 191 and 199 involves phase scaling by multiplying each complex element of each of the inflated matrices by a phase scale factor. The phase scale factor may be determined by the phase of the complex element. For example, the phase scale factor F may be cosine (arctangent (imaginary/real)) for the interval where real is positive. In the case where the real is less than or equal to zero, the phase scale factor F is zero. The phase filtered complex value output is (F*real, F*imag). The phase scaling may eliminate correlations that are out of phase. For example, there may be a match that is not a direct phase match to a probe, but instead is a rotation of that phase (e.g., the same sequence rotated by 90°).

The two parallel processing paths continue with the providing of the output of complex inflation step 190 to modulus and normalization step 123, and providing of the output of complex inflation step 198 to modulus and normalization step 141. Each of the modulus and normalization steps 123 and 141 involves calculation of the real modulus of each input complex element followed by a multiplication by a normalization scale factor that is constant for all elements in the input n-dimensional matrix to step 123 or 141. The normalization scale factor may be determined using the theoretical maximum correlation value corresponding to the n-dimensional matrix outputs from steps 115 and 133. The normalization scale factor may be calculated as the desired output peak height divided by a total input energy calculated according to the energy, or power metric, of the input probe n-dimensional wavefunction 147. In the some embodiments the probe or search n-dimensional wavefunction prepared by method 103 is encoded by step 21 to generate an interference output of unity for a potential probe sequence that is 100% similar.

In other embodiments the same principles of power conservation will apply with different intermediate scale factors. For example, in the method 103 the n-dimension probe sequence 17 is transformed to an n-dimension wavefunction 27 via steps 21 and 25, each of which may apply predetermined scaling factors to the total power of probe sequence 17. As a result the total power of probe n-dimensional wavefunction 147 input to method 107 would be a predetermined scale factor of the total power of the n-dimensional probe 17.

The n-dimensional interference process 107 calculates any correlation between the n-dimensional probe data sequence and the n-dimensional target data sequence represented as an RS pair of n-dimensional wavefunction superpositions, by n-dimensional matrix complex multiplication in steps 113 and 131 of the target n-dimensional wavefunctions 111 and 129 with the complex conjugate of the probe n-dimensional wavefunction 147 complex matrix, followed by unitary n-dimensional orthogonal inverse transforms 115 and 133.

The output of each step 123 and 141 is a matrix of scalar numbers (each matrix is designated as $RVM_R$ and $RVM_S$, respectively) representing the scaled magnitude of the corresponding input complex matrix elements. For example, for an exemplary input frame length of $N1, \ldots, Nn$ elements in each of then dimensions, $RVM_R$ and $RVM_S$ contain $N1, \ldots, Nn$ real numbers in each of the n dimensions. Each of the matrices $RVM_R$ and $RVM_S$ is a correlation at a particular n-dimensional grid position between the probe n-dimensional sequence and the target n-dimensional sequence. It should be noted that this correlation may be measured at every grid position in the target n-dimensional sequence of data elements.

The outputs of steps 123 and 141 may be temporarily saved to n-dimensional storage buffers 125 and 143, respectively. These n-dimensional storage buffers may be used to hold these normalized results of the n-dimensional superposition R and S wavefunction interferences with the n-dimensional probe wavefunction so that the results may be further analyzed to determine if any hits or significant similarities are present. In this specific context, a "hit" refers to a peak value in the normalized data output from step 123 or 141.

In typical use, there is a stream of n-dimensional real matrices $RVM_R$ and $RVM_S$, with corresponding $RVM_R$ and $RVM_S$ matrices stored in n-dimension storage buffer 125 or 143 for each n-dimensional superposition wavefunction R, S pair (ψRM, ψSM) that entered method 107 at steps 111 and 129. The number of $RVM_R$, $RVM_S$ matrix pairs will depend, for example, on the resolution of an n-dimensional image in the database that was selected for searching. The real matrices typically abut one another directly (i.e., this process is like the assembly of one long real matrix, with a length depending, for example, the number of layers being processed in parallel). The $RVM_R$ and $RVM_S$ n-dimensional matrices are examined for peaks that correspond to high correlations between the n-dimensional probe and the n-dimensional target.

Hit Detection Process in Multidimensional Search

In an attempt to capture all potentially significant matches between the n-dimensional probe and n-dimensional target sequences, the hit detection process described below contains several steps. These steps are designed to identify all potential candidates, then to perform a more rigorous qualification of these candidates to attempt to eliminate false detection events. The hit detection process outputs qualified events comprising a pair of hits, one each from the parallel R and S n-dimensional wavefunction interference processing paths described above. However, as part of the hit detection process, the real n-dimensional matrices $RVM_R$ and $RVM_S$ are initially each screened for hits independently. This approach improves the likelihood that all significant matches between the n-dimensional probe and n-dimensional target sequences will be found since two detection opportunities are thus created for each potential match.

The hit detection process begins with a threshold calculation at step 127, which is applied to data from real n-dimensional matrix $RVM_R$ obtained from n-dimensional matrix storage buffer 125 and a threshold calculation at step 145, which is applied to data from real n-dimensional matrix $RVM_S$ obtained from n-dimensional matrix storage buffer 143. In each case, the normalized magnitude data are analyzed using statistical methods to calculate the mean and standard deviation of each set of data. In threshold calculation 127 two threshold values are calculated for the n-dimensional R wavefunction interference data, and in threshold calculation 145 two thresholds are calculated for the n-dimensional S wavefunction interference data.

Each pair of thresholds consists of a primary threshold and a secondary threshold, with the primary threshold being greater than the corresponding secondary threshold. These thresholds are calculated by adding the mean value to a multiple of the standard deviation value of the respective data set. For example, the multiples may be sixteen times in the case of the primary threshold and six times in the case of the secondary threshold. For the primary threshold a larger multiple is applied to the standard deviation value, and for the secondary threshold a smaller multiple is applied to the standard deviation value. In addition, a tertiary threshold is calculated for each data set using the combined means from steps 127 and 145 plus a multiple of the combined standard deviations from steps 127 and 145. This multiple is, for example, sixteen times the combined standard deviations. The tertiary threshold is used to test the combined maximum values in a pair of R, S hits. The use of the primary, secondary and tertiary thresholds is described below.

The next steps in the detection process are the determination of a maximum in a window in a step 151, which is applied to the data from the n-dimensional R wavefunction interference in storage buffer 125, and a maximum in a window in a step 171, which is applied to the data from the n-dimensional S wavefunction interference in storage buffer 143. The window length is in each case equal to the effective length of the n-dimensional probe sequence, where the effective length refers to the n-dimensional bounding region of the probe n-dimensional sequence. Using a window size determined in this manner attempts to account for a hypothetical worst case scenario in which the probe sequence repeats itself as two adjacent sequences in the overall target sequence.

The window is advanced across the full length of each real n-dimensional matrix $RVM_R$ and $RVM_S$. The window is advanced, after each selection of a maximum value, by a number of index positions in matrix $RVM_R$ or $RVM_S$ equal to the total window length so that no given sequence position of the real matrix is examined in step 151 more than once. A maximum value is selected from within the window for each matrix $RVM_R$ or $RVM_S$ at each position in its advance along the corresponding n-dimensional matrix.

The output of maximum in window step 151 is the n-dimensional coordinate position (selected from positions with coordinates in the range 0 to N1-1, 0 to N2-1, . . . , 0 to Nn-1 in this example) and magnitude of the maximum value within the real n-dimensional matrix $RVM_R$ from storage buffer 125. A value and n-dimensional coordinate data pair is output for each advance of the window along $RVM_R$. Similarly, the output of maximum in window step 171 is the n-dimensional coordinate position and magnitude of the maximum value within the real n-dimensional matrix $RVM_S$ from storage buffer 143. A maximum value and n-dimensional coordinate position data pair is output for each advance of the window in $RVM_S$.

The compare maximum to thresholds step 153 first tests whether the maximum value output from maximum in window step 151 meets or exceeds the primary threshold value derived in threshold calculation step 127. If it does, the result is considered to be a "Potential R Hit" 155 that is processed further as described below. Each Potential R Hit corresponds to a n-dimensional coordinate position and magnitude in $RVM_R$.

Similarly, compare maximum to thresholds step 173 first tests whether the maximum value output from maximum in window step 171 meets or exceeds the primary threshold value derived in threshold calculation step 145. If it does, the result is a "Potential S Hit" 175 that is processed further as described below. Each Potential S Hit corresponds to a n-dimensional coordinate position and magnitude in $RVM_S$.

Alternatively, if the maximum value output from maximum in window step 151 is below the primary threshold value derived in threshold calculation step 127, and the maximum value output from maximum in window step 171 is below the primary threshold value derived in threshold calculation step 145, processing will continue by returning to maximum in window step 151 and maximum in window step 171, advancing the windows along each n-dimensional matrix $RVM_R$ or $RVM_S$ to generate new maxima for testing in the compare maximum to thresholds step 153 and compare maximum to thresholds step 173 as described above.

If a Potential R Hit 155 exists, a search is performed in step 177 for the existence of a corresponding or dual hit in an attempt to make an "R, S Hit Pair". It should be noted that if a real correlation between the n-dimensional probe and n-dimensional target exists, then two significant corresponding correlations that were calculated from the superposition R and S wavefunctions (as was discussed earlier above) should also exist at two n-dimensional coordinate positions. An R, S Hit Pair would correspond to these two correlations and consist of an R hit and an S hit. The method described below intelligently searches for a corresponding or dual R hit or S hit in a range in which such a hit is expected to be if it corresponds to a truly significant correlation between the probe and the target. In general, the n-dimensional coordinate positional separation will be two times the n-dimensional coordinate position of the layer number that the signal causing the correlation peaks to appear was earlier encoded into. For example, as will become more clear from the discussion below, if the hit is in a portion of the target sequence that was encoded by a layer delta function generated from n-dimensional coordinate of (3, 0, . . . , 0) for layer 3, the positions of the R hit and S hit will be separated by six positions in the first dimension of n-dimensional coordinate positions used for the elements of real matrices $RVM_R$ or $RVM_S$.

Step 177 first tests, based upon the n-dimensional position of the Potential R Hit within the window used in step 151, if the entire range of possible dual S hit positions (i.e., corresponding to the Potential R Hit) was already included within the window used for the obtaining the S maximum from matrix $RVM_S$ in step 171. The entire range of possible dual S hit positions is defined relative to the Potential R Hit position by the largest separation delta generated by layer encoding. For any target n-dimensional sequence being processed, it is known how many layers have been combined (i.e., the depth of the superposition wavefunctions used) and the range of n-dimensional positions used to generate layer delta functions, hence the largest separation delta generated by layer encoding is also known.

If the entire range of possible dual S hit positions was included in the window of step 171, then the S maximum from step 171 may be used as the possible dual S hit corresponding to the Potential R Hit 155. Alternatively, if the entire range of possible dual S hit positions was not included in the window of step 171, then a search of the n-dimensional matrix $RVM_S$ is done to select the maximum value from within the entire range of potential dual S hit positions in $RVM_S$ for use as the S maximum.

Next, the n-dimensional coordinate separation delta of the R and S maxima is calculated. The "n-dimensional coordinate separation delta" is equal to the n-dimensional coordinate position of the R maximum minus the n-dimensional coordinate position of the S maximum. The n-dimensional coordinate separation delta is then tested to see if it meets the following three conditions: (i) the n-dimensional coordinate separation delta is non-negative, (ii) the n-dimensional coordinate separation delta is even-numbered, and (iii) the n-dimensional coordinate separation delta is within the range of position separation generated by n-dimensional coordinate layer encoding.

If the n-dimensional coordinate separation delta satisfies all of the above three conditions, the magnitude of the S maximum is compared against the secondary threshold previously calculated in threshold calculation step 145. If the magnitude of the S maximum meets or exceeds the secondary threshold, then the sum of the magnitudes of the R and S maxima is compared against the tertiary threshold previously calculated from steps 127 and 145. If the sum of the magnitudes of the R and S maxima is greater than or equal to the tertiary threshold, then the R and S maxima are passed as a potential dual R hit and S hit pair (or simply "R, S hit pair") to step 179.

Step 179 calculates the n-dimensional coordinate offset and n-dimensional coordinate separation of the potential dual R, S hit pair. Specifically, step 179 finds the n-dimensional coordinate position midpoint between the R and S maxima and records this as the n-dimensional coordinate offset of the R, S hit pair. In equation form: position midpoint(m)=(position(m)$_R$ maximum+position(m)$_S$ maximum)/2, where m is each of the n-dimensional coordinates. The n-dimensional coordinate separation delta of the two maxima is also determined. The n-dimensional coordinate separation delta is equal to the n-dimensional coordinate position of the R maximum minus the n-dimensional coordinate position of the S maximum.

Similarly as was described above for the existence of a Potential R Hit, if a Potential S Hit 175 exists, a search is performed in step 157 for the existence of a dual hit in an attempt to make an R, S Hit Pair. Step 157 first tests, based upon the position of the Potential S Hit within the window used in step 171, if the entire range of possible dual R hit positions (i.e., corresponding to the Potential S Hit) was already included within the window used for the obtaining the R maximum from matrix $RVM_R$ in step 151. The entire range of possible dual R hit positions is defined relative to the Potential S Hit position by the largest n-dimensional coordinate separation delta generated by n-dimensional coordinate layer encoding.

If the entire range of possible dual R hit positions was included in the window of step 151, then the R maximum from step 151 may be used as the possible dual R hit corresponding to the Potential S Hit 175. Alternatively, if the entire range of possible dual R hit positions was not included in the window of step 151, then a search of the matrix $RVM_R$ is done to select the maximum value from within the entire range of potential dual R hit positions in $RVM_R$ for use as the R maximum.

Next, following step 157, is step 159, in which the n-dimensional coordinate separation delta of the R and S maxima is calculated. The "n-dimensional coordinate separation delta" is equal to the n-dimensional coordinate position of the R maximum minus the n-dimensional coordinate position of the S maximum. The separation delta is then tested to see if it meets the following three conditions: (i) the n-dimensional coordinate separation delta is non-negative, (ii) the n-dimensional coordinate separation delta is even-numbered, and (iii) the n-dimensional coordinate separation delta is within the range of position separation generated by n-dimensional coordinate layer encoding.

If the n-dimensional coordinate separation delta satisfies all of the above three conditions, the magnitude of the R maximum is compared against the secondary threshold previously calculated in threshold calculation step 127. If the magnitude of the R maximum meets or exceeds the secondary threshold, then the sum of the magnitudes of the R and S maxima is compared against the tertiary threshold previously calculated from steps 127 and 145. If the sum of the magnitudes of the R and S maxima is greater than or equal to the tertiary threshold, then the R and S maxima are passed as a potential dual R,S hit pair to step 179.

Step 159 calculates the n-dimensional coordinate offset and n-dimensional coordinate separation of the potential dual R,S hit pair. Specifically, step 159 finds the n-dimensional coordinate position midpoint between the R and S maxima and records this as the n-dimensional coordinate offset of the R,S hit pair. In equation form: position midpoint $(m) = (position(m)_R \text{ maximum} + position(m)_S \text{ maximum})/2$, where m is each of the n-dimensional coordinates. The n-dimensional coordinate separation delta of the two maxima is also determined. The n-dimensional coordinate separation delta is equal to the n-dimensional coordinate position of the R maximum minus the n-dimensional coordinate position of the S maximum.

As mentioned above, the processing steps 151, 153, 155, 157 and 159 provide a substantially parallel path to the processing steps 171, 173, 175, 177 and 179, assisting in ensuring that the R and S normalized interference data are initially each screened for hits independently. This approach attempts to ensure that all significant matches between the n-dimensional probe and n-dimensional target sequences will be found since two detection opportunities are created for each match between the n-dimensional probe and the n-dimensional target. The results from these two parallel paths converge in step 181, which qualifies the R,S Hit Pairs. More specifically, step 181 eliminates R,S Hit Pair duplicates from these results (e.g., a duplicate R,S Hit Pair may have arisen as a result of using the parallel detection processes discussed earlier).

As will be discussed in more detail below, when originally preparing the target for searching, the target may be divided into a number of regions with each region encoded to one of the layer indices used for forming the layer-encoded superposition wavefunctions. Each region is also represented by Regional Metadata 34 which was associated with the target RS pair of layer encoded superposition wavefunctions 70 by the target preparation method 105. In step 193, data for each of the R,S Hit Pairs detected in the preceding steps is used with the Regional Metadata to identify the location in the target sequence that matches the probe sequence for the given R,S Hit Pair. The location in the target that matches the probe sequence is found by first identifying which n-dimensional coordinate position the matching target sequence was encoded by, which is next used to recover the Regional Metadata of the matching target sequence. The location in the target sequence of the matching probe is then calculated by combining the bounding region of the encoded target sequence in the recovered Regional Metadata with the n-dimensional coordinate offset of the R,S Hit Pair, which is equal to the n-dimensional coordinate position midpoint between the R and S maxima.

The superposition integer layer index for the R,S Hit pair is obtained by first calculating the n-dimensional coordinate position of the encoding delta function by halving the layer n-dimensional coordinate separation delta from steps 159 and 179 (equal to the n-dimensional coordinate position of the R maximum minus the n-dimensional coordinate position of the S maximum). The n-dimensional coordinate position in the Regional Metadata of all layers encoded in the target RS pair 70 is then compared with the calculated n-dimensional coordinate position of the encoding delta function and the Regional Metadata in which they are equal is selected. The selected Regional Metadata comprises the integer layer index and the region n-dimensional bounds of the n-dimensional target sequence in which the probe sequence match was detected as the RS Hit pair.

The n-dimensional coordinate separation delta of the two maxima (as mentioned above, the n-dimensional coordinate separation delta is equal to the n-dimensional coordinate position of the R maximum minus the n-dimensional coordinate position of the S maximum), is divided by two to give the n-dimensional coordinate position used to encode the superposition layer in which the hit was detected. In other words, for each of the n dimensions the coordinate of the encoding delta function is equal to half the difference between the coordinate of the R maximum minus the coordinate of the S maximum. The halving of the separation delta of the two maxima is the final step of a unitary decoding by the wavefunction interference method 107 of the layer encoded target RS pair 70. The unitary decoding by method 107 is the inverse of a unitary encoding by target preparation method 105 in that any n-dimensional coordinate position used to encode a layer in method 105 may be recovered for a matching probe sequence. In target preparation method 105 the target wavefunction in n-dimensional matrix storage buffer 45 is multiplied by a modulation wavefunction in n-dimensional matrix storage buffer 53 to generate a layer in the target n-dimensional wavefunction superposition R matrix. As a result, the positions of potential probe matches will be translated by the n-dimensional coordinate position used to generate the layer encoded as a delta function 47. Similarly, multiplication of the target wavefunction by the complex conjugate of the same modulation wavefunction to generate a layer in the target n-dimensional wavefunction superposition S matrix corresponds to translation of the positions of potential probe matches by the negative of the n-dimensional coordinate position used to generate the layer encoded as a delta function 47. As a result of the equal positive and negative translations in each dimension, a separation is created in each dimension that is twice the positive translation in that dimension. Consequently, the positive translation in each dimension can be recovered by halving the separation in each dimension. The superposition layer number is in order to yield the target in which the matching sequence is located.

Figure 5C:
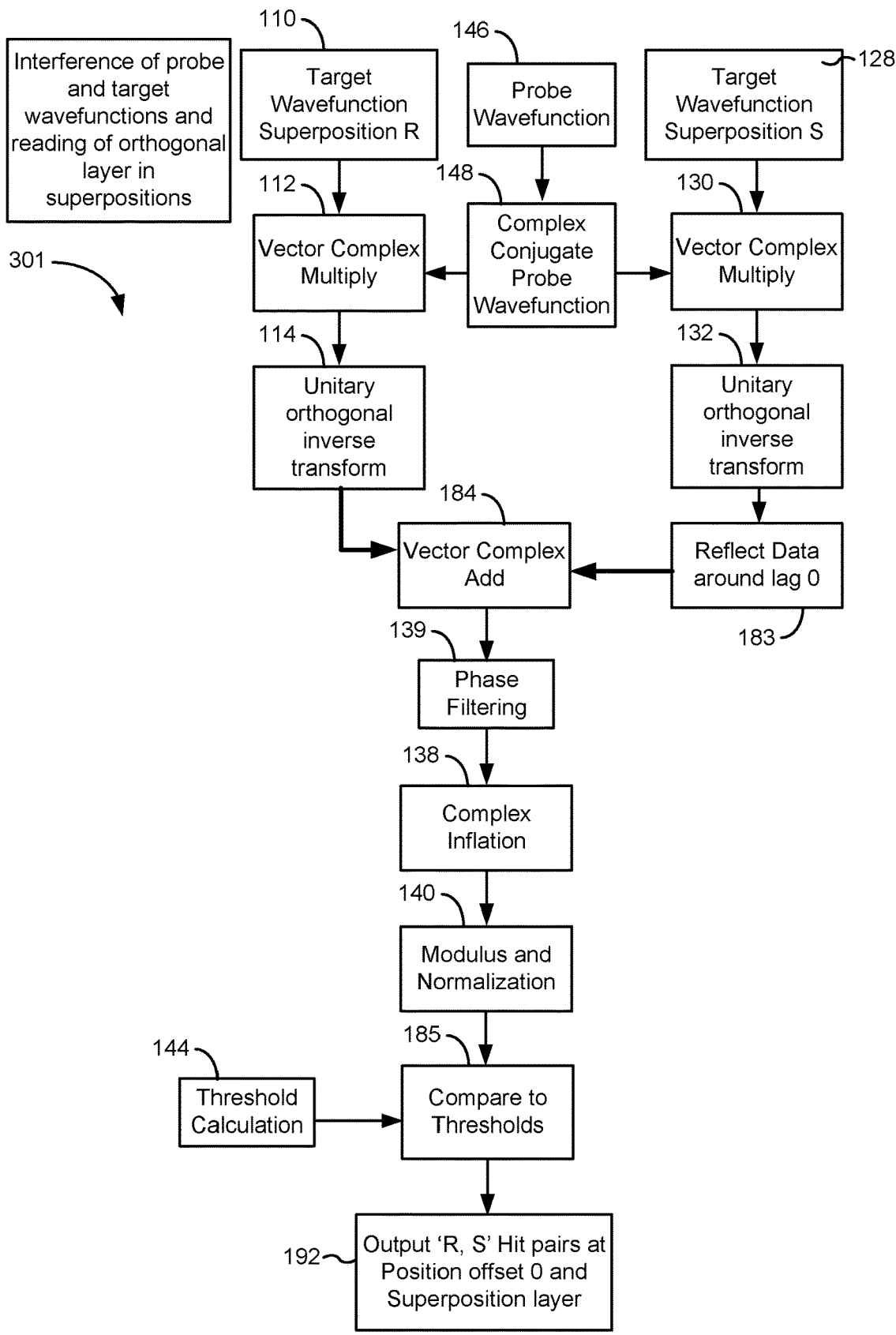
FIG. 5C illustrates a flowchart for a method of sequence searching that is optimized for the special case in which the target sequence has a natural modulus, using interference between the probe and target wavefunctions prepared by the methods of FIGS. 3A and 4A and the assessment of hits that are located, in accordance with some embodiments.

FIG. 5C illustrates a flowchart for a method of sequence searching 300 that is optimized for the special case in which the target sequence has a natural modulus, using interference between the probe and target wavefunctions prepared by the methods of FIGS. 3A and 4A, in accordance with some embodiments. This is also known as the zero-offset use case, for reasons that are explained elsewhere in this document. Many of the steps in method 300 shown in FIG. 5C are analogous to those shown in FIGS. 5A-5B and are thus referred to by the same reference numeral. In addition, the descriptions of these steps are not repeated for the sake of brevity. However, the need for certain outputs of certain steps (e.g., step 114's output to overlap buffer 116) are obviated in accordance with the optimizations in light of the zero-offset use case. Further details about these optimizations are described with reference to FIGS. 11A-11D.

The difference between FIG. 5C and FIGS. 5A-5B is that, after the unitary orthogonal inverse transform step 132, the resulting data is reflected around lag 0 in step 183. The output of step 183 is data that aligns with the resulting data from unitary orthogonal inverse transform step 114 (as will be clear from FIG. 5D, there is at least one other implementation through which to make this alignment of the data). The two sets of data, now aligned, are added in a vector complex addition step 184, in effect, increasing the signal-to-noise ratio of either individual unitary orthogonal inverse transform (i.e., step 114 or step 132). The method proceeds through the numbered steps as described with reference to FIGS. 5A-5B until step 185. At step 185, in some embodiments, the result of step 140 is compared to a predefined threshold, which in some embodiments is predefined based on a calculation done in threshold calculation step 144 based on the parameters of the data stored in the target sequence (e.g., the length of entries, the number of entries, but without regard to further information in the storage buffers 124/142, FIG. 5A).

Stated another way, in FIG. 5A, the position coordinate variable is maintained between frames using Overlap Buffers in steps 116 and 134. The first consequence of the zero position offset alignment use case is that the Overlap Buffers in steps 116 and 134 are not required (as shown in FIG. 5C) since there is no position overlap between frames. In addition, another consequence of the zero position offset alignment use case is that the zero position offset implies a reflection symmetry around zero lag between the output results of unitary orthogonal inverse transforms in steps 114 and 132. This symmetry property provides a computational path to combine the R and S Hit deltas by negating the index of the S encoded target wavefunction output of step 132 to map on top of the positive index of the R encoded target wavefunction from step 114. Negating the index of the S encoded target wavefunction output of step 132 is achieved by reflect data around lag 0 step 183.

The combination of R and S Hit deltas in step 184 of FIG. 5C has two advantages, benefitting both performance and efficiency. Firstly, it makes full use of the orthogonality of the error component of the output of step 114 versus the error component of step 132: complex vector addition in step 184 allows R and S errors to either cancel each other or otherwise not reinforce each other thereby increasing the signal to noise and discrimination of the hit detection process. Secondly, it has the advantage of reducing two downstream paths to a single downstream computational path that processes the R, S hit data more efficiently. A contribution to this greater efficiency is that a dual R and S hit detection process in steps 154, 156, 158, 175, 176, 178 and 180 of FIG. 5B has been replaced by a single, more discriminating, detection process that selects mirror encoded R and S hits in FIG. 5C.

Figure 5D:
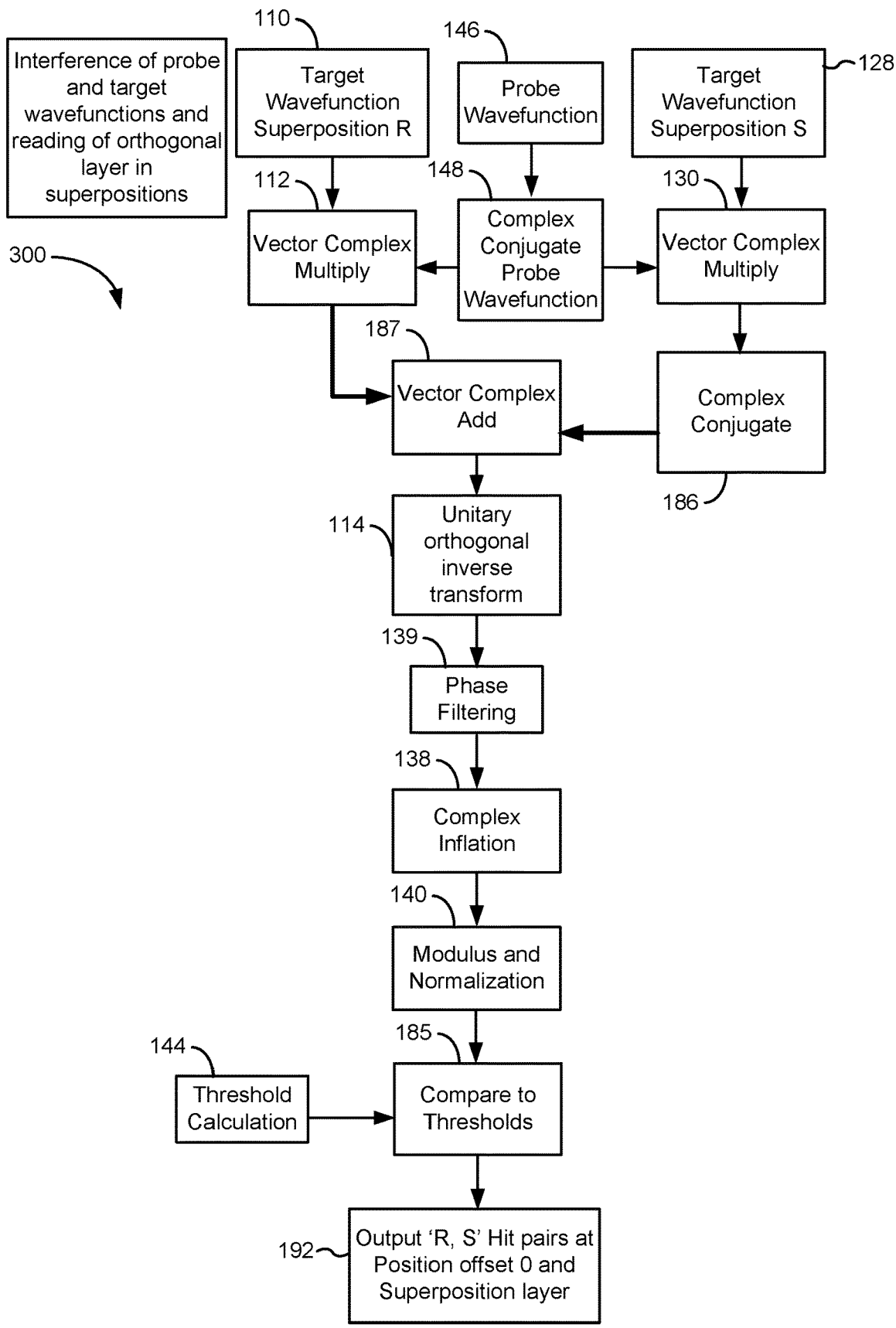
FIG. 5D illustrates a flowchart for a method of sequence searching that is optimized for the special case in which the target sequence has a natural modulus, using interference between the probe and target wavefunctions prepared by the methods of FIGS. 3A and 4A and the assessment of hits that are located, in accordance with some embodiments.
Figure 5E:
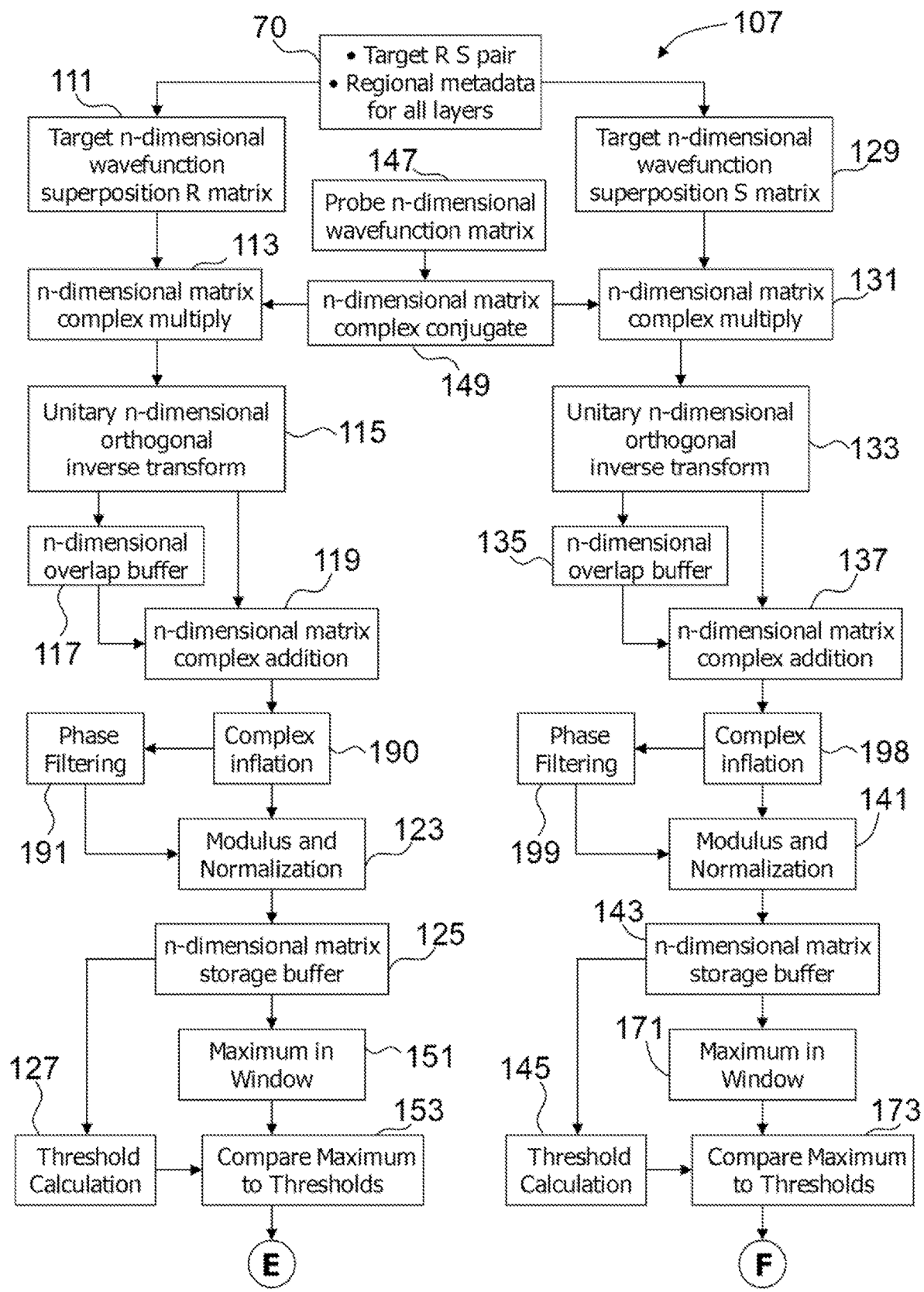
FIGS. 5E-5F illustrate a flowchart for a method of n-dimensional data sequence searching with continuous regions, using n-dimensional interference between the n-dimensional probe wavefunctions prepared by the method of FIG. 3B and n-dimensional target wavefunctions prepared by the continuous variant of method of FIG. 4B and the continuous regions encoded with a continuous dimension using layer delta functions, and the assessment of hits that are located, in accordance with some embodiments.
Figure 5F:
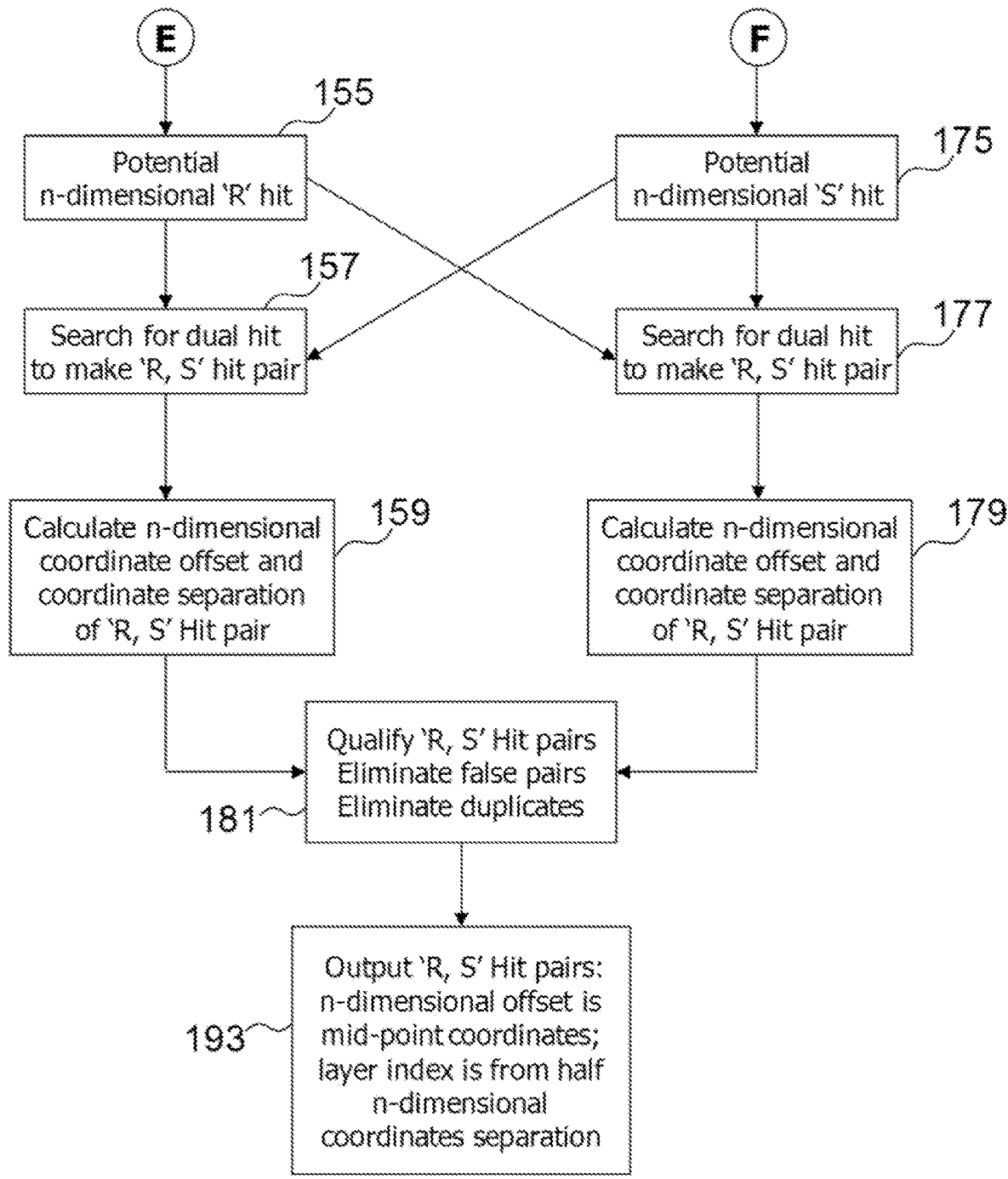

FIG. 5D illustrates a flowchart for another method of sequence searching 301 that is optimized for the special case in which the target sequence has a natural modulus, using interference between the probe and target wavefunctions prepared by the methods of FIGS. 3A and 4A and the assessment of hits that are located, in accordance with some embodiments. Many steps in the method shown in FIG. 5C are analogous to those shown in FIGS. 5A-5B and are thus referred to by the same reference numeral. In addition, the description of these steps is not repeated for the sake of brevity. However, the need for certain outputs of certain steps (e.g., step 114's output to overlap buffer 116) are obviated in accordance with the optimized method for the special case in which the target sequence has a natural modulus. Further details about these optimizations are described with reference to FIGS. 11A-11D.

The difference between FIG. 5D and FIG. 5C is that, rather than reflecting the resulting data from step 132 around lag zero to create the alignment with data from step 114, the alignment is performed prior to applying a unitary orthogonal inverse transform. To that end, the alignment is performed (e.g., in wavefunction space, sometimes called a frequency space) by taking the complex conjugate of the result of the vector complex multiply step 130 prior to obtaining a unitary orthogonal inverse transform in step 114. In addition, in FIG. 5D, the vector complex multiplied data from step 112 is added to the complex conjugated data 186 in a vector complex addition step 187 before the unitary orthogonal inverse transform step 114. This has the effect of increasing the signal-to-noise in the wavefunction space prior to the inverse transform. Another effect is that the need for two unitary orthogonal inverse transform steps is obviated, and hence step 132 is omitted from FIG. 5D.

The computational effect achieved by step 183 in FIG. 5C by reflecting data around lag 0 is also known by the term "time reversal," since each data point at a positive time index moves to its corresponding negative time index and vice-versa. The time reversal operation in step 183 of FIG. 5C has a dual domain equivalent in the orthogonal domain that is the operation of phase conjugation in step 186 of FIG. 5D. The same performance and efficiency advantages of combining orthogonal error components of outputs of steps 114 and 132 in FIG. 5C are equivalently realized by combining orthogonal error components of outputs of steps 112 and 130 in FIG. 5D. By combining R,S Hit data by complex addition in step 187, only a single Unitary Orthogonal inverse transform step 114 is needed in FIG. 5D versus two separate Unitary Orthogonal inverse transforms in steps 114 and 132 in FIG. 5A and/or FIG. 5C.

An additional optimization that may be applied in the zero position offset use case is to select the unitary orthogonal inverse transform to have the same computational properties but partitioned optimally between the probe or search wavefunction encoding method 10 in FIG. 3A and the sequence searching method 100 in FIG. 5A.

Different unitary orthogonal forward/inverse transform pairs may have asymmetric loading between their forward and inverse transform counterparts. Since search requests benefit from lower latency more than storage encoding request, and also predominate over storage encoding requests in frequency of usage, it is more optimal to have the unitary orthogonal inverse transform asymmetrically partitioned to be less computational intensive than the unitary orthogonal forward transform.

Figure 5G:
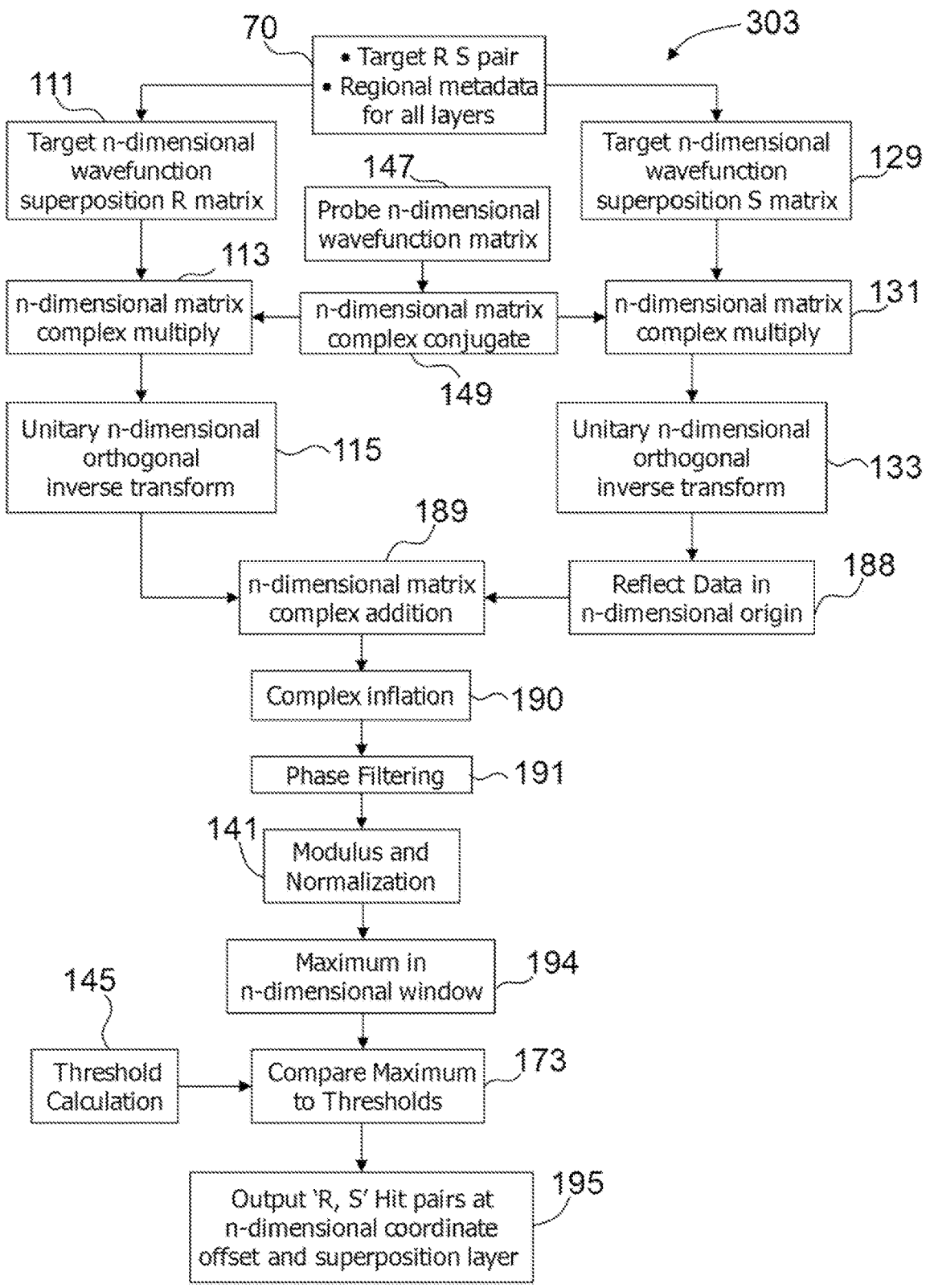
FIG. 5G illustrates a flowchart for a method of n-dimensional sequence searching with discrete regions that is optimized for n-dimensional object recognition in which the n-dimensional target sequence has a natural modulus, using n-dimensional interference between the n-dimensional probe wavefunctions prepared by the method of FIG. 3B and n-dimensional target wavefunctions having discrete regions encoded with a discrete region method of FIG. 4B using the discrete layer delta functions and the assessment of hits that are located, in accordance with some embodiments.

FIG. 5G illustrates a flowchart for a method of n-dimensional discrete sequence searching 303 that is optimized for the special case in which the n-dimensional target sequence has a natural modulus, using interference between the n-dimensional probe wavefunctions prepared by the method 103 of FIG. 3B and RS pairs of n-dimensional target wavefunctions prepared by the discrete variant of method 105 for target preparation depicted in FIG. 4B, in accordance with some embodiments. This is also known as the zero-offset use case, for reasons that are explained elsewhere in this document. Many of the steps in method 303 shown in FIG. 5G are analogous to those shown in FIGS. 5E-5F and are thus referred to by the same reference numeral. In addition, the descriptions of these steps are not repeated for the sake of brevity. However, the need for certain outputs of certain steps (e.g., step 115's output to overlap buffer 117) are obviated in accordance with the optimizations in light of the zero-offset use case.

The primary difference between FIG. 5G and FIGS. 5E-5F is that, after the unitary n-dimensional orthogonal inverse transform step 133, the resulting data is reflected in the n-dimensional coordinate origin in step 188. The output of step 188 is data that aligns with the resulting data from unitary n-dimensional orthogonal inverse transform step 115 (as will be clear from FIG. 5H, there is at least one other implementation through which to make this alignment of the data). The two sets of n-dimensional data, now aligned, are added in a n-dimensional matrix complex addition step 189, in effect, increasing the signal-to-noise ratio of either individual unitary n-dimensional orthogonal inverse transform (i.e., step 115 or step 133). The method proceeds through the numbered steps as described with reference to FIGS. 5E-5F until step 194.

At step 194, in some embodiments, a maximum in n-dimensional window region is calculated on the real normalized correlation output of step 141. In the case that the probe n-dimensional sequence data has a variable n-dimensional offset relative to the potential probe matches in the n-dimensional target data sequence, finding the maximum correlation in a region will compensate for such n-dimensional coordinate position variations.

At Compare Maximum to Thresholds step 173, in some embodiments, the result of step 194 is compared to a predefined threshold, which in some embodiments is predefined based on a calculation done in threshold calculation step 145 based on the parameters of the data stored in the target sequence (e.g., the lengths of entries, the number of entries, but without regard to further information.

At step 194, in some embodiments, a maximum in n-dimensional region is calculated on the real normalized correlation output of step 141 for each integer layer index in a procedure that is described below that iterates over the integer layer indexes and for each one obtains, for example, the scaled and bit-reversed n-dimensional zigzag pattern coordinates described in Partition Regions 33 which was passed via Regional Metadata 34 to step 47, layer encode as delta functional at n-dimensional coordinate position. With the delta function n-dimensional coordinate positions, step 194 also obtains the dimensions of the n-dimensional region that has the single non-zero delta function at its center. As a result step 194 can define limits of an n-dimensional window with which to calculate the maximum in region output correlation.

At step 173, in some embodiments, the result of step 194 comprising a maximum correlation value is compared to a predefined threshold, which in some embodiments is predefined based on a calculation done in threshold calculation step 145 based on the parameters of the data stored in the target sequence (e.g., the length of entries, the number of entries, but without regard to further information).

The output of step 195 comprising the R, S Hit pair in which the hit correlation value at an n-dimensional coordinate offset exceeded the predetermined threshold, the layer in the R, S Hit pair in which the hit exceeded the predetermined threshold is obtained as an integer layer index in the Regional Metadata associated with input 70 which has an n-dimensional coordinate position equal to the n-dimensional coordinate position offset of the hit correlation value that exceeded the predetermined threshold. The integer layer index is passed to the output of method 303.

Stated another way, in FIG. 5E, the n-dimensional position coordinate variable is maintained between frames using Overlap Buffers in steps 117 and 135. The first consequence of the zero position offset alignment use case is that the Overlap Buffers in steps 117 and 135 are not required (as shown in FIG. 5G) since there is no n-dimensional coordinate position overlap between frames. In addition, another consequence of the zero position offset alignment use case is that the zero position offset implies a reflection symmetry around zero lag between the output results of unitary n-dimensional orthogonal inverse transforms in steps 115 and 133. This symmetry property provides a computational path to combine the R and S Hit deltas by negating the n-dimensional coordinate indexes of the S encoded target wavefunction output of step 133 to map on top of the positive n-dimensional coordinate indexes of the R encoded target wavefunction from step 115. Negating the n-dimensional coordinate indexes of the S encoded target wavefunction output of step 133 is achieved by reflect data in the n-dimensional coordinate origin step 188.

Figure 5H:
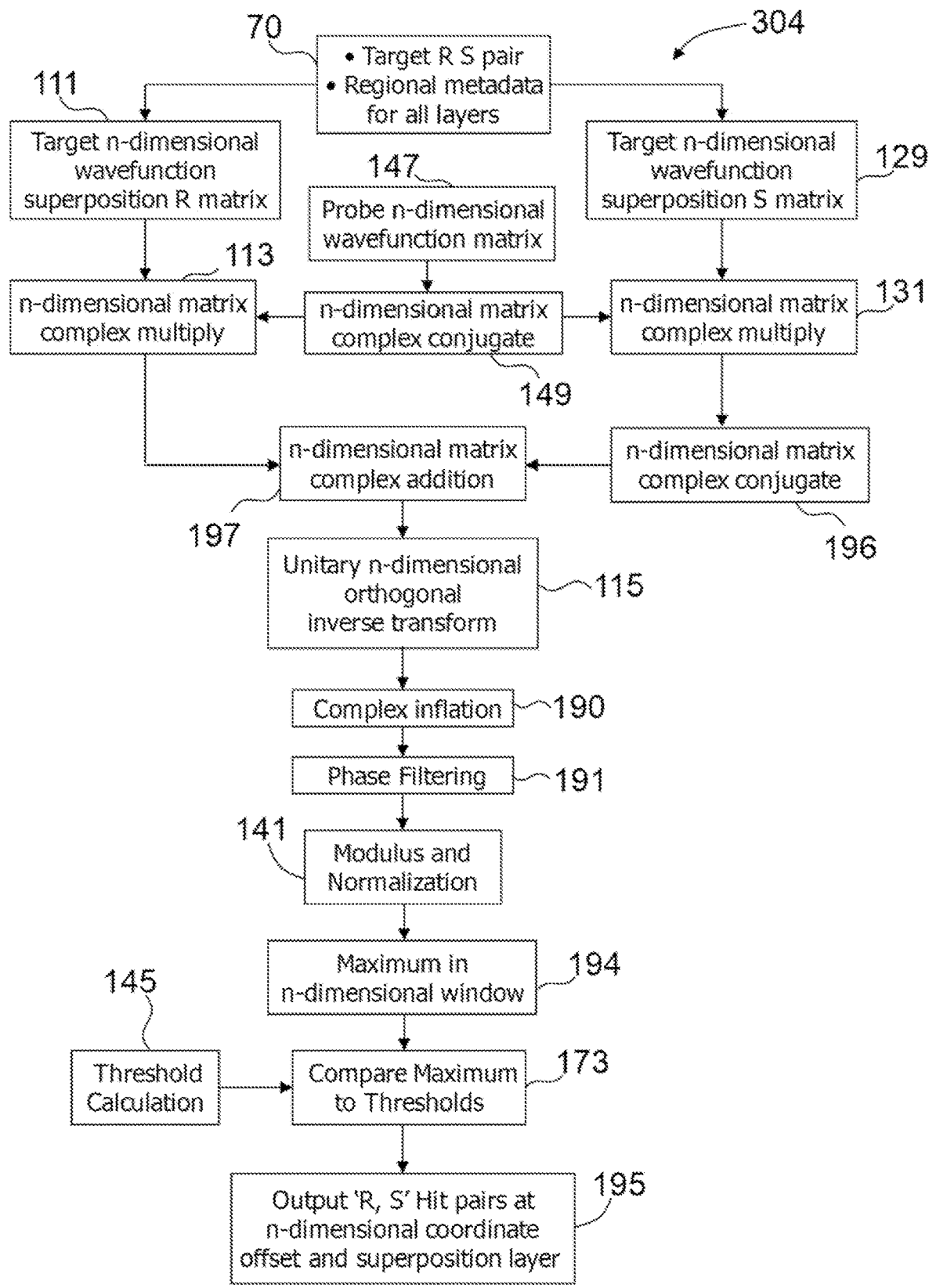
FIG. 5H illustrates a flowchart for a method of n-dimensional data sequence searching with discrete regions that is optimized for n-dimensional object recognition in which the n-dimensional target sequence has a natural modulus, using n-dimensional interference between the n-dimensional probe wavefunctions prepared by the method of FIG. 3B and n-dimensional target wavefunctions having discrete regions encoded with a discrete region method of FIG. 4B using the discrete layer delta functions and the assessment of hits that are located, in accordance with some embodiments.

The combination of R and S Hit deltas in step 189 of FIG. 5G has two advantages, benefiting both performance and efficiency. Firstly, it makes full use of the orthogonality of the error component of the output of step 115 versus the error component of step 133: n-dimensional complex matrix addition in step 189 allows R and S errors to either cancel each other or otherwise not reinforce each other thereby increasing the signal to noise and discrimination of the Hit detection process. Secondly, it has the advantage of reducing two downstream paths to a single downstream computational path that processes the R,S Hit data more efficiently. A contribution to this greater efficiency is that a dual R and S hit detection process in steps 155, 157, 159, 175, 177, 179 and 181 of FIG. 5F has been replaced by a single, more discriminating, detection process that selects mirror encoded R and S hits in FIG. 5G FIG. 5H illustrates a flowchart for another method of multidimensional sequence searching 304 that is optimized for the special case in which the target sequence has a natural modulus, using n-dimensional interference between the n-dimensional probe prepared by the method of FIG. 3B and n-dimensional target wavefunctions prepared by the discrete variant of method 105 depicted in FIG. 4B and the assessment of hits that are located, in accordance with some embodiments. Many steps in the method shown in FIG. 5H are analogous to those shown in FIG. 5G and FIGS. 5E-5F and are thus referred to by the same reference numeral. In addition, the description of these steps is not repeated for the sake of brevity. However, the need for certain outputs of certain steps (e.g., step 115's output to overlap buffer 116)

are obviated in accordance with the optimized method for the special case in which the target sequence has a natural modulus.

The difference between FIG. 5H and FIG. 5G is that, rather than reflecting the resulting data from step 133 in the n-dimensional coordinate origin 188 to create the alignment with n-dimensional data from step 115, the alignment is performed prior to applying unitary n-dimensional orthogonal inverse transform 115. To that end, the alignment is performed (e.g., in wavefunction space, sometimes called a n-dimensional frequency space) by taking the complex conjugate 196 of the result of the n-dimensional matrix complex multiply step 131 prior to obtaining a unitary n-dimensional orthogonal inverse transform in step 115. In addition, in FIG. 5H, the matrix complex multiplied data from step 113 is added to the complex conjugated n-dimensional complex matrix data from step 196 in a matrix complex addition step 197 before the unitary orthogonal inverse transform step 115. This has the effect of increasing the signal-to-noise in the n-dimensional wavefunction space prior to the n-dimensional inverse transform. Another effect is that the need for two unitary n-dimensional orthogonal inverse transform steps is obviated, and hence step 133 is omitted.

The computational effect achieved by step 188 in FIG. 5G by reflecting data in the n-dimensional coordinate origin is also known by the term "time reversal," since each data point at a positive time index moves to its corresponding negative time index and vice-versa. The time reversal operation in step 188 of FIG. 5G has a dual domain equivalent in the orthogonal domain that is the operation of phase conjugation in step 196 of FIG. 5H. For any number of dimensions, the dual domain symmetry applies to a pair of orthogonal n-dimensional dual domains: the complex conjugation of the n-dimensional matrix data before n-dimensional orthogonal inverse transformation is equivalent to a negation of the coordinates, or a reflection in the n-dimensional coordinate origin, of the n-dimensional matrix data in the orthogonal n-dimensional domain following the transformation. The same performance and efficiency advantages of combining orthogonal error components of outputs of steps 115 and 133 in FIG. 5G are equivalently realized by combining orthogonal error components of outputs of steps 113 and 131 in FIG. 5H. By combining R,S Hit data by n-dimensional matrix complex addition in step 197, only a single Unitary n-dimensional Orthogonal inverse transform step 115 is needed in FIG. 5H versus two separate Unitary n-dimensional Orthogonal inverse transforms in steps 115 and 133 in FIG. 5F and/or FIG. 5G.

An additional optimization that may be applied in the zero position offset use case is to select the unitary n-dimensional orthogonal inverse transform to have the same computational properties but partitioned optimally between the n-dimensional probe or search wavefunction encoding method 103 in FIG. 3B and the sequence searching method 107 in FIG. 5E-5F, method 303 in FIG. 5G and method 304 in FIG. 5H.

Different unitary orthogonal forward/inverse transform pairs may have asymmetric loading between their forward and inverse transform counterparts. Since search requests benefit from lower latency than storage and encoding request, and also predominate over storage encoding requests in frequency of usage, it is more optimal to have the unitary orthogonal inverse transform asymmetrically partitioned to be less computational intensive than the unitary orthogonal forward transform.

Multi-Resolution Database

FIG. 6 illustrates a multi-resolution database 900 and the segmentation of a target sequence into multiple sections (designated as $S_0 \ldots S_{127}$), as was mentioned above. Multi-resolution database 900 may be optionally used with the searching method discussed above. However, in other embodiments, different forms of data structure or databases may be used to store the encoded probe and/or target used with the searching methods earlier discussed. For purposes of illustration, genome 101 is shown here as divided into 128 sections. In other embodiments, other numbers of sections may be used.

As discussed above, the multi-resolution database 900 may be organized in a number of different tracks 902 of varying resolutions. Each track 902 corresponds to a different superposition layer depth. For example, Track 1 corresponds to a preparation of all sections using superpositions that are 32 layers of data deep (as was discussed above).

A layer encoding index 904 may be applied to each of these sections for each track 902 of the database as illustrated. For example, the superpositions created for data in sections $S_0$ and $S_1$ of Track 0 are encoded with layer index 0, and sections $S_2$ and $S_3$ are encoded with layer index 1. For Track 6, since it is only one layer deep, it should be noted that only one set of superpositions R is needed, since the superpositions S will be identical for one-layer depth.

Figure 7:
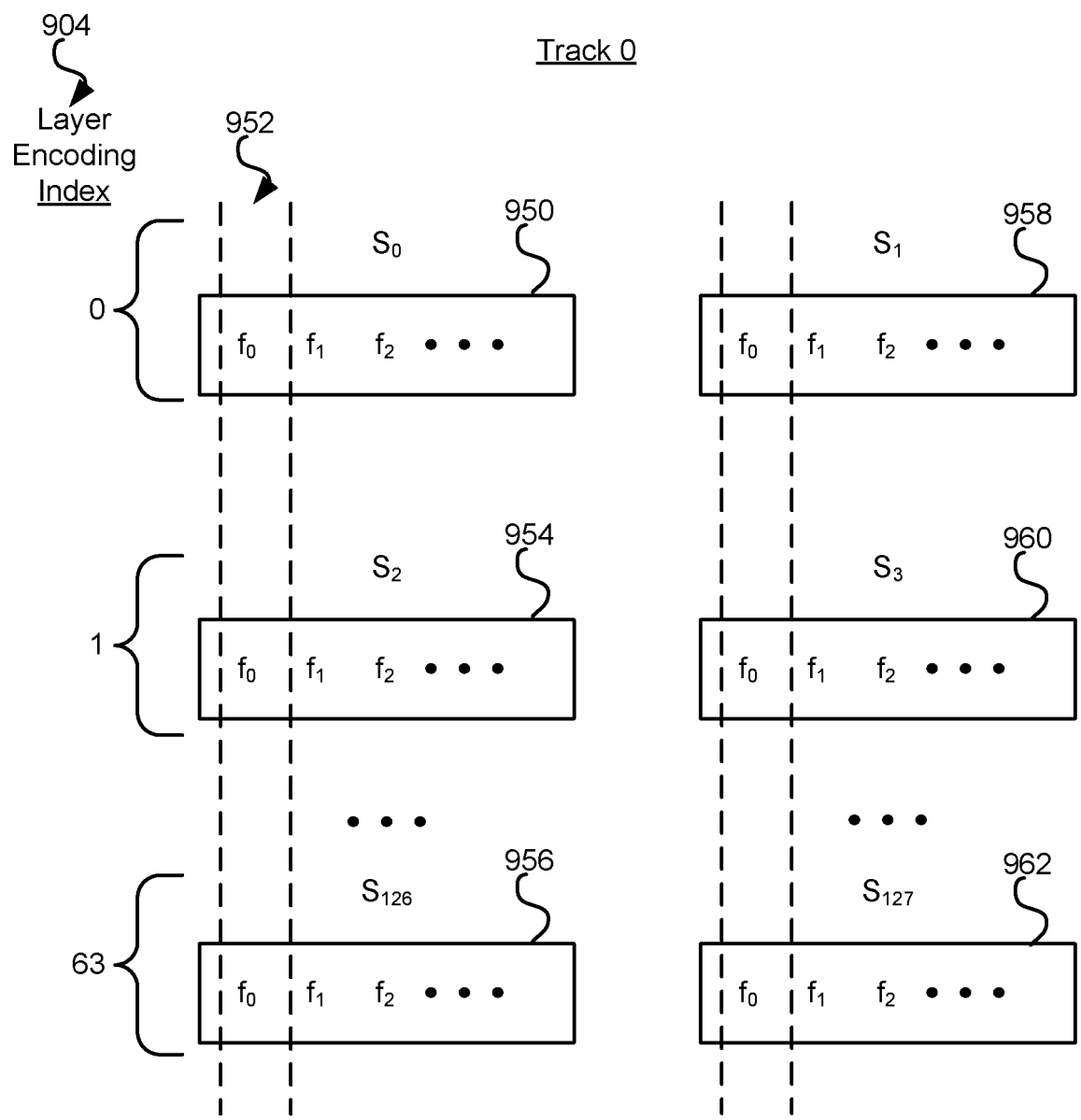
FIG. 7 illustrates the further segmentation into individual frames of the sections of an exemplary track zero of the multi-resolution database of FIG. 6, in accordance with some embodiments.

FIG. 7 illustrates the exemplary further segmentation into individual frames (e.g., $f_0, f_1, f_2, \ldots$) of the sections of Track 0 of multi-resolution database 900. Each section S from database 900 may be organized as a number of frames. The number of frames in each section may be determined, for example, by dividing the total base length of the target by the number of sections (e.g., 128) multiplied by the frame base length (e.g., 2,048 bases).

For example, for a target length of 25,165,824 bases, a total section number selected to be 128 sections, and a frame length selected to be 2,048 bases, the number of frames per section is 96. Thus, frame group 950 corresponding to section So will have 96 frames, and frame group 958 corresponding to section $S_1$ will have 96 frames.

In one approach, a superposition wavefunction R, S pair ($\psi R, \psi S$) is calculated using a frame selected from the same relative position for each layer encoding index 904. For example, $\psi R$ and $\psi S$ are calculated using a superposition of 64 wavefunctions, with each wavefunction corresponding to frame $f_0$ selected from the frame group 950, 954, . . . , 956 as indicated by the dashed lines at 952. A ($\psi R, \psi S$) pair is next calculated for each frame $f_1$, and so on for each corresponding frame position for Sections $S_0, S_2, \ldots, S_{126}$. The same approach is also applied to frame groups 958, 960, . . . , 962 for Sections $S_1, S_3, \ldots, S_{127}$.

To maintain database continuity, it is typically necessary and desirable to remove boundary effects or discontinuities, which may occur as explained below. To accommodate this, there will be an additional overlap frame that is present in each track of more than one-layer deep. The result of the calculations in the simple exemplary case illustrated above will be a total of 1+96+96=193 ($\psi R, \psi S$) pairs for Track 0. These calculations may then be done for each track 902 so that database 900 in general contains a set of ($\psi R, \psi S$) pairs for each track 902, which can be selected and used for searching with a probe as earlier discussed.

As referred to above, overlapping of successive frames creates $VCA_R$ and $VCA_S$ data that is independent of the probe sequence occurrences in the target sequence, even when the probe sequence is contained in two separate, but consecutive wavefunction frames input to steps 110 and 128. The special case where the probe sequence crosses a section boundary is generally dealt with in database 900 by making each track comprise successively ordered sections: the last frame of section 0 is followed by the first frame of section 1, and within all tracks 902 shown in the exemplary case section 0 is followed by section 1.

There is, however, a separate worst case where the probe sequence may cross a section boundary that lies at the end of a track layer. An example of such a case would be a probe that had its first half as the last three bases in section 63 and its second half as the first three bases of section 64. This worst case can be made equivalent to a more normal case by a formatting of database 900 so that duplicates of the last frame of the endmost sections of each track are encoded as an extra frame at the beginning of the next layer of the superposition. For the first section 0, the place of this overlap is filled by a frame of zero data for the purposes of the frame-aligned summation that creates the superposition of layers. Therefore, in database 900 in the exemplary case, the successive layers are arranged so that the section at the end of the track in one layer is followed in the original input information sequence by the first section of the next layer in the superposition. This allows the section boundary to be made transparent as far as output position index such that the same sequence position is represented by the following information: (start of next layer −x) and (end of previous layer+N−x), where x is less than N and the start and end positions are the chromosomal target position indices of the first base in each of the corresponding frames.

In the worst case example where a probe sequence is present in the target with its first half as the last three bases in section 63 and its second half as the first three bases of section 64, there would be a hit detection at a position equal to the starting position of section 64 minus 3 bases. This hit would be generated by $VCA_R$ and $VCA_S$ data that combines the overlap frame from the end of section 63 as a first frame, with the first frame of section 64 as a second frame. As indicated previously, vector elements N to 2N−1 in the second half of a second frame output from step 114 are added using vector complex add step 118 to the corresponding elements 0 to N−1 in the first half of the first output frame, which was previously stored in overlap buffer 116.

In one example of the above, the database is created to maintain continuity across more than 10,000 frames of the frames in the target sequence.

Searching Process and Interaction with
Multi-Resolution Database

Figure 8:
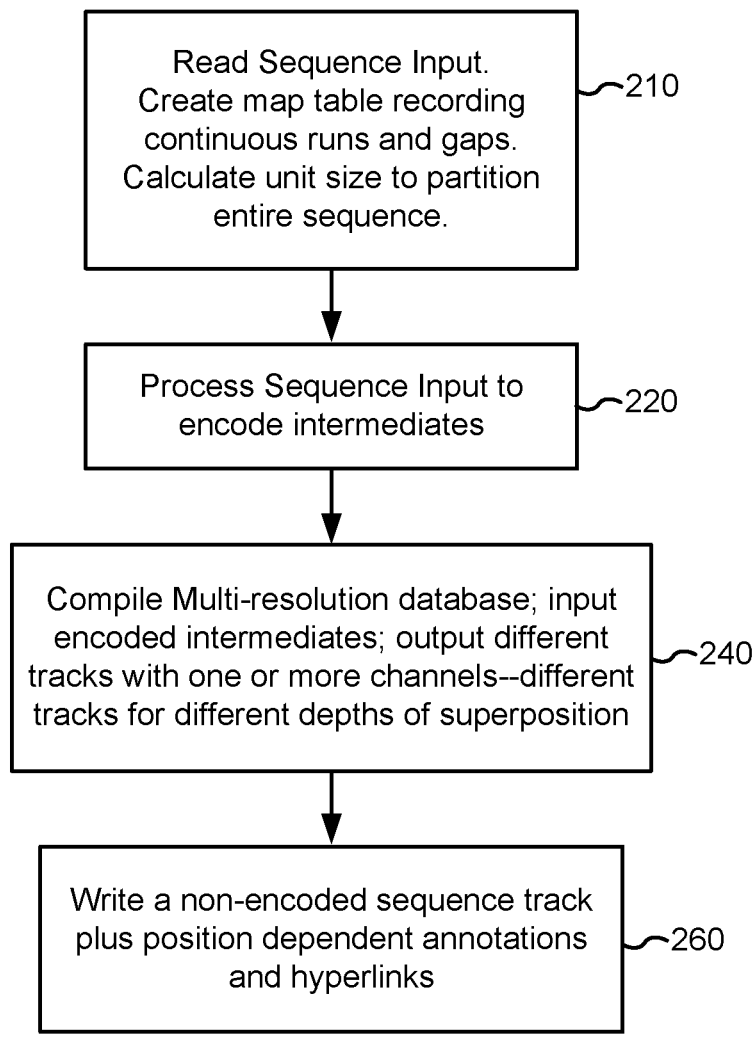
FIG. 8 illustrates the preparation of target data, the multi-resolution database of FIG. 6, and a non-encoded sequence track, in accordance with some embodiments.

FIG. 8 illustrates the preparation of target data and certain interactions that may occur with multi-resolution database 900. A target sequence is read in step 210. A map table may be created that records continuous runs of zeroes and gaps in the target sequence. The runs of zeroes and gaps may be identified for the purpose of removing them from the data prior to preparing database 900. The locations may be later used when interpreting the search results and determining match positions in the target sequence. A unit size is calculated to partition the entire target sequence (for example, the number of frames per section discussed above) for forming database 900.

In step 220, the target may be encoded to intermediates as illustrated in FIG. 4A. In step 240, the intermediates may be encoded to form multi-resolution database 900. Different tracks may be output from database 900 with one or more channels. An R superposition plus an S superposition is an example of two channels of wavefunction frame data, and the final track 6 of database 900 is an example with one channel of wavefunction frame data. The different tracks correspond to different depths of superposition as discussed above.

It is typically desired to want to exploit the maximum number of layers of superposition can be searched in parallel in any one particular instance in order to have the maximum search efficiency. The layer depth of superpositions that can be processed typically depends on the number of defined bases in the probe sequence. The longer the probe, the greater layer depth of superpositions that can be used in doing the search because of the greater uniqueness of the probe.

For purposes of explanation, the layer depth limit is related to the signal-to-noise ratio (SNR). A longer probe will have a higher SNR than a shorter probe. For each length of probe, there is typically a superposition layer depth that can be effectively processed. It is desired to have a database that has different layered depths in it that may be selected as optimal for different probes. For example, the database will have greater layer depths for longer probes, shorter layer depths for shorter probes, and for the shortest probe, it may have a depth of only a single layer.

In step 260, a non-encoded target sequence track may be created. This track is separate from, but may be synchronized on a frame basis, with the wavefunction frames in other tracks. As a result, this non-encoded target sequence track may be more efficiently accessed for any wavefunction frame by using the corresponding frame counter or index. This non-encoded track may include position dependent annotations at various positions along the target sequence and/or hyperlinks that may present additional information to a user or permit a user to interactively link to additional information about various positions on the target while interacting with and interpreting search results (e.g., while viewing results on user display 205).

Figure 9:
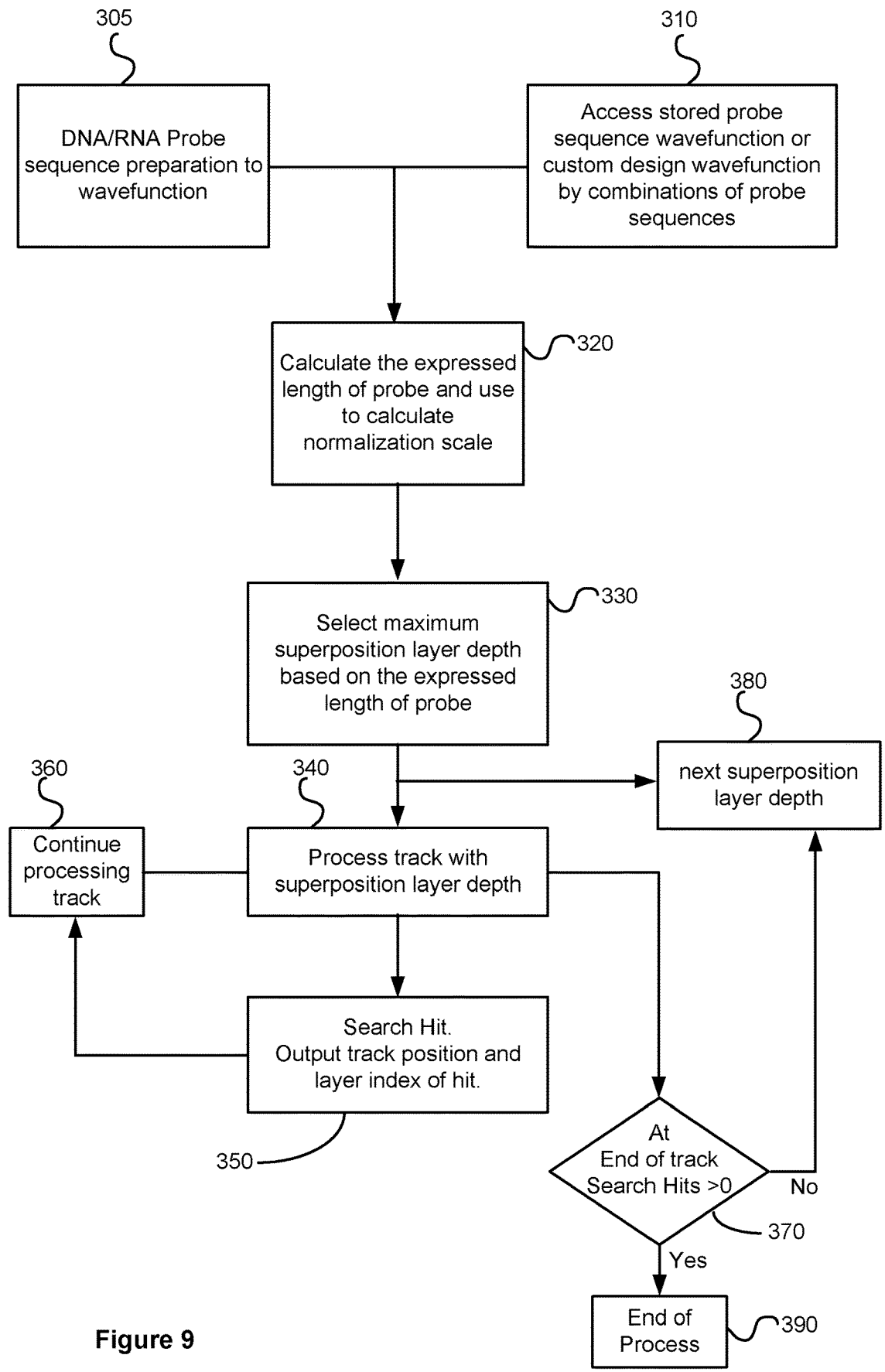
FIG. 9 illustrates the selection of a track from the multi-resolution database, the searching for hits in the selected track, and the selection of a next track for searching, in accordance with some embodiments.

FIG. 9 illustrates the selection of a track 902 from multi-resolution database 900, the searching for hits in the selected track, and the selection of a next track 902 at a different resolution for continued searching. A DNA/RNA probe sequence is prepared in step 305 by transforming to wavefunction form as discussed above. Alternatively, in step 310, a previously prepared probe sequence wavefunction may be obtained from storage (e.g., memory) for use, or combinations of probe sequences may be used to prepare customized wavefunctions for particular applications.

The probe sequence selected for use is passed to step 320, in which the expressed length of the probe is calculated. The expressed probe length is used to calculate the normalization scale factor applied during the searching process discussed above in modulus and normalization steps 122 and 140. Normalization is desired to attempt to make the output correlation peaks independent of the probe length.

In step 330, the maximum superposition layer depth is selected based on the expressed length of probe from step 320. In step 340, a track 902 is selected from multi-resolution database 900 corresponding to the maximum superposition layer depth that may be efficiently processed for the effective length of the probe. Then, a search as described above in FIG. 5 for method 100 is performed.

In step 350, a search hit (e.g., an R, S Hit Pair) from executing method 100 is output with its track position and the layer index of the hit. Processing of the track continues in step 360 to determine if additional search hits will be found. For example, anywhere from one to millions of hits may be found from the search of the first selected track 902.

In step 370, if the process is at the end of the selected track and at least one search hit has been found, then the process ends in step 390. If no search hits were found, then in step 380 another superposition layer depth is selected (e.g., half the layer depth just used in the failed search), and the corresponding track 902 is obtained from database 900 for additional processing using method 100 at step 340.

Figure 10:
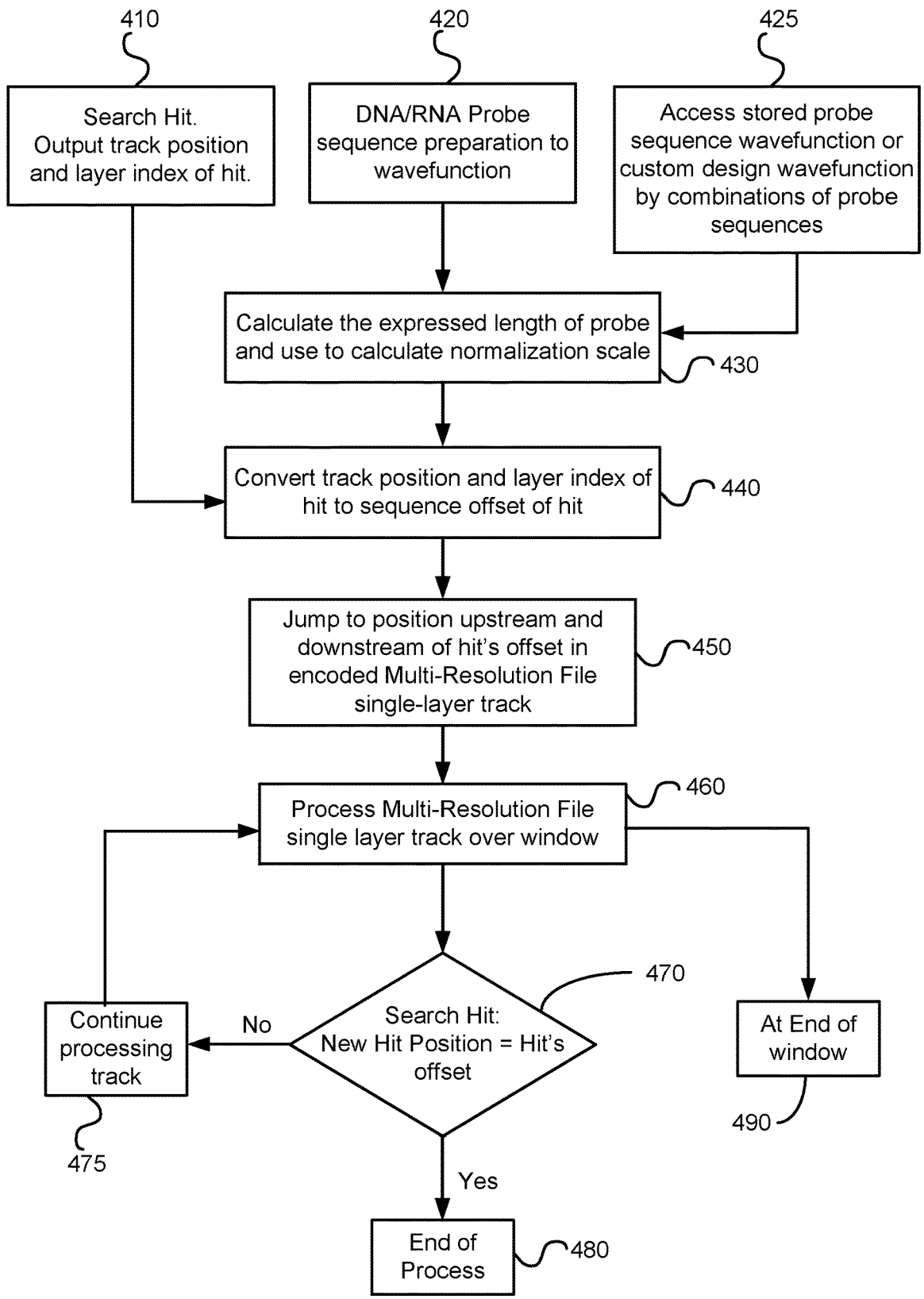
FIG. 10 illustrates the use of a single-layer track in the multi-resolution database to confirm a search hit located from the prior searching of one of several multiple-layer tracks in the multi-resolution database according to an exemplary embodiment of the present disclosure.
Figure 11A:
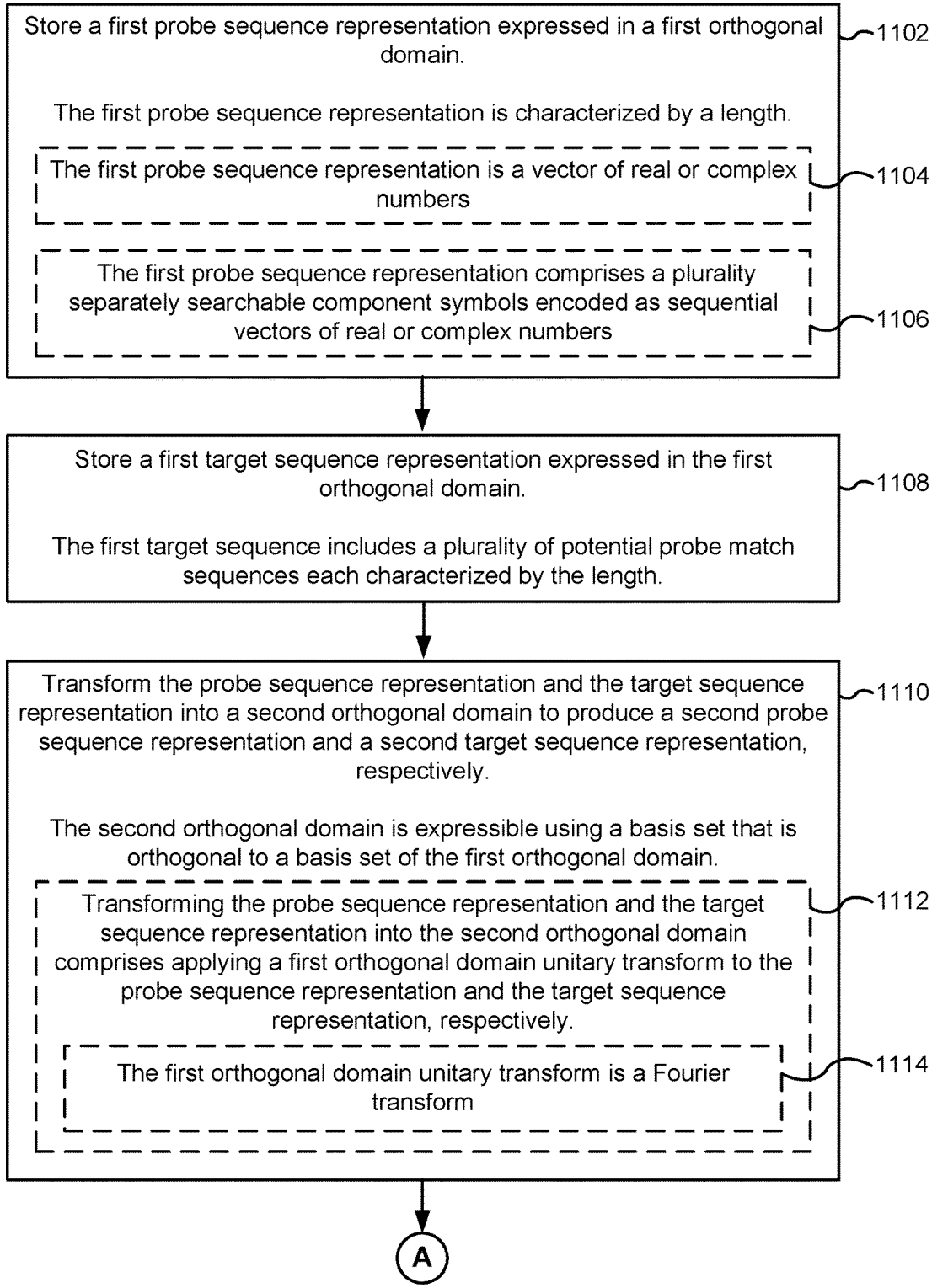
FIGS. 11A-11D illustrate a flowchart for method of sequence searching, in accordance with some embodiments.
Figure 11B:
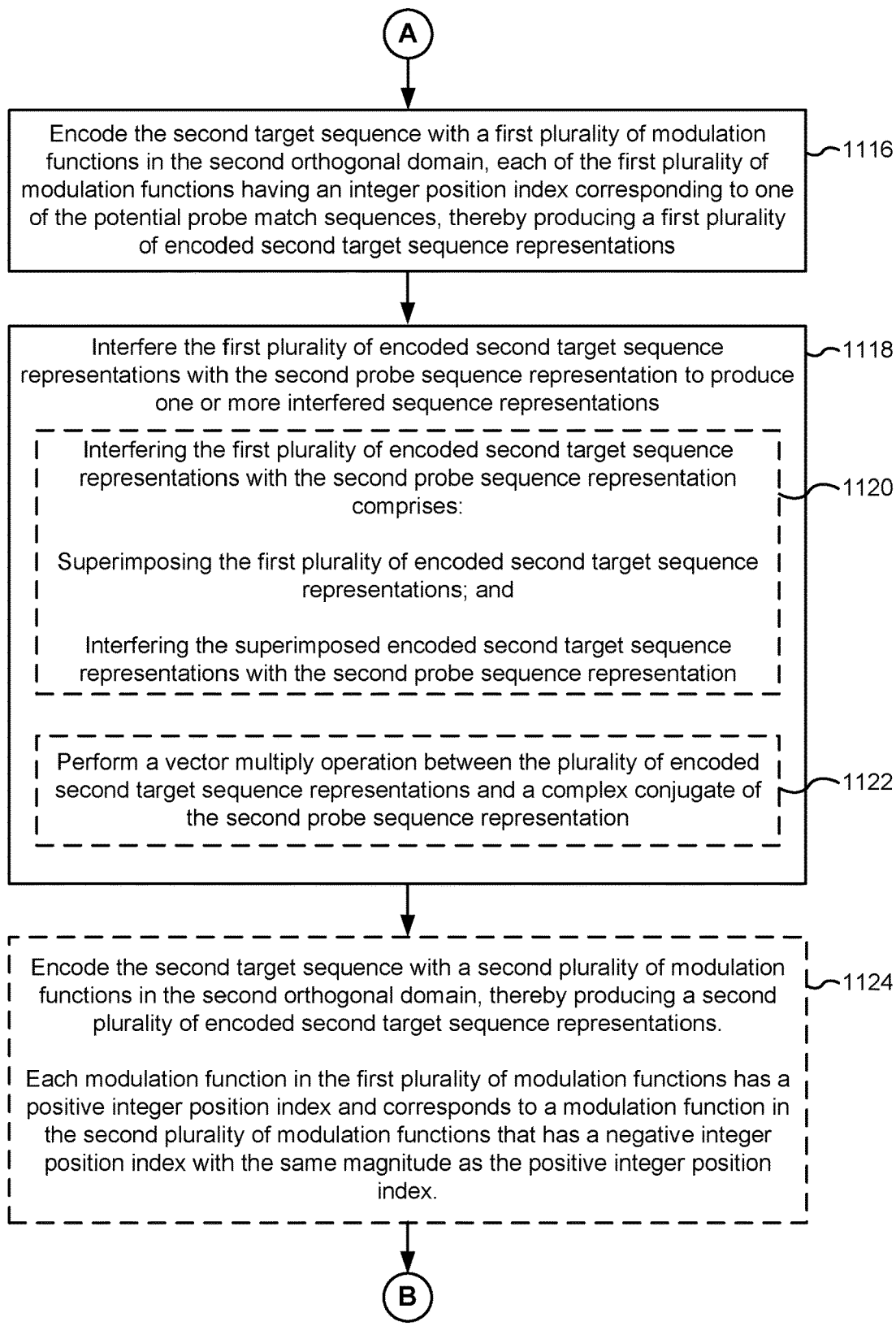
Figure 11C:
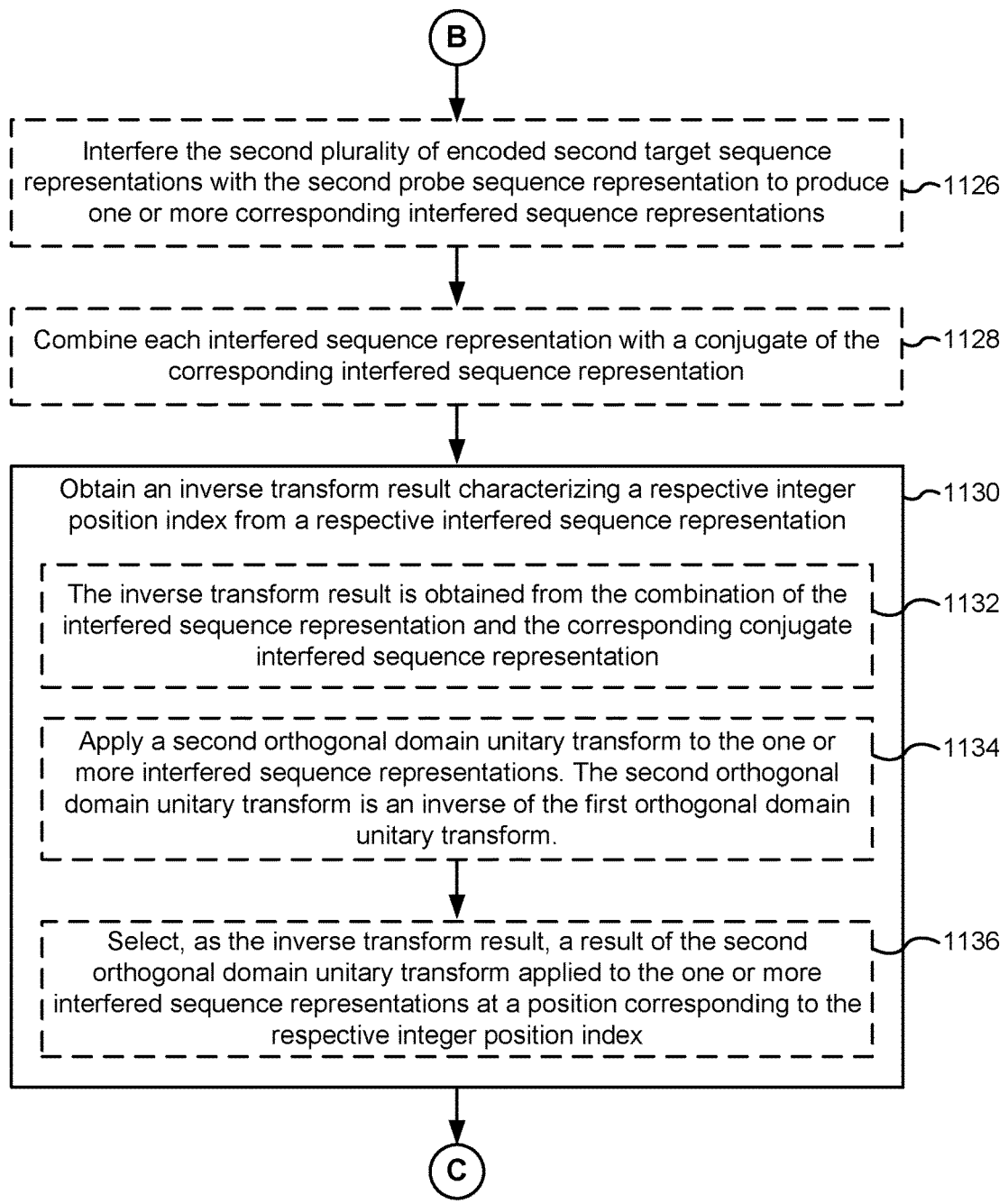
Figure 11D:
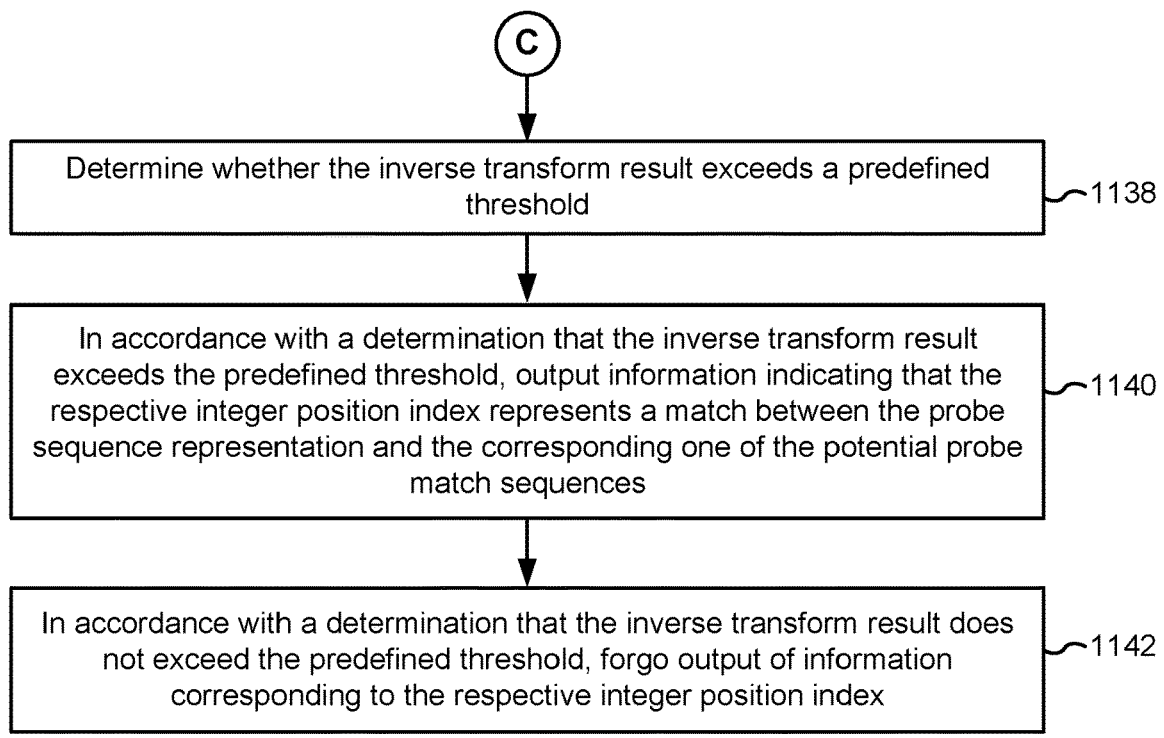

FIG. 10 illustrates the use of a single-layer track in the multi-resolution database to confirm one or more search hits located from one of several multiple-layer tracks 902 in the multi-resolution database 900. A probe input is selected in steps 420 and 425 are similar to steps 305 and 310 discussed above, and a probe length is determined in step 430 similarly as discussed above in step 320. In step 410, the one or more search hits from step 350 are used as an input to step 440.

In step 440, the track position and layer index of each incoming search hit are converted to a target sequence offset. In other words, the track position can be converted to a sequence offset of the hit within the original input sequence. As discussed above, in step 182 the layer index may be converted to a target section number. The track position may then be calculated as the count of frames from the track start plus the length of a single target section times the target section number.

In step 450, the process determines a position in the target sequence that is upstream of the search hit's offset in the single-layer track 902 (e.g., Track 6 of FIG. 6) of the multi-resolution database 900. Step 450 is performed to attempt to confirm that a hit actually exists in the original target location identified from the search of method 100.

Simply stated, a separate process is started for each potential search hit that is generated from method 100 of FIG. 5. A search hit is processed again over a range (referred to below as a "window") bounded by a small positional distance upstream from the search hit's position in the target sequence to a small positional distance downstream (e.g., this may be just a couple of frames). Each search hit may be confirmed by checking the single-layer track of database 900 (note that there is no superposition in the single-layer track). It should be noted that in the single-layer track of database 900, dual R, S data is not needed. This is so because, if the separation between the R and S data is twice the layer index and layer index zero is being used, then the R and S data are identical and only the R or S data is needed.

In step 460, the single-layer track is processed over the window that is determined by the primary frame that contains the position of the hit, plus an additional downstream (successor) frame if the position within the frame is such that part of the matching sequence is in that downstream frame. In addition it may be desirable to start processing with the frame that is immediately upstream (preceding) the frame that contains the hit in order to provide an overlap frame at steps 116 and 134 that will be combined via steps 118 and 136 with the primary frame that contains the position of the hit. The prepared probe sequence from step 420 or 425 is used here again, in addition to the search that generated the search hit, because the interference process is basically being repeated on the single-layer track as a confirmation of the search hit.

In step 470, if the hit position determined from the single-layer track is equal to the input search hit position, then the process ends at step 480. If the hit position is not equal to the input position, then in step 475 the single-layer track is processed further. If the hit position is upstream (preceding) the input position, processing will continue until the input position has been reached and passed. The processing of a single wavefunction frame will yield a full N potential match alignments, so even the minimum window equal to a single frame will detect all the potentially multiple match alignments that may be present in the target sequence information inside this window. In this way, all of the multiple hits will be detected based even a single hit occurring an a superposition layer interference as in method 100. Processing of the single-layer track continues until the end of the window being processed is reached at step 490.

FIGS. 11A-11D illustrate a flowchart of method 1100 for sequence searching, in accordance with some implementations. In particular, some implementations of method 700 illustrate optimizations to any of the previously described methods for the special case when the probe has a fixed length and the target includes a plurality of potential matches all having the same fixed length. This situation is described elsewhere in this document as a target having a natural modulus. It is also described as a "zero-offset use case," because a priori knowledge of the length of the potential matches allows the target data to be structured in such a way as to guarantee a zero-offset result within a given matching layer. For example, consider a list of United States phone numbers. Each phone number, including area code, has 10 digits. So, in this example, the natural modulus is 10. Moreover, when searching for a match to a specific phone number within that list (e.g., a probe phone number), a match that starts in the middle of one phone number and overlaps onto the next phone number, in this situation, is not a match at all. Thus, the offset in such a use case is always zero because only matches that begin at the beginning of a phone number are considered. Such a priori knowledge obviates the need for certain steps and operations described elsewhere in this document. In particular, such a prior knowledge obviates the need for a storage buffer and leads to optimizations in how the target sequence is stored, as described below.

It should be understood that the operations in method 1100 may be performed by a single computer system or may be divided among several computer systems. For ease of explanation, method 1100 is described as being performed by a single computer system (e.g., computer system 1200, FIG. 12).

The computer system stores (1102) a first probe sequence representation expressed in a first orthogonal domain. The first probe sequence representation is characterized by a length (e.g., a natural or predefined length). In some embodiments, the first probe sequence representation is (1104) a vector of real or complex numbers. Considering the example illustrated above, a natural or predefined length for a United States phone number, including area code, is 10 real numbers. Thus, in some embodiments, method 1100 can be used for lookup in a reverse phone book.

In some embodiments, the first probe sequence representation comprises a plurality separately searchable component symbols encoded as sequential vectors of real or complex numbers. For example, considering a sequence of playing cards: spades could be encoded with a value of "1"; hearts could be encoded with a value of "−1"; diamonds with a value of "j" (where j is the imaginary unit); and clubs with a value of "−j." In this sense, component symbols are encoded as real or complex numbers, and an encoded sequence of such component symbols comprises a sequence of real or complex numbers. The domain in which the probe sequence representation is initially expressed in (i.e., the first orthogonal domain) is sometimes referred to as the spatial domain. But in many applications, this designation is purely arbitrary.

The computer system stores (1108) a first target sequence representation expressed in the first orthogonal domain. The first target sequence includes a plurality of potential probe match sequences each characterized by the length. In some embodiments, the process of encoding the potential probe match sequences into the first target sequence representation is analogous to the process described with reference to FIG. 4A, with the difference being that the sequence does not necessarily comprise DNA or RNA nucleotide bases.

The computer system transforms (1110) the probe sequence representation and the target sequence representation into a second orthogonal domain to produce a second probe sequence representation and a second target sequence representation, respectively. The second orthogonal domain is expressible using a basis set that is orthogonal to a basis set of the first orthogonal domain. In some embodiments, transforming (1112) the probe sequence representation and the target sequence representation into the second orthogonal domain comprises applying a first orthogonal domain unitary transform to the probe sequence representation and the target sequence representation, respectively. In some embodiments, the first orthogonal domain unitary transform is (1114) a Fourier transform (e.g., a computer-implemented Fourier transform and/or a discrete Fourier transform). Such unitary orthogonal transforms are described further with reference to step 24 (FIG. 3A).

In some circumstances, representations expressed in the second orthogonal domain are referred to herein as "wavefunctions." Such wavefunctions can be superimposed (e.g., by vector addition). The result of a superposition of one or more wavefunctions (i.e., representations in the second orthogonal domain) is variously referred to as: "superpositions"; "superposition wavefunctions"; or "superimposed wavefunctions."

The computer system encodes (1116) the second target sequence with a first plurality of modulation functions in the second orthogonal domain, each of the first plurality of modulation functions having an integer position index corresponding to one of the potential probe match sequences, thereby producing a first plurality of encoded second target sequence representations. Each of the first plurality of encoded second target sequence representations is described herein as a "layer." For example, considering a list of 10 phone numbers, each phone number is transformed into the second orthogonal domain, and modulated (e.g., encoded) with a modulation function (e.g., a transformed delta function), to form a layer. The layers are added together to form a superposition, which represents the list of 10 phone numbers. In some circumstances, this encoding is considered a convolution of each of the potential matches with a unique delta function in the first orthogonal domain. The convolution, however, is performed in the second orthogonal domain.

As noted above, in some embodiments, the modulation functions are delta functions. Thus operation 1116 proceeds similarly to operation 46 (FIG. 4A). However, several optimizations are optionally applied for the zero-offset use case, in accordance with some embodiments. For example, in some embodiments, the number of useable encoding layers may be increased when a multiplication factor is applied to the separation of the layer index encoded as delta function position index step 46 of FIG. 4A. This increase in the number of useable encoding layers means that deeper superpositions comprising more layer-encoded representations (i.e., "wavefunctions") can be used and so more target representations can be searched in parallel, thereby increasing performance. The increase in the number of useable encoding layers occurs because the multiplication factor applied to the separation of the layer index encoded as delta function position index step 46 of FIG. 4A decreases the signal overlap between different layer encoded representations.

Continuing with method 1100, the computer system interferes (1118) the first plurality of encoded second target sequence representations with the second probe sequence representation to produce one or more interfered sequence representations. This operation proceeds in an analogous fashion to steps 112 and 130 (FIGS. 5A-5D). To that end, in some embodiments interfering the first plurality of encoded second target sequence representations with the second probe sequence representation comprises (1120) superimposing the first plurality of encoded second target sequence representations (i.e., to generate the wavefunction) and interfering the superimposed encoded second target sequence representations (i.e., the wavefunction) with the second probe sequence representation. In some circumstances, this operation is considered a convolution of the probe sequence and the first plurality of encoded second target sequence representations (which is stored as a wavefunction superposition). The convolution is carried out in the second orthogonal domain, e.g., by performing (1122) a vector multiply operation between the plurality of encoded second target sequence representations and a complex conjugate of the second probe sequence representation.

In some embodiments, the encoding is a dual encoding, meaning that in addition to the encoding described with reference to operation 1116, the computer system encodes (1124) the second target sequence with a second plurality of modulation functions in the second orthogonal domain, thereby producing a second plurality of encoded second target sequence representations. Each modulation function in the first plurality of modulation functions has a positive integer position index and corresponds to a modulation function in the second plurality of modulation functions that has a negative integer position index with the same magnitude as the positive integer position index. This aspect of the present disclosure is discussed with reference to the preparation of target wavefunction superpositions R and S, respectively (e.g., step 110 and 128, FIG. 5C). Likewise, the computer system interferes the second plurality of encoded second target sequence representations with the second probe sequence representation to produce one or more corresponding interfered sequence representations (which is described with reference to steps 112 and 132, FIG. 5C). The computer system further combines (1128) each interfered sequence representation with a conjugate of the corresponding interfered sequence representation, as shown with reference to step 186 (FIG. 5D). An alternative to the conjugate approach is the reflection of data about zero lag, as described with reference to step 183 (FIG. 5C).

The computer system obtains (1130) an inverse transform result characterizing a respective integer position index from a respective interfered sequence representation. In some embodiments, the inverse transform result is (1132) obtained from the combination of the interfered sequence representation and the corresponding conjugate interfered sequence representation (e.g., because they have been combined per step 1128 to enhance the signal-to-noise). In some embodiments, obtaining the inverse transform includes applying (1134) a second orthogonal domain unitary transform to the one or more interfered sequence representations. The second orthogonal domain unitary transform is an inverse of the first orthogonal domain unitary transform (e.g., an inverse discrete Fourier transform). The result is a convolution in the first orthogonal domain. This operation is analogous to step 114 (FIG. 5A) except that step 114 can be optimized when the encoded delta function indices of consecutive layers are separated by a multiplication factor (as described above). Namely, the unitary orthogonal inverse transform step 114 can be modified to only calculate output data corresponding to the zero position offset and the encoding superposition layer. Using such a modified unitary orthogonal inverse transform step 114, the number of output data calculated will be a fraction of the unmodified unitary orthogonal inverse transform step 114 output, where this fraction is the reciprocal of the multiplication factor applied to the separation of the layer index encoded as delta function position index step 46 of FIG. 4A. Thus, in some embodiments, step 114 in FIGS. 5C-5D should be understood to be the modified version of this step.

When the convolution represents a hit, it will have a strong delta signal in the first orthogonal domain. On the contrary, a convolution between a probe and a non-hit will not produce a delta signal. Thus, in some embodiments, the computer system selects (1136), as the inverse transform result, a result of the second orthogonal domain unitary transform applied to the one or more interfered sequence representations at a position corresponding to the respective integer position index.

To be sure that the selected result represents a true hit, the computer system determines (1138) whether the inverse transform result exceeds a predefined threshold. In accordance with a determination that the inverse transform result exceeds the predefined threshold, the computer system outputs (1140) information indicating that the respective integer position index represents a match between the probe sequence representation and the corresponding one of the potential probe match sequences. In accordance with a determination that the inverse transform result does not exceed the predefined threshold, the computer system forgoes (1142) output of information corresponding to the respective integer position index.

Figure 12:
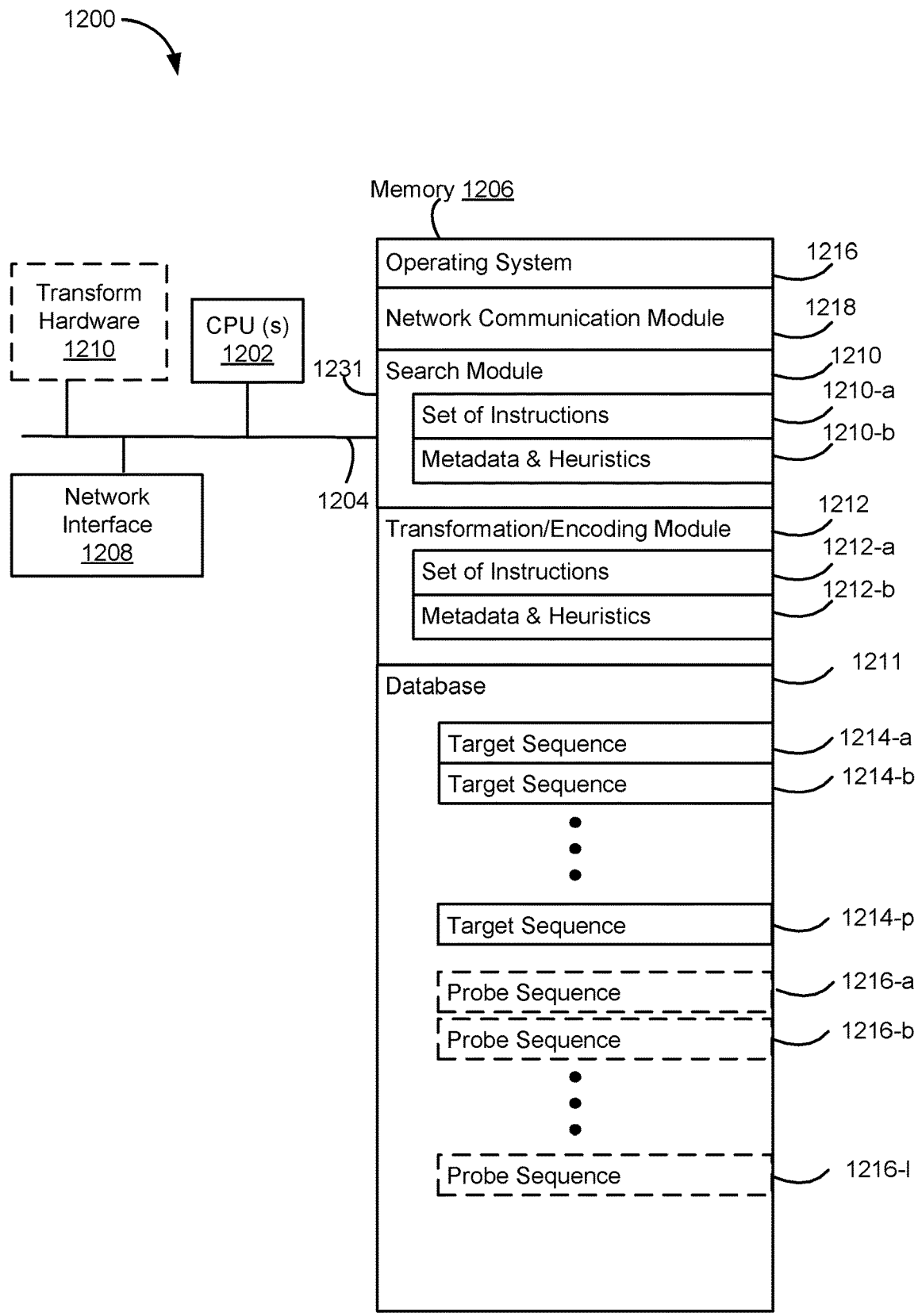
FIG. 12 illustrates a block diagram of a server system for sequence searching, in accordance with some embodiments.

FIG. 12 is a block diagram illustrating an example of a computer system 1200 for sequence search, in accordance with some embodiments. In some embodiments, computer system 1200 is analogous to, or shares any of the features of, computer system 200 (FIG. 2). While certain specific features are illustrated, those skilled in the art will appreciate from the present disclosure that various other features have not been illustrated for the sake of brevity and so as not to obscure more pertinent aspects of the implementations disclosed herein. To that end, computer system 1200 includes one or more processing units or cores (CPUs) 1202, one or more network or other communications interfaces 1208, memory 1206, optional transform hardware 1210 and one or more communication buses 1204 for interconnecting these and various other components. Communication buses 1204 may include circuitry (sometimes called a chipset) that interconnects and controls communications between system components. Memory 1206 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 1206 may optionally include one or more storage devices remotely located from CPU(s) 1202. Memory 1206, including the non-volatile and volatile memory device(s) within memory 1206, comprises a non-transitory computer readable storage medium.

In some implementations, memory 1206 or the non-transitory computer readable storage medium of memory 1206 stores the following programs, modules and data structures, or a subset thereof including operating system 1216, network communication module 1218, search module 1210, transformation/encoding module 1212, and database 1211.

Operating system 1216 includes procedures for handling various basic system services and for performing hardware dependent tasks.

Network communication module 1218 facilitates communication with other devices (e.g., other server systems and/or client devices) via one or more network interfaces 1208 (wired or wireless) and one or more communication networks, such as the Internet, other wide area networks, local area networks, metropolitan area networks, and so on.

Search module 1210 is configured to perform various tasks described with reference to FIG. 11A-11D as well as elsewhere in this document. For example, in some embodiments, search module 1210 encodes target sequences 1214 (e.g., target sequence 1214-$a$ through 1214-$p$, which are stored in database 1211) with modulation functions to produce a plurality of encoded target sequences. In some embodiments, search module 1210 interferes encodes target sequences 1214 with probe sequences 1216 (e.g., probe sequence 1216-$a$ through 1216-1, which are optionally stored in database 1211). To this end, search module 1210 includes a set of instructions 1210-$a$ and, optionally, metadata and heuristics 1210-$b$.

In some embodiments, search module 1210 calls transformation/encoding module 1212 to perform various transformations, such as the unitary orthogonal transformations described elsewhere in this document (other modules, not shown, may also call transformation/encoding module 1212 as necessary). In turn, in some embodiments, transformation/encoding module 1212 optionally utilized specialized hardware, such as transform hardware 1210 to perform calculations necessary to perform the unitary orthogonal transformations. In some embodiments, transform hardware 1210 is or is similar to a video card. In some embodiments, transform hardware 1210 includes its own firmware for performing such calculations. To perform these and other tasks, transform/encoding module 1210 includes a set of instructions 1212-$a$ and, optionally, metadata and heuristics 1212-$b$.

Search Output Display

Another aspect of the present disclosure is a method for presenting search results to a user. More specifically, the output may be presented to a user as a graph or other visual representation to illustrate the results of the search using a particular probe. This output may be presented, for example, on user display 205. This visual representation also may dynamically change its appearance to show correlations, their strengths and phases as output from method 100 or in the hit confirmation processing step 450. The normalized magnitude calculated in steps 122 and 140 may be represented as the height of a graph (e.g., the y-axis) at any point along a sequence position axis (e.g., the x-axis). Where multiple hits occur, the height of the graph may represent the count of matches within an arbitrary length frame or sliding window (e.g., histogram frequencies rather than individual matches).

The graph may, for example, display peaks of various heights for which the height is a quantitative measure of the binding energy between probe and its matching sequence in the target. The peaks may be positioned along an axis containing the target sequence. For example, either a similarity match or a double-stranded complementary base pairing match may be selected (for either DNA or RNA).

Each peak may further be coded with different colors to indicate the phase of the match. For example, a red color may be used to highlight strong in-phase matches so that red peaks are the most significant features in the visual display.

Additional information regarding the providing of visual representations to a user of the output search results is provided in APPENDIX A to this application, which is hereby fully incorporated by reference herein.

Custom Search Service Example

The following is a non-limiting example of a custom search service that may be provided using the present disclosure. A user provides target and probe information for processing using the above system and method. The information, results, and service may be communicated and provided using an application service provider (ASP) business model over, for example, the Internet.

The user designs one or more probes according to the following typical design rules: The total probe length is between 5 and 2,048 bases. Each base position may be individually specified to be one of A, C, T, or G, or each position may be specified to contain a blend of two different bases, for example a purine base hybrid that represents either adenine or guanine, or a pyrimidine base hybrid that represents either cytosine or thymine.

Each base may be individually weighted to be more or less significant by a factor γk specifying the overall weight given to that base position, where k is the individual base position starting at index 0. The default γk is set to 100%.

For example, to program a gene probe comprising a number of expressed exons, plus promoters and regulatory binding sites with non-coding bases between them, the exonic, promoter and regulatory sequences would be represented with different γk values. For instance, evolutionarily-conserved base positions and known functional patterns may be given accordingly greater $Y_k$ values. As another example, protein coding frames may be designed giving greater weight to the first and second base positions in each codon in a mRNA translation reading frame, and proportionally less weight given to the third base positions (since these may not affect amino acid coding of the triplet), since all base triplet codon patterns can be expressed using γk. A pattern of absolute gaps may be formed by setting γk to zero.

The probes are processed against the desired chromosome and genome targets, then the results are provided to the user. This may be a map that includes the position of direct hits and close homologies of the probe in the target DNA. Both matching and complementary sequences may be detected equally. Furthermore, hits may be ranked according to a distance metric representing the total base pair match/mismatch enthalpy calculated at single base pair resolution.

Applications

The system and method of the present disclosure are useful in a wide variety of data storage and searching applications such as, for example, surveying short sequences involved in gene regulation. The present disclosure may be applied to providing an "in silico" assay that has single base resolution to serve DNA primer design and screening, a need that is common to all DNA amplification bio-assays using the Polymerase Chain Reaction (PCR).

Additional applications include the following areas: screening oligonucleotide sequences for their ability to selectively bind desired target sites and not bind other undesired sites (this screening may be useful in siRNA gene silencing to safely and selectively turn off genes based on designer oligonucleotides); accelerating the drug discovery cycle by replacing complex and expensive wet laboratory tests with faster software tools using the system and method disclosed herein; screening for specificity of genetically engineered zinc finger DNA binding proteins and related designed endonucleases, and mapping of (micro RNA) miRNA complementary sites within genes and transcribed DNA, as potential gene regulation sequences.

It will be apparent from the foregoing that the wavefunctions as described possess a desirable property as contrasted to conventional database data encoding in that it achieves delocalized distribution of individual data items in such a way that is robust even in the presence of multiple point errors. This aspect of the method may be exploited by using analog or digital media and functional processing methodologies that are lower cost due to a tolerance of defects and noise as compared against, for example, higher-cost defect-free media and noise-free functional processing methodologies.

It will also be apparent from the foregoing that various steps in the method including unitary orthogonal transform and its inverse, and the interference of multiple wavefunction may each be realized in an optical system. Such functional implementation may proceed to the extent that the microprocessor component in the system may become non-essential, for example, if all steps are performed by dedicated optical hardware.

Yet other applications of the present disclosure are in the associative memory, quantum computing, and other fields and include the following applications: coding and decoding data for wideband communications, database search, biometrics, network routing optimization, free energy dynamics, universal sensor archival search and storage, financial market analysis, and retail data mining.

The system and method described herein may be used to provide a quantum memory component to perform an associative memory pattern matching function, and that may be logically extended by adding further quantum processing and algorithm components around the quantum memory core to build a quantum computer. Such a quantum computer may use photonic hardware and be based on laser optics.

CONCLUSION

As previously stated, the disclosure is not limited to searching of DNA/RNA sequences and while the foregoing description was made in this specific context, the disclosure can be utilized in many other application areas, including, but not limited to, other types of pattern recognition and data searching processes and the other areas discussed above.

Additionally, it can be readily understood that the foregoing processes can be embodied in a computer program that is executed by computer hardware that includes one or more processors for executing the computer program or other hardware variations mentioned above. The computer program can be stored on any type of recording medium such as a magnetic drive, floppy disk, tape drive, CD-ROM, flash memory, etc. and the disclosure is not limited to any particular type of recording medium or computer hardware.

By the foregoing disclosure, an improved system and method for a storing and searching large data sets (e.g., stored in a database) have been described. Although specific exemplary systems and methods were described above, one of skill in the art will recognize that in other embodiments many of the above steps may be re-arranged and/or omitted. The foregoing description of specific embodiments reveals the general nature of the disclosure sufficiently that others can, by applying current knowledge, readily modify and/or adapt it for various applications without departing from the generic concept. Therefore, such adaptations and modifications are within the meaning and range of equivalents of the disclosed embodiments. The phraseology or terminology employed herein is for the purpose of description and not of limitation.

Appendix A

A visual output display method is described here as an example of how DNA and RNA search results may be presented to a user. Search output results have traditionally been text-based showing, for example, the probe sequence aligned to a matching target sequence, together with some location information such as a chromosome position index. These text results are useful for close examination of matches that are output from the search. However, they have several limitations when used alone.

First, there is the problem of "not seeing the wood for the trees." In other words, there can be so much data that the overall patterns are not seen by the user. For shorter probes, such as lengths of twelve bases or less, the number of hits increases dramatically, so that there may be thousands of sequences output that match the probe. As a result of the large volume of matches, text output becomes overwhelming and confusing to the user. Second, traditional text output is not interactive in a way that easily allows a user to browse over the data set changing scope and focus according to their point of interest.

To overcome these limitations of text-based outputs, search results may be displayed as color-coded peaks on a three-dimensional virtual chromosome image. The position of this peak will correspond to the location of the match. Genes may be displayed as solid blocks so that it is apparent visually if a peak is located within a gene or outside it. The relative height of the peak may indicate the strength of the match, with 100% matches appearing as taller peaks than partial matches.

Alternatively, when there are a larger number of matches, the peak height may correspond to histogram frequency showing match density within a region, rather than single matches. Multiple different probe channels may be displayed as parallel tracks on a three-dimensional virtual chromosome. In this way, the results of multiple different searches may be compared at a glance across the entire chromosome. The use of multiple probe channels in the display can reveal subtle dependencies and relationships between different sequence elements.

One advantage of a 3D display or model is that the user can select a viewpoint to focus on an area of special interest in a sequence. The viewpoint may be controlled in real-time by, for example, mouse clicks or movements so that the virtual reality experience is enhanced. For example, dragging a mouse left button across the screen or up-and-down may rotate the 3D model, allowing the user to view it from any angle.

Similarly, dragging a mouse right button across the screen or up and down may move the 3D model as a translation in space. The user may also zoom in to get a close up view of a part of the model or zoom out to see the entire chromosome using, for example, middle and right button mouse clicks. As the user's viewpoint zooms in closer to the chromosome, additional information may be displayed around the color-coded peaks or gene blocks. This may be alphanumeric information such as, for example, a chromosome position, base sequence or gene label.

The probe and matching target sequence may be displayed as three-dimensional text strings. This allows a mixed display containing both color-coded peaks and textual information in the same view. The textual and graphical information may include hypertext links, for example, to external data sources, programs, and Internet resources.

A separate user interface (e.g., control box) may also be provided showing which probes are displayed on the virtual chromosome and their color coding. Slider controls may also be used to control the scaling of the display peaks and position of text labels. Buttons may provide additional interactive display options for each probe channel.

The visual output display method above may be implemented on conventional computer hardware systems using any of a number of software languages.

What is claimed is:

1. A method, performed by a computer system having one or more processors and memory storing instructions for execution on the one or more processors, for parallel searching of probe data in a database of target data, the method comprising:

storing, as first data at a location within the memory, a first probe data representation expressed in a first orthogonal domain, wherein the first probe data representation is characterized by a length;

storing, as second data in the memory, a first target data representation expressed in the first orthogonal domain, wherein the first target data includes a plurality of potential probe match data each characterized by the length;

transforming the first probe data representation and the first target data representation into a second orthogonal domain to produce a second probe data representation and a second target data representation, respectively, wherein transforming the first probe data representation and the first target data representation into the second orthogonal domain comprises applying a first orthogonal domain unitary transform to the first probe data representation and the first target data representation, respectively, wherein the second orthogonal domain is expressible using a basis set that is orthogonal to a basis set of the first orthogonal domain;

storing the second probe data representation in the memory;

encoding the second target data representation with a first plurality of modulation functions in the second orthogonal domain, each of the first plurality of modulation functions having an integer position index corresponding to one of the potential probe match data, thereby producing a first plurality of encoded second target data representations;

superimposing the first plurality of encoded second target data representations to produce a superposition of the first plurality of encoded second target data representations;
storing the superposition of the first plurality of encoded second target data representations in the memory;
encoding the second target data representation with a second plurality of modulation functions in the second orthogonal domain, thereby producing a second plurality of encoded second target data representations, wherein each modulation function in the first plurality of modulation functions has a positive integer position index and corresponds to a modulation function in the second plurality of modulation functions that has a negative integer position index with the same magnitude as the positive integer position index;
superimposing the second plurality of encoded second target data representations to produce a superposition of the second plurality of encoded second target data representations;
storing the superposition of the second plurality of encoded second target data representations in memory;
creating a plurality of program instances, each of which retrieves from memory a different combination of the stored second probe representation and the pair comprising the stored superposition of the first plurality of encoded second target data representations and the stored superposition of the second plurality of encoded second target data representations;
interfering the superposition of the first plurality of encoded second target data representations with the second probe data representation to produce a first set of one or more interfered data representations;
interfering the superposition of the second plurality of encoded second target data representations with the second probe data representation to produce a second set of one or more corresponding interfered data representations;
combining each interfered data representation in the first set with a conjugate of the corresponding interfered data representation in the second set;
obtaining an inverse transform result characterizing a respective integer position index from a respective interfered data representation, wherein the inverse transform result is obtained from the combination of the interfered data representation in the first set and the corresponding conjugate interfered data representation in the second set;
determining whether the inverse transform result exceeds a predefined threshold; and
in accordance with a determination that the inverse transform result exceeds the predefined threshold, outputting, as the location in the memory where the first probe data is stored, the respective integer position index.

2. The method of claim 1, wherein interfering the first plurality of encoded second target data representations with the second probe data representation comprises performing a vector multiply operation between the plurality of encoded second target data representations and a complex conjugate of the second probe data representation.

3. The method of claim 1, wherein the first orthogonal domain unitary transform is a Fourier transform.

4. The method of claim 1, wherein obtaining the inverse transform result characterizing a respective integer position index comprises:
applying a second orthogonal domain unitary transform to the one or more interfered data representations, wherein the second orthogonal domain unitary transform is an inverse of the first orthogonal domain unitary transform; and
selecting, as the inverse transform result, a result of the second orthogonal domain unitary transform applied to the one or more interfered data representations at a position corresponding to the respective integer position index.

5. The method of claim 1, wherein the first probe data representation is a vector of real or complex numbers.

6. The method of claim 1, wherein the first probe data representation comprises a plurality separately searchable component symbols encoded as sequential vectors of real or complex numbers.

7. The method of claim 1, wherein the first data and the second data each comprise multi-dimensional data.

8. A computer system for parallel searching of probe data in a database of target data, comprising:
one or more processors; and
memory storing one or more programs for execution on the one or more processors, the one or more programs comprising instructions for:
storing, as first data at a location within the memory, a first probe data representation expressed in a first orthogonal domain, wherein the first probe data representation is characterized by a length;
storing, as second data in the memory, a first target data representation expressed in the first orthogonal domain, wherein the first target data includes a plurality of potential probe match data each characterized by the length;
transforming the first probe data representation and the first target data representation into a second orthogonal domain to produce a second probe data representation and a second target data representation, respectively, wherein transforming the first probe data representation and the first target data representation into the second orthogonal domain comprises applying a first orthogonal domain unitary transform to the first probe data representation and the first target data representation, respectively, wherein the second orthogonal domain is expressible using a basis set that is orthogonal to a basis set of the first orthogonal domain;
storing the second probe data representation in the memory;
encoding the second target data representation with a first plurality of modulation functions in the second orthogonal domain, each of the first plurality of modulation functions having an integer position index corresponding to one of the potential probe match data, thereby producing a first plurality of encoded second target data representations;
superimposing the first plurality of encoded second target data representations to produce a superposition of the first plurality of encoded second target data representations;
storing the superposition of the first plurality of encoded second target data representations in the memory;
encoding the second target data representation with a second plurality of modulation functions in the second orthogonal domain, thereby producing a second plurality of encoded second target data representations, wherein each modulation function in the first plurality of modulation functions has a positive integer position index and corresponds to a modulation function in the second plurality of modulation functions that has a negative integer position index with the same magnitude as the positive integer position index;

superimposing the second plurality of encoded second target data representations to produce a superposition of the second plurality of encoded second target data representations;

storing the superposition of the second plurality of encoded second target data representations in memory;

creating a plurality of program instances, each of which retrieves from memory a different combination of the stored second probe representation and the pair comprising the stored superposition of the first plurality of encoded second target data representations and the stored superposition of the second plurality of encoded second target data representations;

interfering the superposition of the first plurality of encoded second target data representations with the second probe data representation to produce a first set of one or more interfered data representations;

interfering the superposition of the second plurality of encoded second target data representations with the second probe data representation to produce a second set of one or more corresponding interfered data representations;

combining each interfered data representation in the first set with a conjugate of the corresponding interfered data representation in the second set;

obtaining an inverse transform result characterizing a respective integer position index from a respective interfered data representation, wherein the inverse transform result is obtained from the combination of the interfered data representation in the first set and the corresponding conjugate interfered data representation in the second set;

determining whether the inverse transform result exceeds a predefined threshold; and in accordance with a determination that the inverse transform result exceeds the predefined threshold, outputting, as the location in the memory where the first probe data is stored, the respective integer position index.

9. The computer system of claim 8, wherein interfering the first plurality of encoded second target data representations with the second probe data representation comprises performing a vector multiply operation between the plurality of encoded second target data representations and a complex conjugate of the second probe data representation.

10. A non-transitory computer readable storage medium, comprising:

one or more programs including instructions for execution by a computer system including one or more processors and memory, the one or more programs including instructions for:

storing, as first data at a location within the memory, a first probe data representation expressed in a first orthogonal domain, wherein the first probe data representation is characterized by a length;

storing, as second data in the memory, a first target data representation expressed in the first orthogonal domain, wherein the first target data includes a plurality of potential probe match data each characterized by the length;

transforming the first probe data representation and the first target data representation into a second orthogonal domain to produce a second probe data representation and a second target data representation, respectively, wherein transforming the first probe data representation and the first target data representation into the second orthogonal domain comprises applying a first orthogonal domain unitary transform to the first probe data representation and the first target data representation, respectively, wherein the second orthogonal domain is expressible using a basis set that is orthogonal to a basis set of the first orthogonal domain;

storing the second probe data representation in the memory;

encoding the second target data representation with a first plurality of modulation functions in the second orthogonal domain, each of the first plurality of modulation functions having an integer position index corresponding to one of the potential probe match data, thereby producing a first plurality of encoded second target data representations;

superimposing the first plurality of encoded second target data representations to produce a superposition of the first plurality of encoded second target data representations;

storing the superposition of the first plurality of encoded second target data representations in the memory;

encoding the second target data representation with a second plurality of modulation functions in the second orthogonal domain, thereby producing a second plurality of encoded second target data representations, wherein each modulation function in the first plurality of modulation functions has a positive integer position index and corresponds to a modulation function in the second plurality of modulation functions that has a negative integer position index with the same magnitude as the positive integer position index;

superimposing the second plurality of encoded second target data representations to produce a superposition of the second plurality of encoded second target data representations;

storing the superposition of the second plurality of encoded second target data representations in memory;

creating a plurality of program instances, each of which retrieves from memory a different combination of the stored second probe representation and the pair comprising the stored superposition of the first plurality of encoded second target data representations and the stored superposition of the second plurality of encoded second target data representations;

interfering the superposition of the first plurality of encoded second target data representations with the second probe data representation to produce a first set of one or more interfered data representations;

interfering the superposition of the second plurality of encoded second target data representations with the second probe data representation to produce a second set of one or more corresponding interfered data representations;

combining each interfered data representation in the first set with a conjugate of the corresponding interfered data representation in the second set;

obtaining an inverse transform result characterizing a respective integer position index from a respective interfered data representation, wherein the inverse transform result is obtained from the combination of the interfered data representation in the first set and the corresponding conjugate interfered data representation in the second set;

determining whether the inverse transform result exceeds a predefined threshold; and in accordance with a determination that the inverse transform result exceeds the predefined threshold, outputting, as the location in the memory where the first probe data is stored, the respective integer position index.

* * * * *